(12) United States Patent
McLaren et al.

(10) Patent No.: US 10,456,546 B2
(45) Date of Patent: Oct. 29, 2019

(54) AUTOMATICALLY ADJUSTING HEADGEAR FOR PATIENT INTERFACE

(71) Applicant: FISHER & PAYKEL HEALTHCARE LIMITED, Auckland (NZ)

(72) Inventors: Mark Arvind McLaren, Auckland (NZ); Jeroen Hammer, Auckland (NZ); Vitaly Kapelevich, Auckland (NZ); Brett John Huddart, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 864 days.

(21) Appl. No.: 14/786,942

(22) PCT Filed: Apr. 24, 2014

(86) PCT No.: PCT/NZ2014/000074
§ 371 (c)(1),
(2) Date: Oct. 23, 2015

(87) PCT Pub. No.: WO2014/175752
PCT Pub. Date: Oct. 30, 2014

(65) Prior Publication Data
US 2016/0082217 A1 Mar. 24, 2016

Related U.S. Application Data

(60) Provisional application No. 61/815,624, filed on Apr. 24, 2013, provisional application No. 61/866,953, (Continued)

(51) Int. Cl.
*A61M 16/06* (2006.01)
*A61M 16/08* (2006.01)
(52) U.S. Cl.
CPC .... *A61M 16/0683* (2013.01); *A61M 16/0616* (2014.02); *A61M 16/0666* (2013.01); (Continued)

(58) Field of Classification Search
CPC .......... A61M 16/0605; A61M 16/0683; A61M 16/0694; A44B 11/04; A44B 11/06–14; E06B 9/234; F16G 11/10–108
See application file for complete search history.

(56) References Cited

U.S. PATENT DOCUMENTS 2,661,514 A * 12/1953 Martin .................... E06B 9/324
24/134 KB
3,416,521 A 12/1968 Humphrey
(Continued)

FOREIGN PATENT DOCUMENTS

CN 1294527 A 5/2001
CN 101611944 A 12/2009
(Continued)

OTHER PUBLICATIONS

UK Intellectual Property Office, Further Examination Report, Application No. GB1518223.1, dated Apr. 9, 2018, in 4 pages.
(Continued)

*Primary Examiner* — Valerie L Woodward
(74) *Attorney, Agent, or Firm* — Knobbe Martens Olson & Bear LLP

(57) ABSTRACT

A headgear for securing a mask to a user's face is described. The headgear requires a first load force to elongate the headgear and, when fitted to a user, applies a balanced fit force that substantially equals a load force applied to the headgear during respiratory therapy. In some embodiments, the headgear includes an elastic portion configured to provide a retraction force, a non-elastic portion configured to be inelastic in comparison to the elastic portion, and a restriction mechanism connected to the non-elastic portion and to the elastic portion. The restriction mechanism is configured to apply a first resistance force to the user's head on
(Continued)

elongation of the headgear and a second resistance force to the user's head on retraction of the headgear.

20 Claims, 52 Drawing Sheets

Related U.S. Application Data filed on Aug. 16, 2013, provisional application No. 61/866,926, filed on Aug. 16, 2013, provisional application No. 61/871,789, filed on Aug. 29, 2013, provisional application No. 61/945,727, filed on Feb. 27, 2014.

(52) U.S. Cl.
CPC . *A61M 16/0816* (2013.01); *A61M 2205/0216* (2013.01); *A61M 2205/0244* (2013.01); *A61M 2205/0283* (2013.01); *A61M 2205/0294* (2013.01)

(56) References Cited

U.S. PATENT DOCUMENTS

| | | | |
|---|---|---|---|
| 3,792,702 A | | 2/1974 | Delest |
| 3,887,968 A | | 6/1975 | Lynam |
| 4,288,891 A | * | 9/1981 | Boden .............. F16G 11/101 24/115 G |
| 4,437,462 A | | 3/1984 | Piljay |
| 4,453,292 A | * | 6/1984 | Bakker .............. F16G 11/101 24/115 G |
| 4,458,373 A | * | 7/1984 | Maslow .............. F16G 11/101 12/142 LC |
| 4,477,928 A | | 10/1984 | Graff |
| 4,734,940 A | | 4/1988 | Galet et al. |
| 4,848,334 A | | 7/1989 | Bellm |
| 4,853,275 A | * | 8/1989 | Tracy .............. A41F 15/005 428/178 |
| 6,256,798 B1 | | 7/2001 | Egolf et al. |
| 6,338,342 B1 | | 1/2002 | Fecteau et al. |
| 8,047,893 B2 | | 11/2011 | Fenske |
| 2007/0130663 A1 | * | 6/2007 | Lang .............. A61M 16/0683 2/9 |
| 2007/0215161 A1 | | 9/2007 | Frater et al. |
| 2009/0320187 A1 | | 12/2009 | Petzl et al. |
| 2013/0074845 A1 | * | 3/2013 | Smith .............. A61M 16/06 128/205.25 |
| 2014/0158726 A1 | | 6/2014 | Malara |
| 2014/0358054 A1 | | 12/2014 | Capra et al. |
| 2015/0151070 A1 | | 6/2015 | Capra et al. |
| 2015/0290415 A1 | | 10/2015 | Dunn |

FOREIGN PATENT DOCUMENTS

| | | |
|---|---|---|
| CN | 102753230 A | 10/2012 |
| GB | 2478305 | 9/2011 |
| GB | 2491227 | 11/2012 |
| GB | 2553475 | 3/2018 |
| JP | 2018127729 A | 8/2018 |
| WO | WO 00/50122 | 8/2000 |
| WO | WO 2009/026627 | 3/2009 |
| WO | WO 2009/038918 A1 | 3/2009 |
| WO | WO 2009/148956 | 12/2009 |
| WO | WO 2010/066004 | 6/2010 |
| WO | WO 2010/131189 A1 | 11/2010 |
| WO | WO 2010/139014 | 12/2010 |
| WO | WO 2011/072739 | 6/2011 |
| WO | WO 2011/077254 | 6/2011 |
| WO | WO 2012/045127 | 4/2012 |
| WO | WO 2012/071300 | 5/2012 |
| WO | WO 2013/026091 | 2/2013 |
| WO | WO 2013/026092 | 2/2013 |
| WO | WO 2014/025267 | 2/2014 |
| WO | WO 2014/075141 | 5/2014 |
| WO | WO 2014/175752 | 10/2014 |
| WO | WO 2015/083060 | 6/2015 |
| WO | WO 2015/151019 | 10/2015 |
| WO | WO 2016/043603 | 3/2016 |
| WO | WO 2017/158544 | 9/2017 |
| WO | WO 2017/160166 | 9/2017 |

OTHER PUBLICATIONS

European Examination Report Received in European Patent Application No. 14788084.3, dated Jul. 28, 2017.
UK Intellectual Property Office, Combined Search and Examination Report, Application No. GB1807531.7, dated Jun. 6, 2018, in 7 pages.
Patent Examination Report No. 3, PCT/NZ2014/258011, dated Nov. 29, 2016 in 4 pages.
Intellectual Property Office Examination Report, received in Application No. GB1518223.1, dated Aug. 9, 2017, in 8 pages.
Chinese Search Report, Application 201480036019.X, filed on Apr. 24, 2014, in 24 pages.
UK Intellectual Property Office, Examination Report under Section 18(3), Application No. GB1518223.1, dated Jun. 25, 2018, in 4 pages.
International Search Report; Application No. PCT/NZ2014/000074; filed Apr. 24, 2013.
Extended European Search Report for EP14788084.3, dated Sep. 16, 2016, in 6 pages.
International Search Report and Written Opinion in application No. PCT/NZ2015/050149 dated Dec. 24, 2015 in 18 pages.
UK Intellectual Property Office, Combined Search and Examination Report, Application No. GB 1807533.3, dated Jun. 6, 2018, in 9 pages.
Australian Government, Examination Report No. 1, Application No. 2016259409, dated Jul. 23, 2018, in 8 pages.
Examination Report for GB1518223.1, dated Aug. 15, 2018, in 3 pages.
Examination Report for GB1807343.7, dated Aug. 15, 2018, in 5 pages.
Examination Report for GB1807531.7, dated Aug. 15, 2018, in 4 pages.
Examination Report for GB1807533.3, dated Aug. 15, 2018, in 6 pages.
Examination Report for GB1807363.5, dated Aug. 15, 2018, in 7 pages.
Examination Report in GB1807363.5 dated Sep. 21, 2018 in 7 pages.
Examination Report in GB1807533.3 dated Sep. 21, 2018 in 4 pages.
Examination Report in GB1807531.7 dated Sep. 21, 2018 in 4 pages.
Examination Report in GB1807343.7 dated Sep. 21, 2018 in 6 pages.
Japan Office Action in JP 2016-510641 dated Aug. 20, 2018 in 8 pages.

* cited by examiner

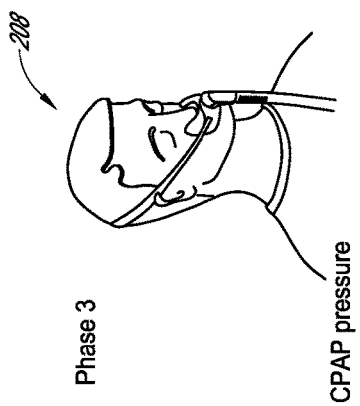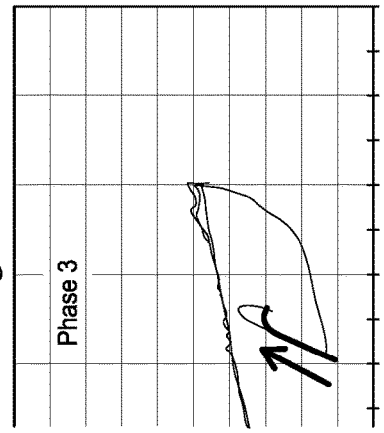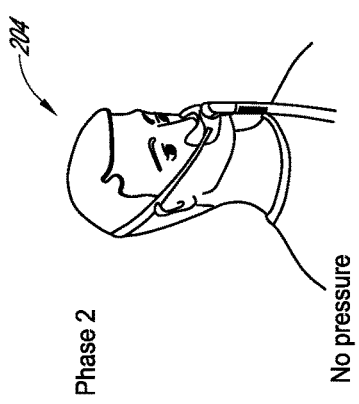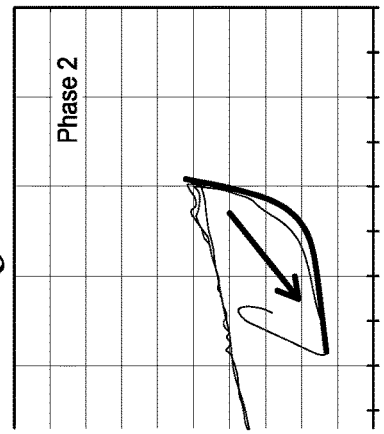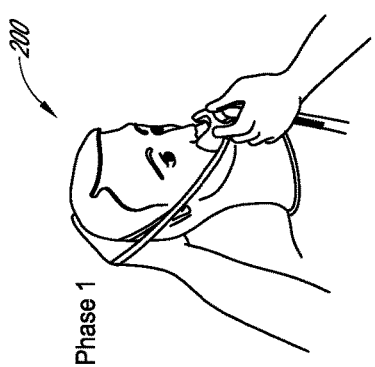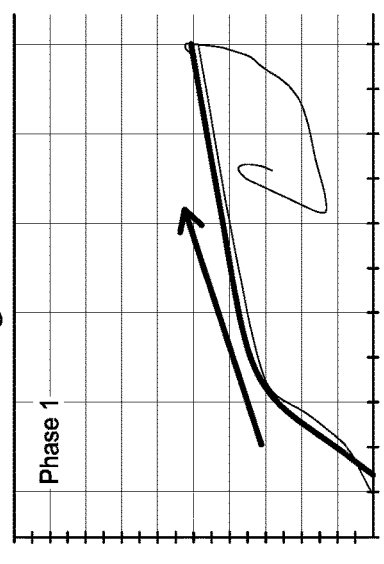

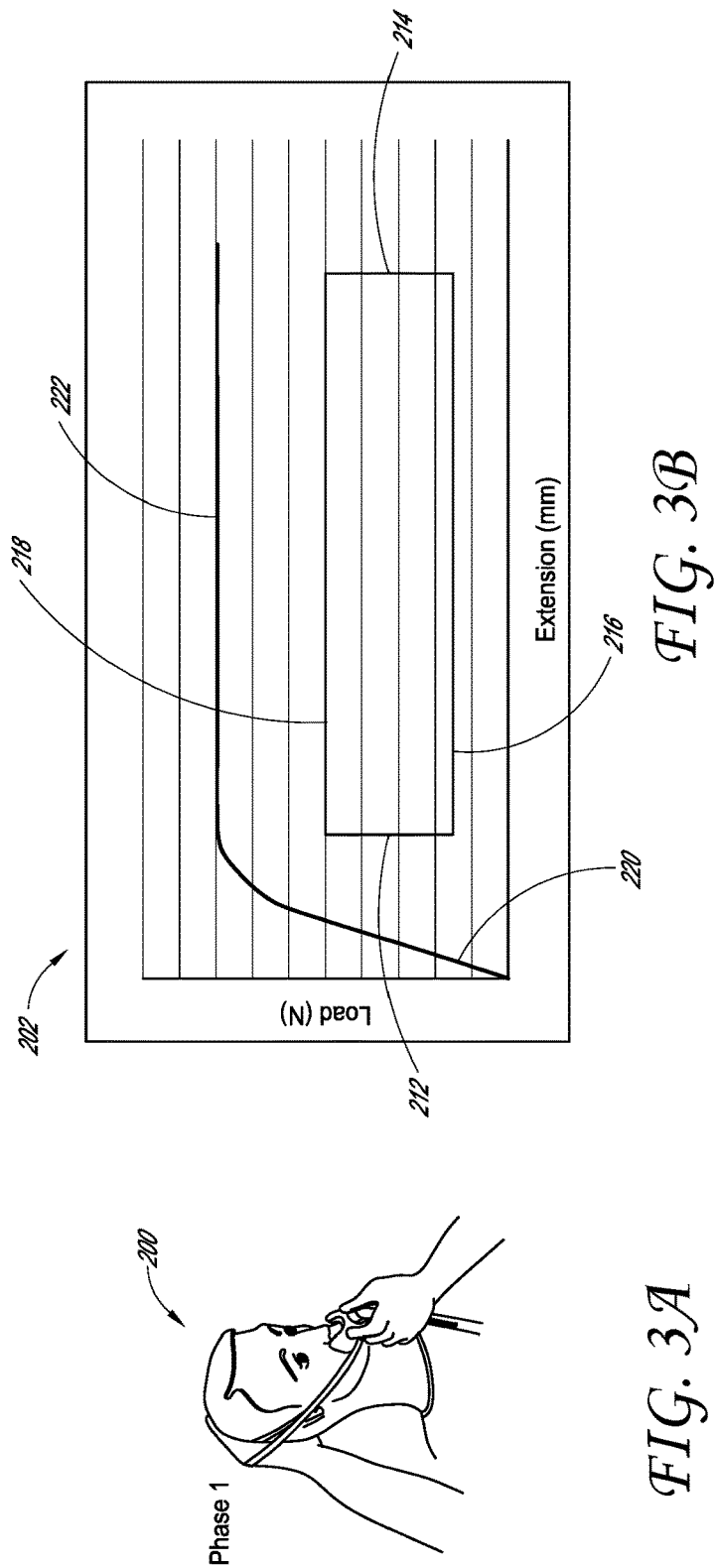

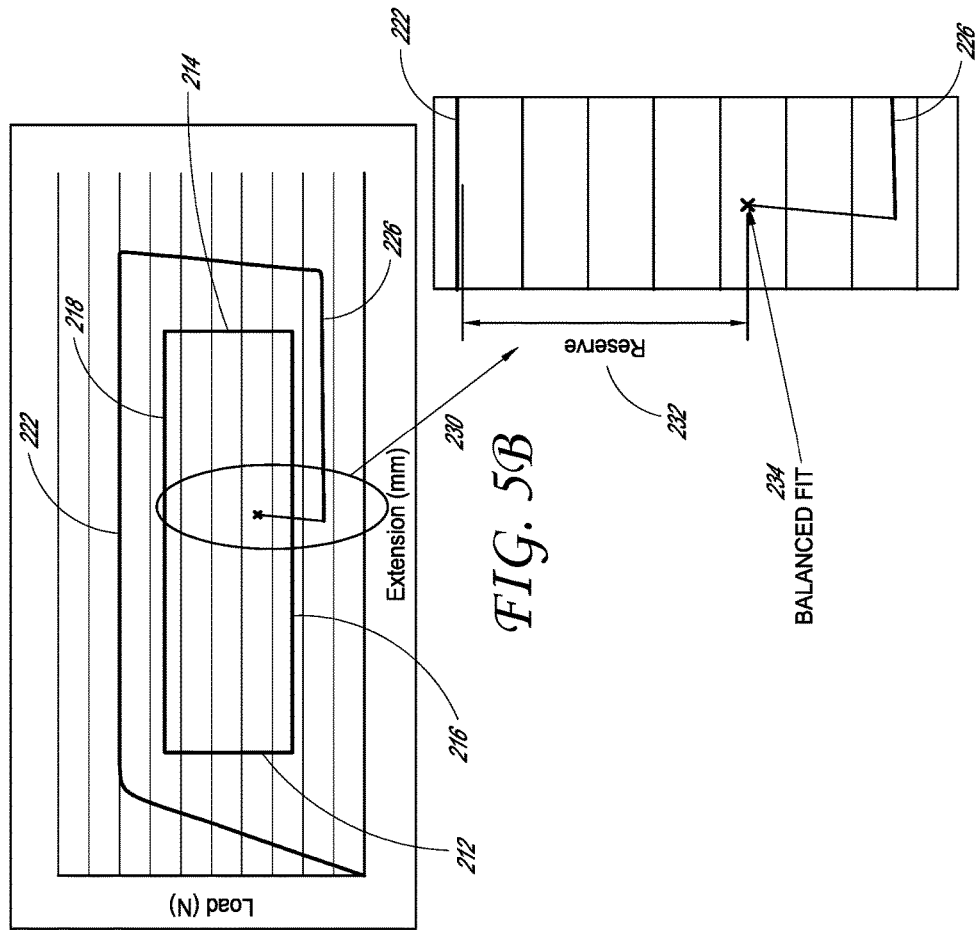
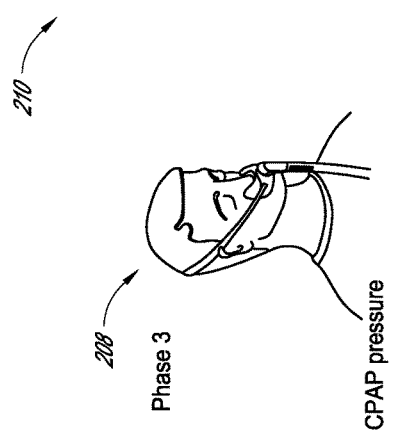
FIG. 5A
FIG. 5B
FIG. 5C

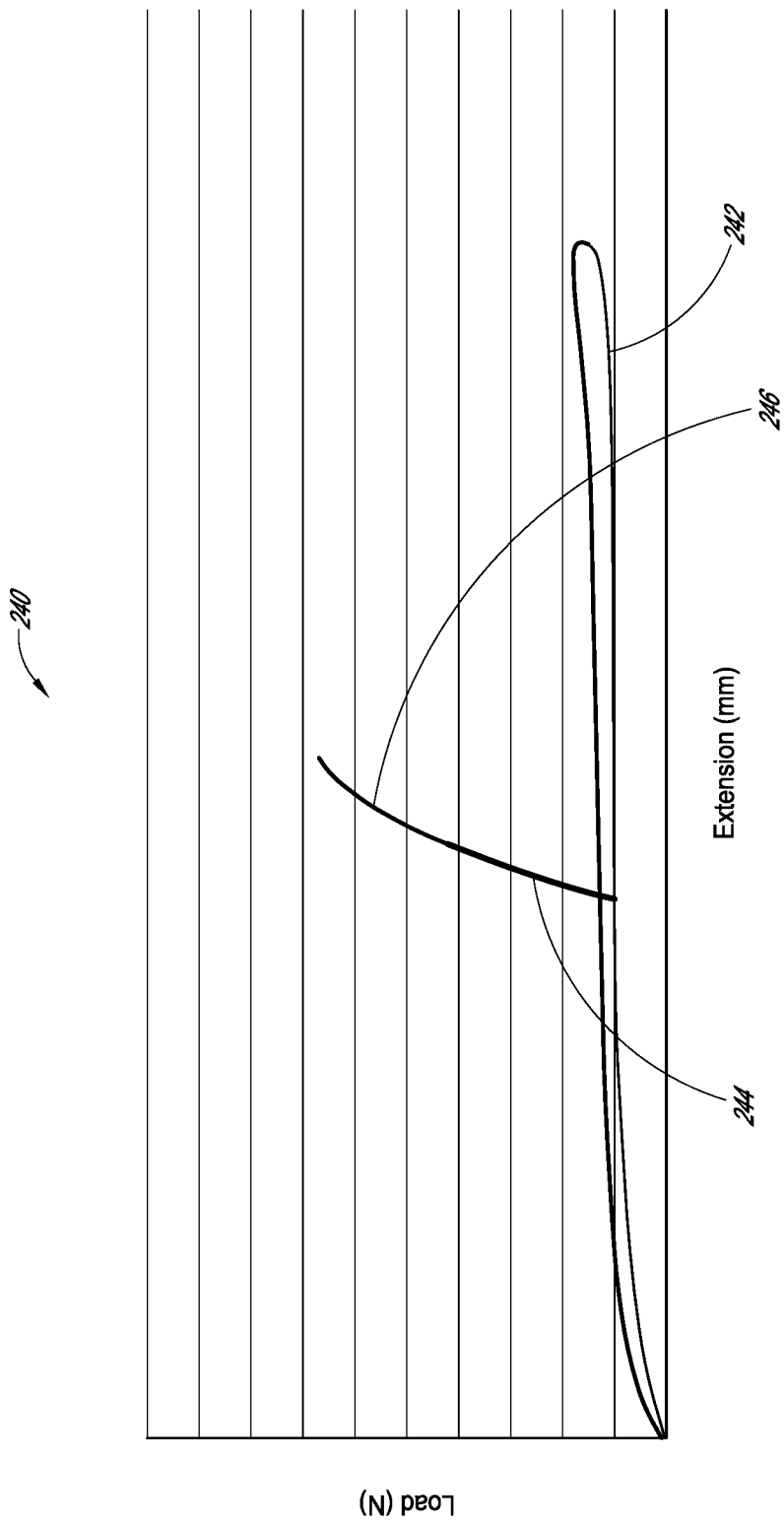

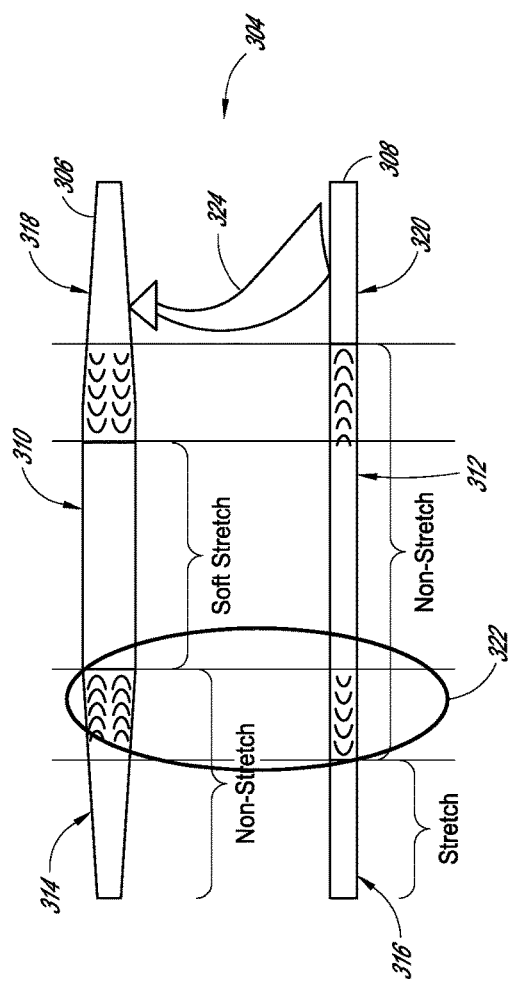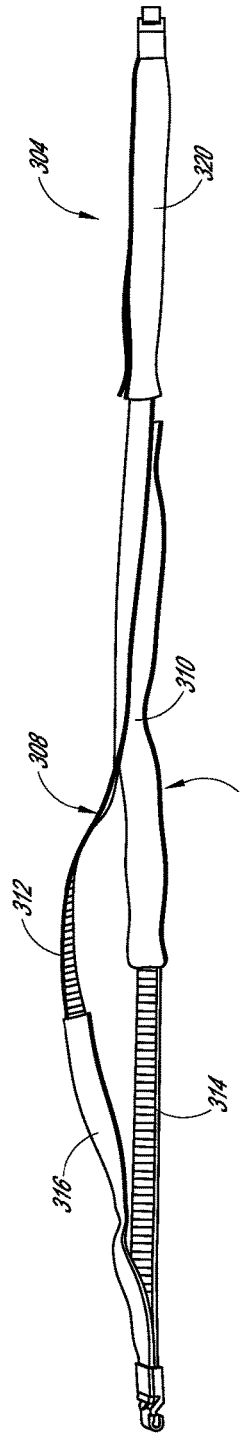
FIG. 7A
FIG. 7B

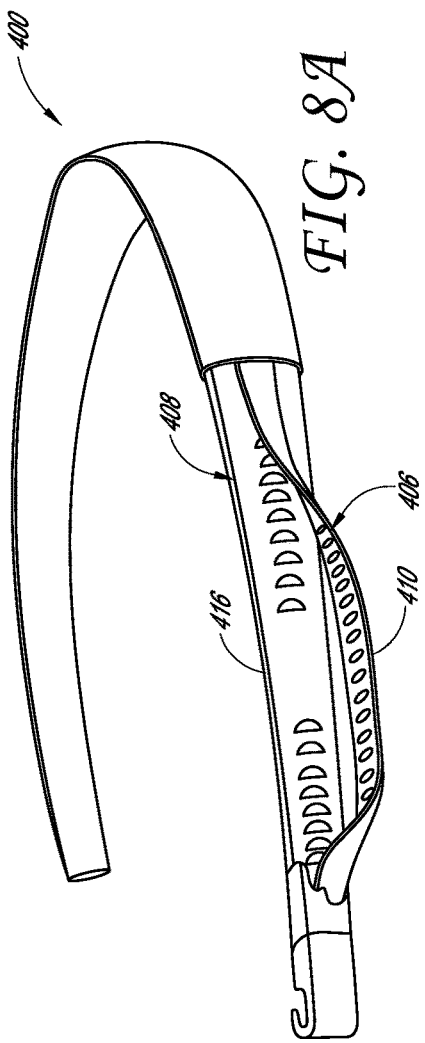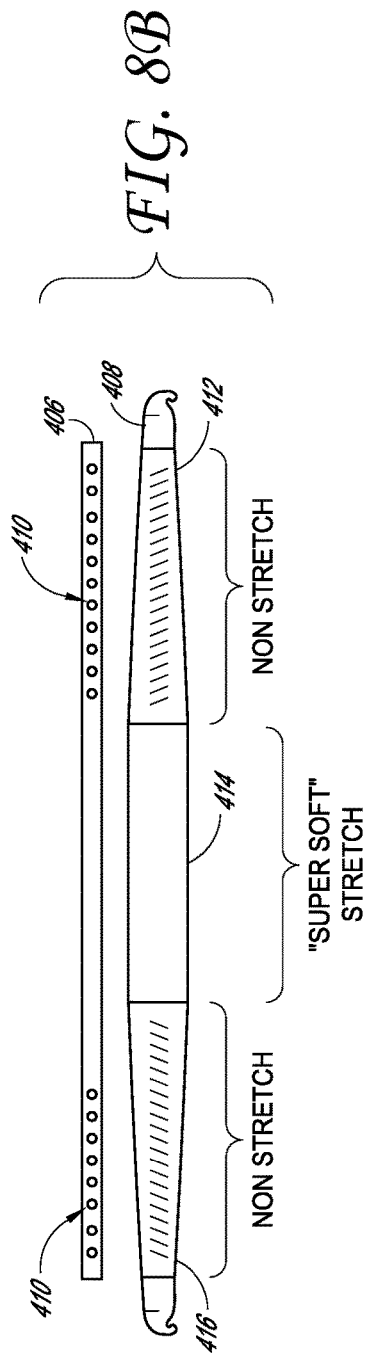

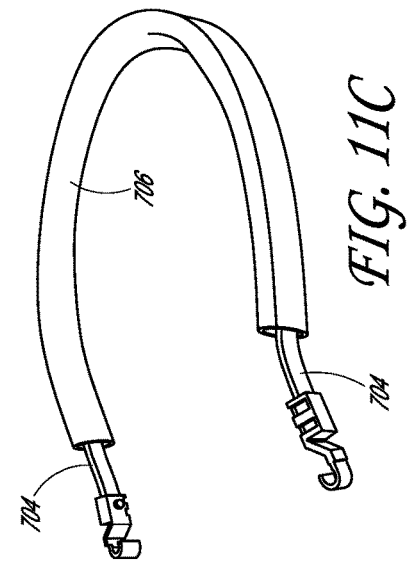
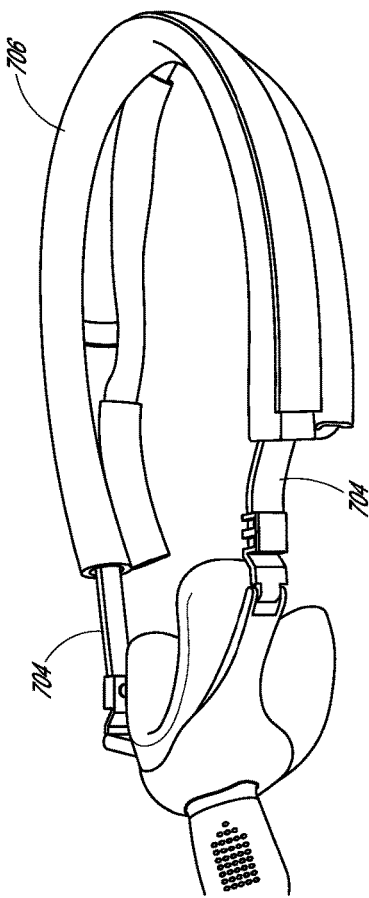
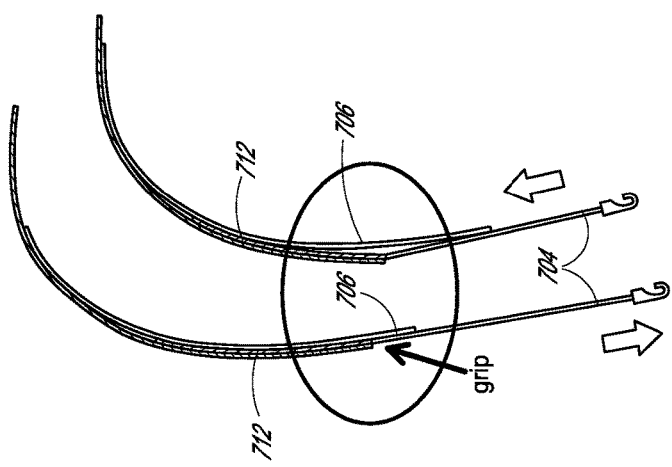

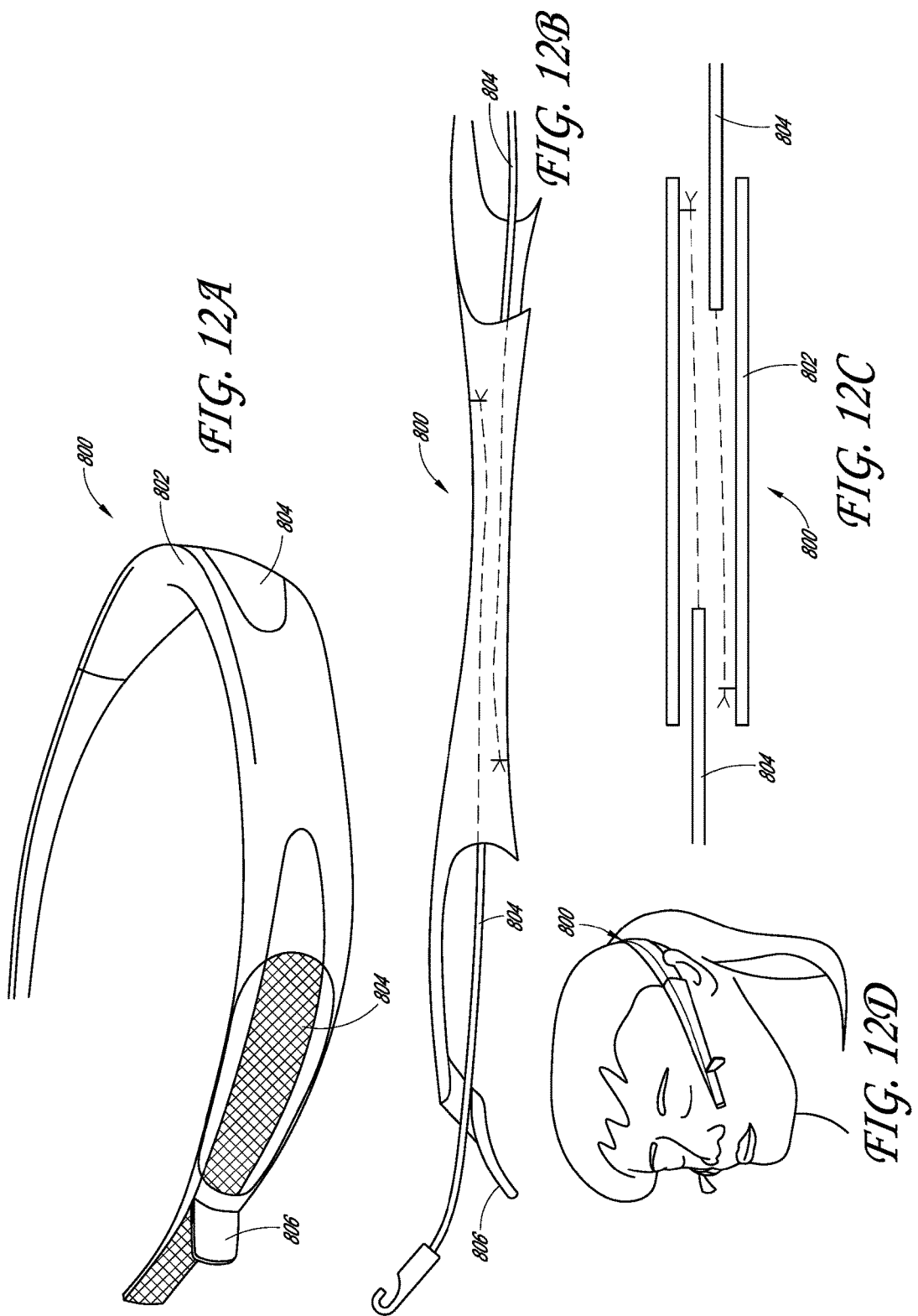

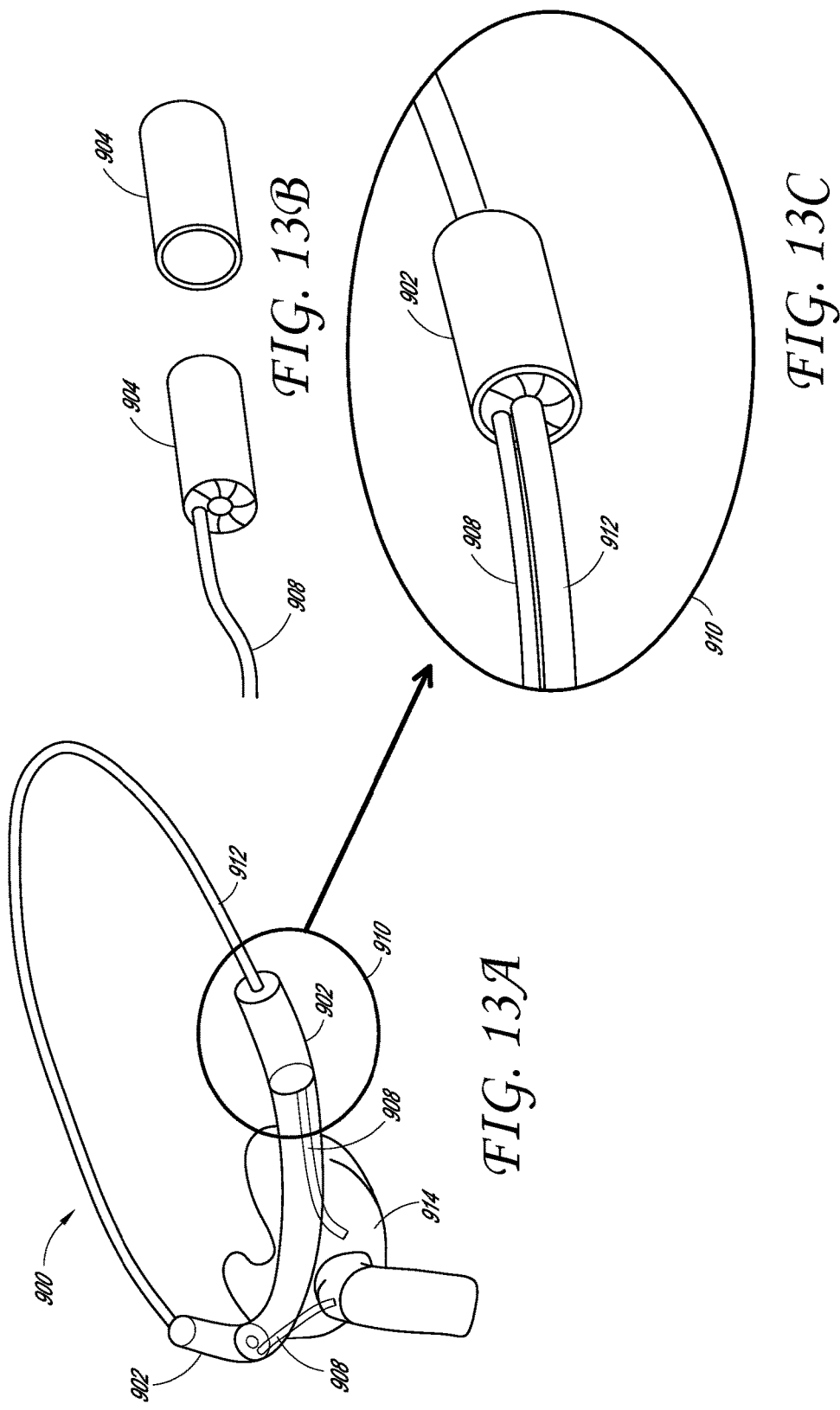

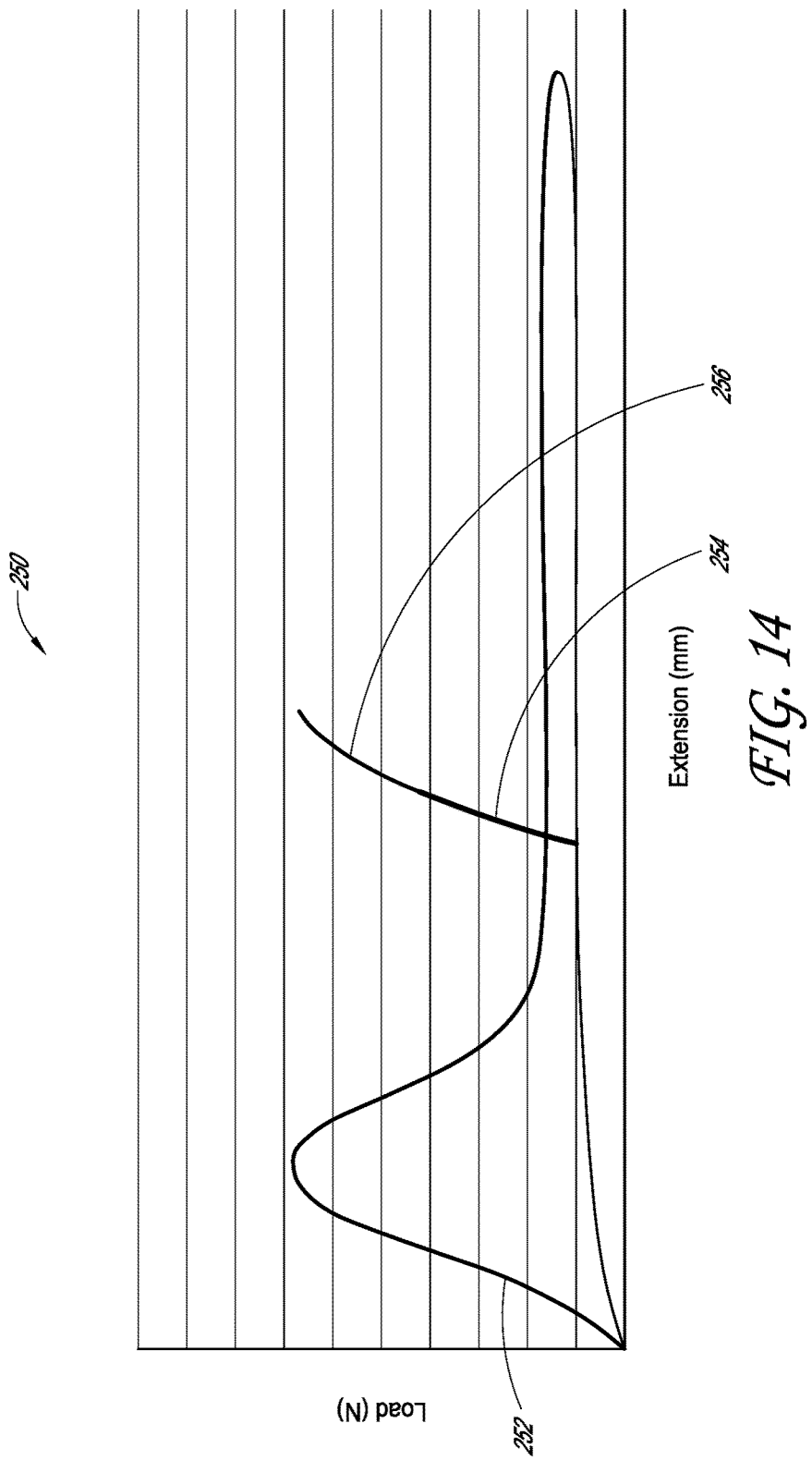

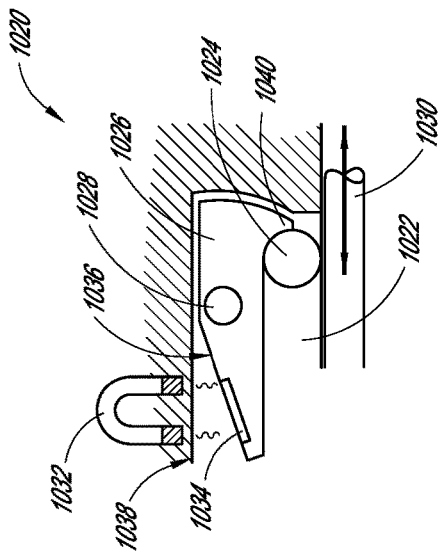
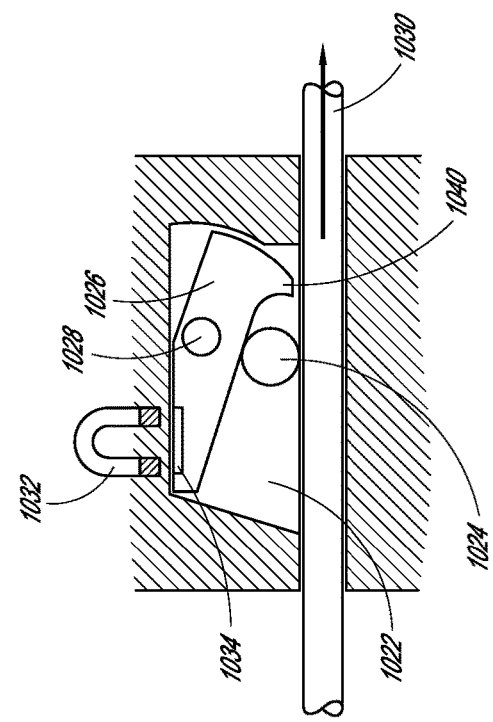
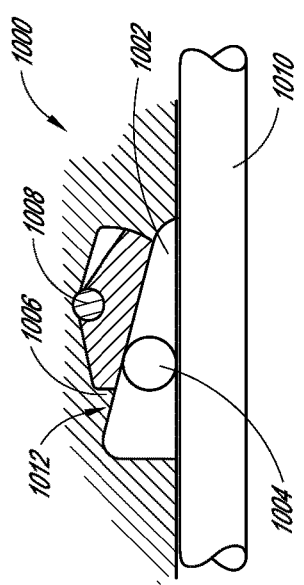
FIG. 15A
FIG. 15B
FIG. 15C

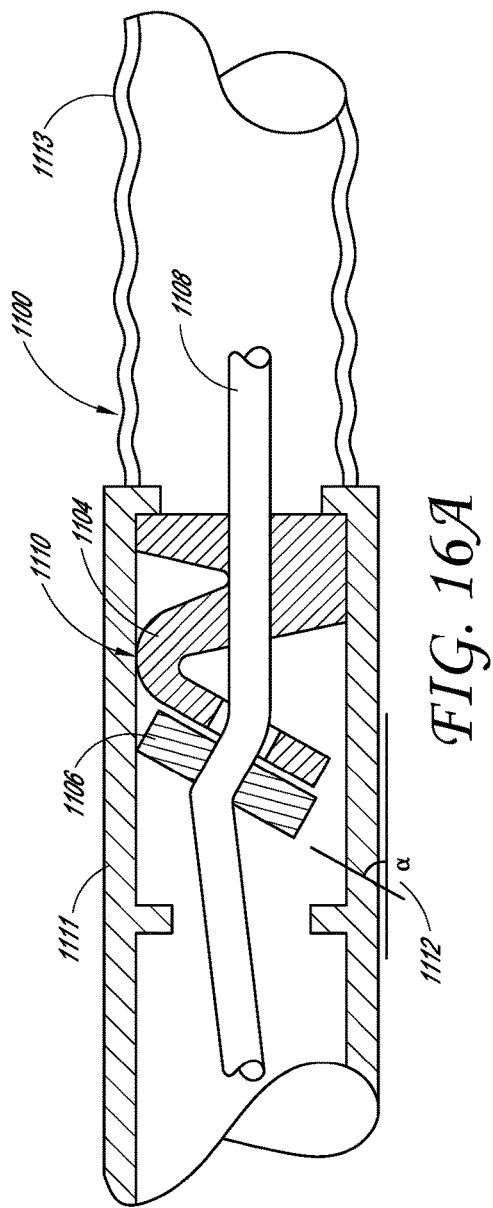
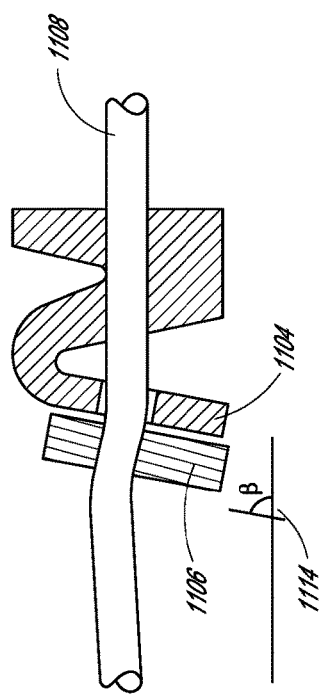

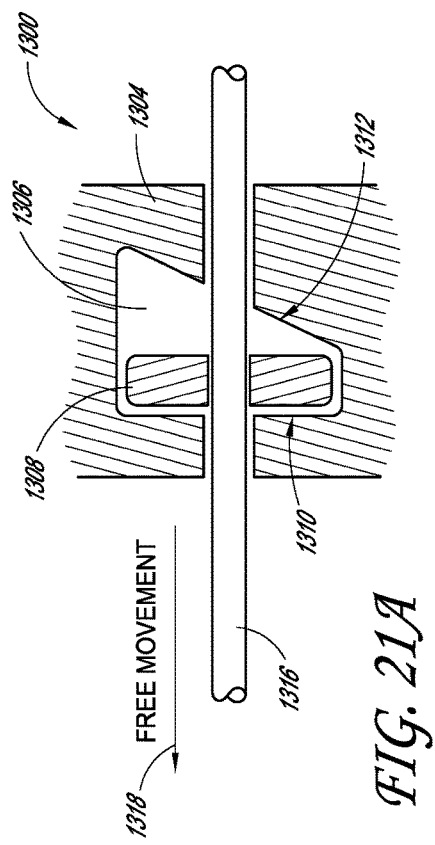
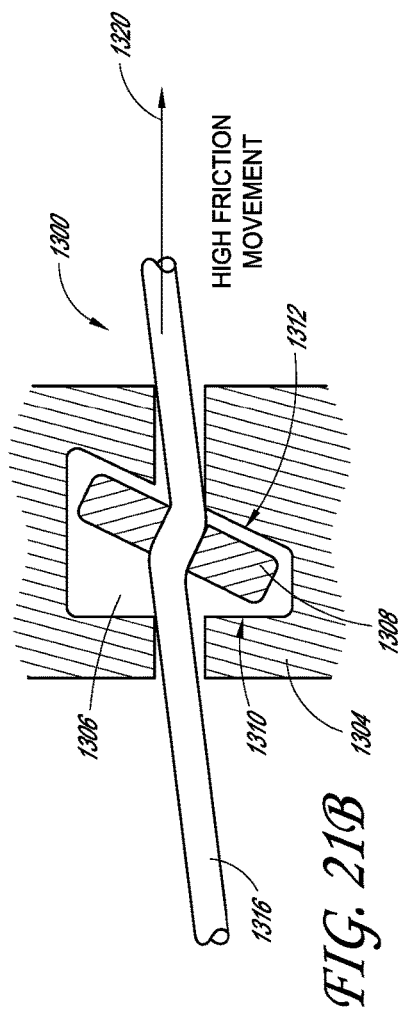
FIG. 21A
FIG. 21B

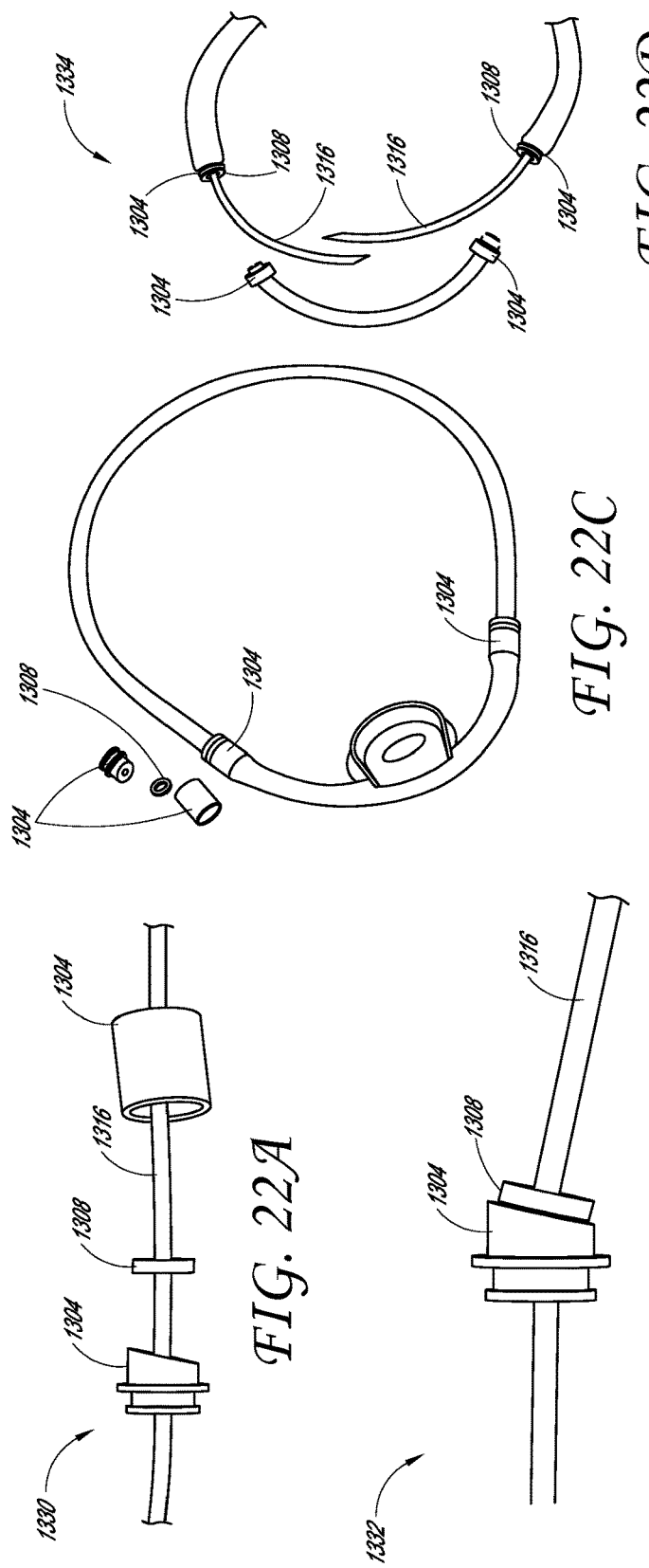

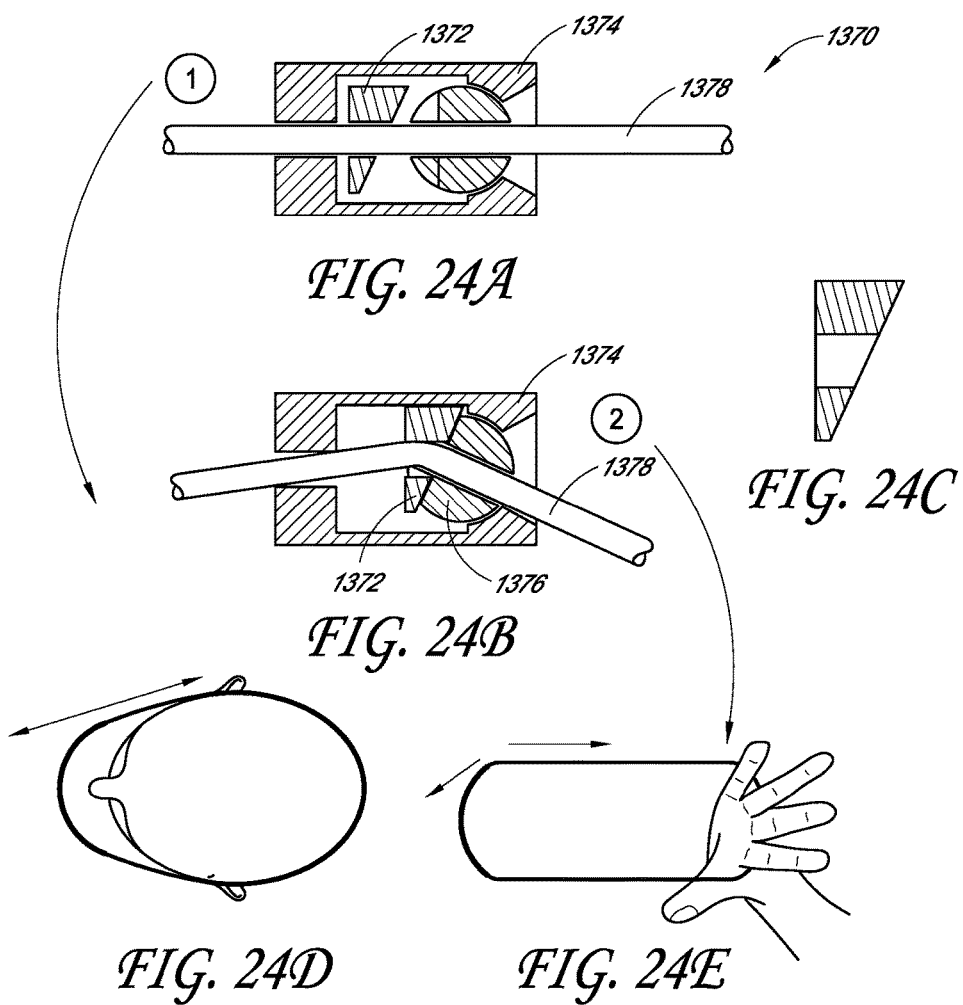

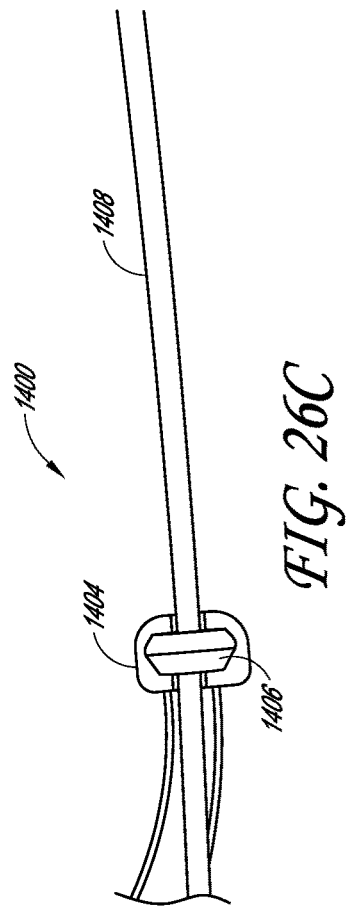
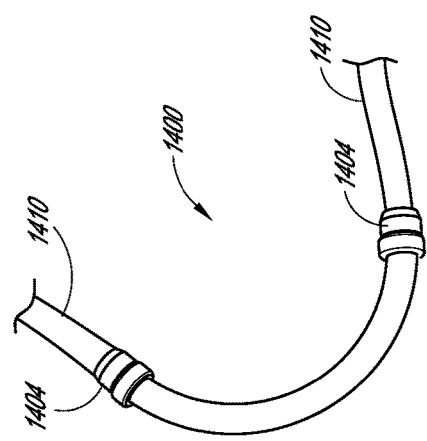
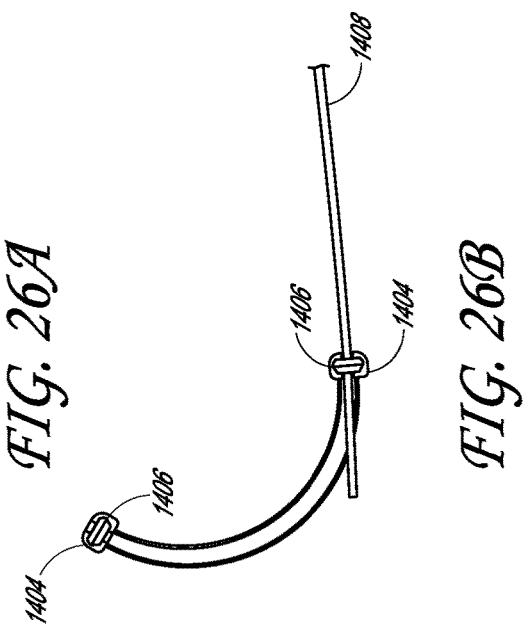

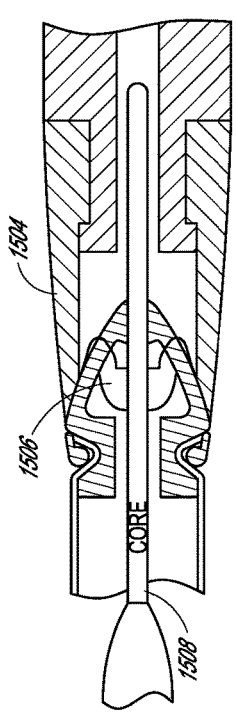
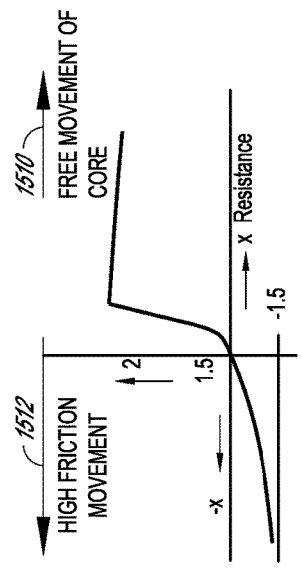
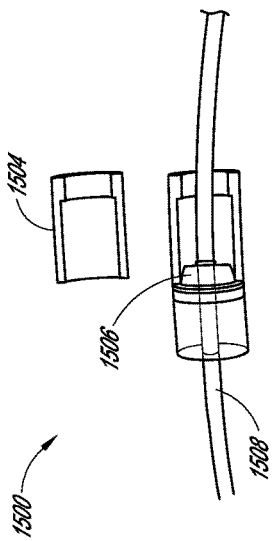
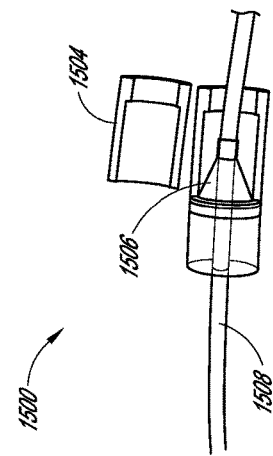
FIG. 27A
FIG. 27B
FIG. 27C
FIG. 27D

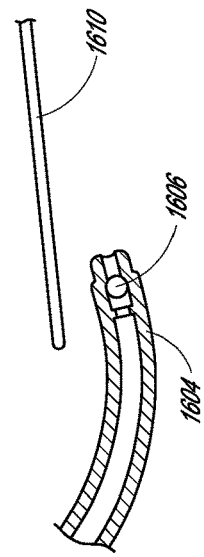
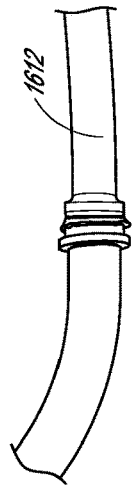
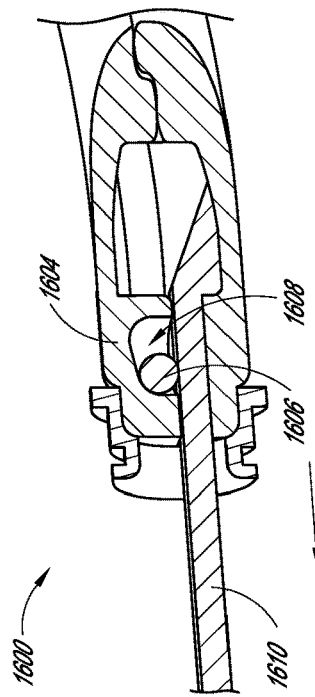
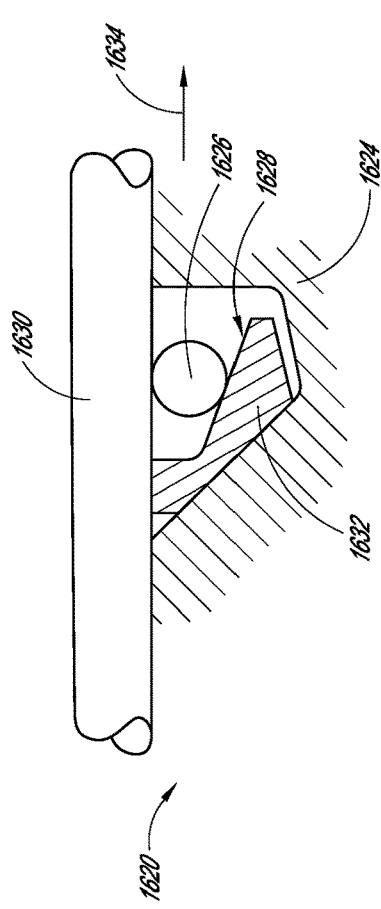
FIG. 28B
FIG. 28D
FIG. 28A
FIG. 28C

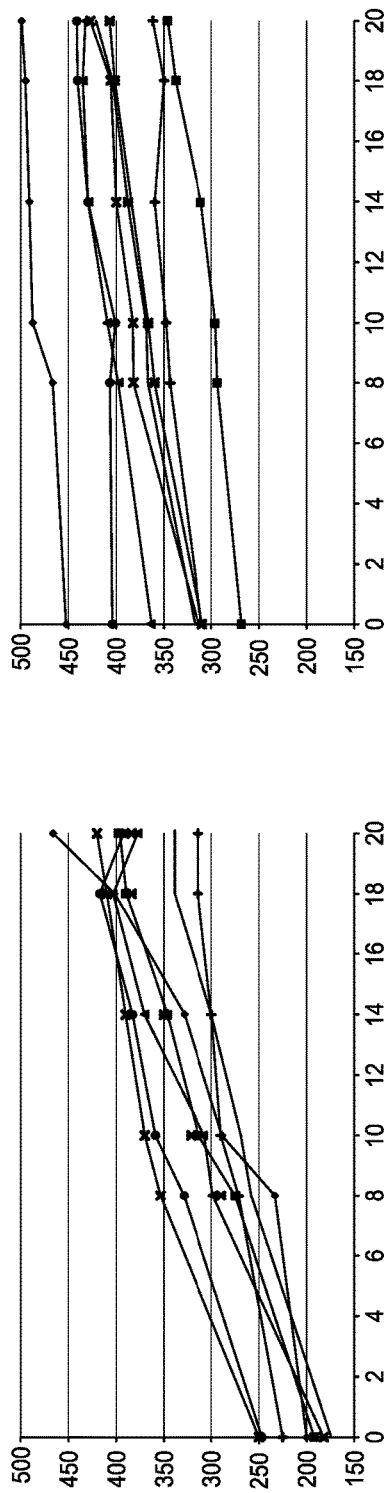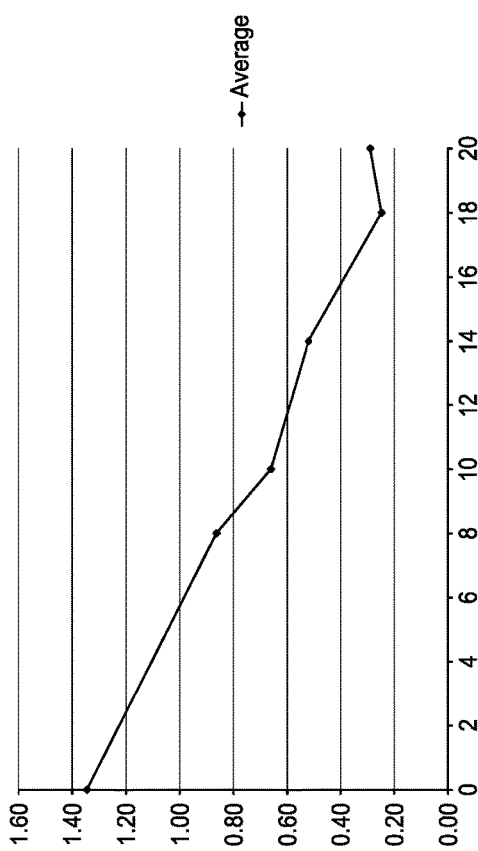
FIG. 31A
FIG. 31B
FIG. 31C

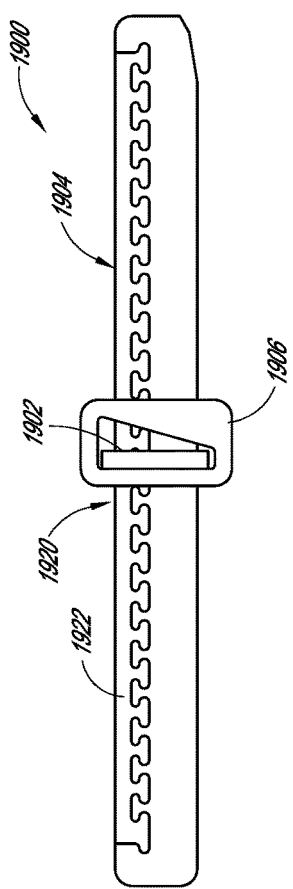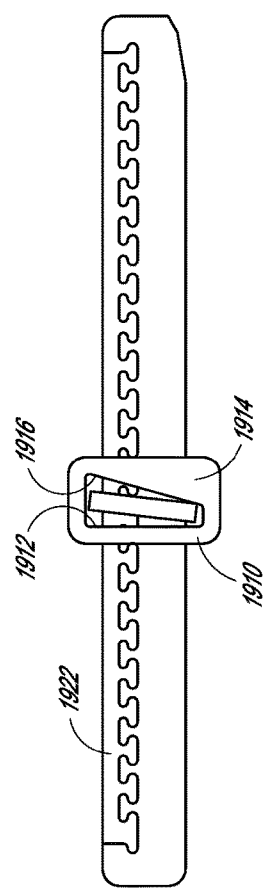

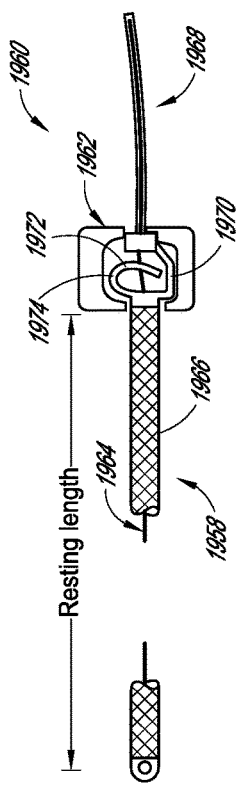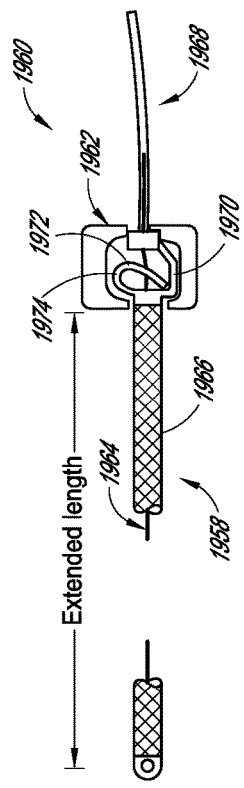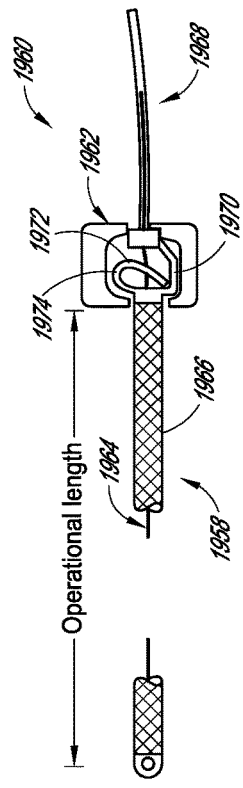

Relaxed State
-not extended

Fully extended

Site A
-Either side of the headgear

Site B
-In the mask frame attachment

AUTOMATICALLY ADJUSTING HEADGEAR FOR PATIENT INTERFACE

INCORPORATION BY REFERENCE TO ANY PRIORITY APPLICATIONS

Any and all applications for which a foreign or domestic priority claim is identified in the Application Data Sheet as filed with the present application, are hereby incorporated by reference and made a part of the present disclosure.

BACKGROUND OF THE INVENTION

Field of the Invention

The present invention generally relates to structures used to secure breathing mask interfaces to a head. More particularly, the present invention relates to generally automatically adjusting structures that have at least one of an adjustment mechanism and a configuration providing a predetermined wearing length and at least one longer length for donning.

Description of the Related Art

Obstructive sleep apnea (OSA) is a sleep condition in which the back of the throat relaxes so much while sleeping that it narrows the airway or even entirely blocks the airway. With the constriction or closure of the airway, breathing can stop or become very shallow for a few seconds or longer.

Continuous positive airway pressure (CPAP) is used to treat OSA. CPAP sends a flow of pressurized air that splints open the airway. The flow of pressurized air can be delivered to the user with a breathing mask interface. The breathing mask interface can include a mask and headgear, such as a non-elastic strap or an elastic strap.

When donning an interface having an elastic strap, the elastic strap is stretched to allow the headgear to slide over the head of the user. When released, the elastic strap tends to pull the interface against the face of the user.

When using the elastic strap, as the pressure within the mask increases (e.g., from about 4 cm H2O to about 12 cm H2O), the mask attempts to move away from the face of the user because the strap securing the mask against the face is elastic. The force that attempts to move the mask away from the face can be defined as the "blow-off force."

In some masks, when the blow-off force causes the elastic strap to stretch, the force exerted by the mask against the face of the user decreases. Thus, as pressures increase, leaks can result in those masks and, if suitably sealed at higher pressures (e.g., about 12 cm H2O), the elasticity of the strap causes undesirably high pressures to be exerted against the face of the user at lower treatment pressures (e.g., about 4 cm H2O) when the pressure is not at the higher pressure level. An interface having an adjustable, non-elastic strap can reduce the occurrence of leaks; however, such headgear are often over-tightened resulting in unnecessary forces being applied to the user's face and/or head.

Similar issues can occur in interfaces for treatments other than CPAP. For example, breathing mask interfaces are used in a hospital setting for non-invasive ventilation (NIV). Generally, NIV provides pressure ranges from about 20-50 cmH2O. Thus, the issues described above with respect to CPAP can be exacerbated in NIV treatment as a result of the greater difference between lower treatment pressures and higher treatment pressures. Another common respiratory disorder treatment is called Bi-level PAP, where the patient experiences an inspiratory pressure (IPAP) and an expiratory pressure (EPAP). The difference between IPAP and EPAP can vary from about 1 cmH2O to about 10 cmH2O, which also creates a cyclical blow-off force.

Elastic straps are also commonly used in combination with nasal cannulas for use in High Flow Therapy (HFT). HFT uses a cannula to deliver a high flow rate of respiratory gases, often including increased oxygen volumes.

A common problem experienced during the use of nasal cannulas is that of the gas supply tube being tugged on, dislodging the cannula prongs from the patient's nares, as a result of the headgear stretching. If the prongs are dislodged from the nares then loss of therapy can occur. Even without dislodgment, hose pull on the tube may result in the cannula sitting crooked on the patients face. This may cause discomfort to the patient and may provide the appearance of reduced effectiveness. Traditionally, cannulas have a lateral horizontal tube connection, which, when there is tension on the tube, can cause the cannula to pull away from the patient's nares in an uneven manner because the forces are transferred directly to one side of the cannula.

SUMMARY OF THE INVENTION

An object of the present invention is to provide an interface that will at least provide the industry and users with useful choice.

Some aspects of the present invention relate to providing an auto-adjusting mechanism that secures a breathing mask interface or other types of sealed or substantially sealed interfaces (e.g., nasal pillows) to a face of a user while achieving a balanced fit. As used herein, "achieving a balanced fit" means that the headgear will apply only enough force to overcome the "blow-off force" and, in some configurations, some or all of the anticipated hose pull forces or other external forces. The "blow-off force" may be defined as the CPAP pressure multiplied by the sealed area of the mask. With auto-adjusting mechanisms that achieve a balanced fit, there will be a minimal force exerted by the interface mask against the face of the user, which minimal level of force will maintain a sufficient level of force for sealing of the interface mask against the face of the user. Thus, user comfort can be increased. Preferably, once the interface assembly is fitted, any adjustments to remedy leaks can be accomplished by gently wiggling, pushing or pulling the mask interface rather than manipulating buckles, clips, straps or the like of the headgear assembly. When aspects of the present invention are applied to an unsealed or substantially unsealed interface, such as a cannula device, a "balanced fit" is achieved when the length of the headgear cannula loop matches the circumference of the user's head and provides some resistance to elongation. Because a cannula system is not pressurized, there is no "blow-off force" therefore the headgear only needs to hold the cannula in place and account for any anticipated hose pull forces. Adjustments can be achieved in the same manner as applications used with a CPAP mask or other pressurized or sealed interfaces.

The auto-adjusting mechanism combines some of the benefits of stretch and substantially non-stretch headgear assemblies while, in some configurations, removing any need for manual adjustment of the headgear assembly to suit the individual user. As used herein, "manual adjustment of the headgear assembly" means directly manipulating the headgear assembly to make substantial adjustments to the headgear assembly, such as a circumferential length defined by the headgear assembly.

Stretch headgear assemblies are known to be easy to fit because the stretch headgear assemblies can be elastically stretched to a length required to fit over a head of a user and then returned to a shorter length that fits to a circumference of the head of the user. Non-stretch headgear assemblies, on the other hand, only apply a minimum force required to secure the interface mask in position, which reduces or eliminates pre-loading that is caused when stretch headgear assemblies remain stretched to some degree while fitting to the circumference of the head of the user. In other words, in order to attempt to fit a large range of head circumferences, stretch headgear assemblies are designed such that, if a user has the smallest possible head circumference and the highest possible CPAP pressure, the stretch headgear assembly will provide sufficient force to secure the mask interface in position. Unfortunately, such a design will apply a significant force against a face of a user with the largest possible head circumference and the lowest possible CPAP pressure due to the preload that results from the extension of the stretch headgear assembly. For cannula systems, stretch headgear set ups are traditionally manually adjustable and/or designed to fit the smallest possible head circumference. This can result in multiple iteration adjustments for users and or tight fits for users with large head circumferences.

An aspect involves a headgear configured to elongate and retract to fit to a user's head, the headgear requiring a first load force to be applied to elongate the headgear and the headgear exhibiting a second load force when the headgear is fit to the user's head and is not elongating.

In some configurations, the first load force is larger than the second load force and/or an expected load force applied to the headgear during respiratory therapy. The expected load force can comprise a combined force comprising a CPAP pressure force and a hose drag force. The first load force can be greater than the expected load force by a reserve amount. The first load force can be greater than the expected load force throughout a range of elongation lengths of the headgear and/or the second load force can be smaller than the expected load force throughout the range of elongation lengths of the headgear.

An aspect involves a headgear for securing a mask to a user's face, the headgear comprising an elastic portion configured to provide a retraction force, a non-elastic portion configured to be inelastic in comparison to the elastic portion, and a restriction mechanism connected to the non-elastic portion and to the elastic portion, the restriction mechanism configured to require a first resistance force to permit elongation of the headgear and a second resistance force in response to retraction of the headgear.

In some configurations, the first resistance force is larger than the second resistance force. The first resistance force can be larger than a combined resistance force comprising a CPAP pressure force and a hose drag force. The second resistance force can be smaller than a combined force comprising a CPAP pressure force and a hose drag force.

An aspect involves a headgear configured to elongate and retract to fit to a user's head, the headgear having a first elongation resistance force in the absence of radial tensioning and a second elongation resistance force in response to radial tensioning.

In some configurations, the first elongation resistance force is smaller than the second elongation resistance force. In some configurations, the second elongation resistance force is developed by engagement of two portions of the headgear. The second elongation resistance force can be larger than a combined force comprising a CPAP pressure force and a hose drag force.

An aspect involves a headgear for securing a mask to a user's face, the headgear comprising an elastic portion configured to provide a retraction force, a non-elastic portion configured to be inelastic in comparison to the elastic portion, and a restriction mechanism connected to the non-elastic portion and to the elastic portion, the restriction mechanism configured to apply an elongation resistance force when the headgear is radially tensioned.

An aspect involves a patient interface system comprising an interface portion sized and shaped to surround the nose and/or mouth of a user and adapted to create at least a substantial seal with a face of the user. The system also includes a coupling that permits the patient interface system to be coupled to a gas delivery system. The system also includes a headgear system that allows the interface portion to be positioned and retained on a head of the user with the headgear system providing a transformational locking behavior with an ability to transform from an elastic type elongation behavior to a generally non-elongating type behavior when the patient interface system is in use.

In some configurations, the transformational locking behavior is provided by a mechanically based directional lock.

In some configurations, the headgear system provides the non-elongating type behavior in the range of about 0.5N to about 65N In some configurations, the transformational locking behavior is provided by a mechanical directional lock that comprises a lock enclosure, a movable lock member and a core member. A cross-sectional dimension of the core can be in the range of about 0.1 mm to about 8 mm. The lock member can be capable of moving relative to the core member through a range of angles between about 0° to about 45°. A biasing mechanism can act on the lock member and control the lock holding force. The directional lock can incorporate a friction promoter to facilitate lock activation.

In some configurations, the core member is a cord. In some configurations, the core member is a strap.

In some configurations, the transformational locking behavior is provided by a directional lock that uses mechanical adhesion, wherein the mechanical adhesion is provided through Van der Walls forces by using a nanofiber material.

In some configurations, the transformational locking behavior is provided by a directional lock that uses mechanical adhesion, wherein the mechanical adhesion is provided by a microstructure.

In some configurations, the elastic type elongation is provided by an elastic type elongation system comprising a fabric spring having an integrated elastic element. The fabric spring can be constructed as a braid where the elastic element and the non-elastic element are combined in such a manner that the non-elastic element provides a physical end stop to extension before the elastic element is plastically deformed. The amount of elastic element within the braid can be selected to achieve a desired force versus extension property of the fabric spring.

In some configurations, the transformational locking behavior is provided by a mechanical directional lock that comprises a housing, a movable lock member within the housing and a core member, wherein the housing guides movement of the core member, and wherein both the housing and the lock member are formed by a single integrated module.

In some configurations, the transformational locking behavior is provided by a mechanical directional lock that comprises a lock module, a non-elastic portion and an elastic portion, wherein the lock module, the non-elastic portion and the elastic portion form a modular adjustment assembly.

In some configurations, the interface portion is a mask and the modular adjustment assembly is connected to a frame of the mask. The frame can comprise one or more walls defining a space that receives the lock module.

In some configurations, the modular adjustment assembly is connected to a portion of the headgear system. The portion of the headgear system is a rear portion, which can comprise at least one of a lower rear strap and a crown strap.

In some configurations, the headgear system comprises a portion that passes on or below the occipital protuberance, which portion incorporates features that provide a non-uniform loading across the rear portion of the head.

In some configurations, the portion that passes on or below the occipital protuberance comprises an interrupted strap. The interrupted strap can comprise a first strap section and a second strap section connected by a coupling. The coupling can permit a relative motion between the first strap second and the section strap section. The relative motion can comprise rotational motion about a longitudinal axis of the interrupted strap.

In some configurations, the headgear system can comprise a portion that passes above the occipital protuberance, which portion incorporates features that provide a non-uniform loading across the top portion of the head.

In some configurations, the headgear system comprises a portion that passes on or above the occipital protuberance, which portion incorporates features that provide a non-uniform loading across the head.

In some configurations, the headgear system comprises a rear portion and at least one side strap on each side of the interface system that couples the rear portion to the interface portion. The at least one side strap can be coupled to the rear portion of the headgear system at a point located forward of and at or near an upper portion of the user's outer ear when in use. The rear portion of the headgear system can comprise an upper strap and a lower strap, wherein a rearward projection of the at least one side strap passes between the upper strap and the lower strap. The at least one side strap can comprise a pair of side straps arranged in a triangulated configuration.

In some configurations, the transformational behavior is provided by a lock mechanism that acts on one or more non-elongating elements contained within the headgear system to substantially isolate an elastic portion of the headgear system.

In some configurations, the headgear system incorporates a mechanism to enable a range of head sizes to be fitted, the mechanism comprising both elastic and generally non-elongating elements that are configured in parallel with each other.

In some configurations, the headgear system incorporates a mechanism to enable a range of head sizes to be fitted, the mechanism comprising one or more generally non-elongating elements substantially encircling the users head. In some configurations, a first portion of the non-elongating element overlaps with a second portion of the non-elongating element in a lengthwise direction of the headgear system. The first portion and the second portion can be first and second ends of the non-elongating element. The first portion and the second portion can be portions of one end of the non-elongating element.

In some configurations, the transformational locking behavior is provided by a manually operated lock, a pneumatically operated lock, an electrically operated lock, a piezoelectrically operated lock, a hydraulically operated lock or a thermomechanically operated lock.

In some configurations, the transformational locking behavior has a first lock stage that provides a first lock force and a second lock stage that provides a second lock force, wherein the second lock force is greater than the first lock force. In some configurations, the first lock stage can transform to the generally non-elongating type behavior with less elongation movement than the second lock stage.

An aspect involves a headgear for respiratory therapy configured to elongate and retract to fit to a user's head. The headgear requires a first load force to be applied to elongate the headgear. When the headgear is fit to the user's head, the headgear provides a balanced retention force that equals a load force applied to the headgear during respiratory therapy. The first load force is larger than the balanced retention force.

In some configurations, the load force applied to the headgear during respiratory therapy comprises a CPAP pressure force and a hose drag force. In some configurations, the first load force is larger than the load force applied to the headgear during respiratory therapy by a reserve amount. In some configurations, an elastic element applies a retraction force tending to retract the headgear. The retraction force can be less than the load force applied to the headgear during respiratory therapy.

The term "comprising" as used in the specification and claims means "consisting at least in part of". When interpreting a statement in this specification and claims that includes "comprising," features other than that or those prefaced by the term may also be present. Related terms, such as "comprise" and "comprises," are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

These and other features, aspects and advantages will be described with reference to various embodiments that are arranged and configured in accordance with certain features, aspects and advantages of the present invention, which embodiments are simply used to illustrated but not to limit the present invention.

FIGS. 2A, 2B and 2C are schematic drawings of three phases of headgear fit and adjustment. FIGS. 2D, 2E and 2F illustrate the force profiles associated with each of the three phases.

FIG. 3A is a schematic drawing of a first phase of headgear fit and adjustment. FIG. 3B illustrates a force profile associated with the first phase.

FIG. 5A is a schematic drawing of a third phase of headgear fit and adjustment. FIG. 5B illustrates a force profile associated with the third phase. FIG. 5C illustrates detail of FIG. 5B.

FIG. 6 is a graphic illustration of a force profile associated with headgear having a resistance on demand mechanism.

FIG. 7A is a schematic illustration of one embodiment of headgear having a resistance on demand mechanism.

FIG. 7B is an illustration of the embodiment of the headgear illustrated in FIG. 7A.

FIGS. 8A and 8B are schematic illustrations of a second embodiment of headgear having a resistance on demand mechanism.

FIG. 11B is a schematic illustration of elongation and retraction of the headgear shown in FIG. 11A.

FIG. 11C is an illustration of one embodiment of the headgear shown in FIG. 11A.

FIG. 11D is an illustration of a second embodiment of the headgear shown in FIG. 11A.

FIGS. 12A, 12B, 12C and 12D are schematic illustrations of a sixth embodiment of headgear having a resistance on demand mechanism.

FIGS. 13A, 13B and 13C are schematic illustrations of a seventh embodiment of headgear having a resistance on demand mechanism.

FIG. 14 is a graphic illustration of a force profile associated with headgear having a high resistance to start elongation mechanism.

FIG. 15A is a schematic illustration of one embodiment of headgear having a high resistance to start elongation mechanism.

FIG. 15B is a schematic illustration of a second embodiment of headgear having a high resistance to start elongation mechanism in a first position and FIG. 15C is a schematic illustration of the second embodiment of headgear having a high resistance to start elongation in a second position.

FIGS. 16A and 16B are schematic illustrations of a third embodiment of headgear having a high resistance to start elongation mechanism.

FIG. 21A is a schematic illustration of one embodiment of headgear having a large hysteresis mechanism shown with the mechanism allowing free movement.

FIG. 21B is a schematic illustration of the embodiment of headgear shown in FIG. 21A with the mechanism providing high friction resistance to movement.

FIGS. 22A, 22B, 22C and 22D are illustrations of one embodiment of the headgear shown in FIGS. 21A and B.

FIGS. 24A, 24B and 24C are schematic illustrations of a fifth embodiment of headgear having a large hysteresis mechanism. FIG. 24D is a schematic illustration of a headgear in an adjustment phase corresponding to FIG. 24A. FIG. 24E is a schematic illustration of a headgear in an application phase corresponding to FIG. 24B.

FIG. 26A is an illustration of one embodiment of headgear having a large hysteresis mechanism. FIG. 26B is an illustration of the headgear of FIG. 26A with the sheath and housings shown in section.

FIG. 26C is an enlarged illustration of a portion of the headgear shown in FIG. 26B.

FIG. 27A is a schematic illustration of a seventh embodiment of headgear having a large hysteresis mechanism.

FIG. 27B is an illustration of the embodiment shown in FIG. 27A in a retraction mode.

FIG. 27C is a second illustration of the embodiment shown in FIG. 27A in a mode restricting elongation. FIG. 27D is a graph showing a resistance force of the seventh embodiment of headgear.

FIG. 28A is a schematic illustration of an eighth embodiment of headgear having a large hysteresis mechanism.

FIG. 28B is an illustration of the embodiment shown in FIG. 28A.

FIG. 28C is a schematic illustration of a ninth embodiment of headgear having a large hysteresis mechanism. FIG. 28D is another illustration of the ninth embodiment.

FIG. 31A is a graphic illustration of the force applied to the user's head at various CPAP pressures by a headgear having one of the balanced fit mechanisms described herein.

FIG. 31B is a graphic illustration of the force applied to the user's head at various CPAP pressures by a headgear without one of the balanced fit mechanisms described herein.

FIG. 31C is a graphic illustration of the difference in force applied to the user's head at various CPAP pressures between headgear having one of the balanced fit mechanisms described herein and headgear without one of the balanced fit mechanisms described herein.

FIG. 40 is a side view of a directional lock that utilizes a flat strap and a lock plate carried by a housing. The lock plate is in a release position.

FIG. 41 is a side view of the directional lock of FIG. 40 with the lock plate in a lock position.

FIG. 46 is a side view of the directional lock arrangement of the interface assembly of FIG. 43 in a relaxed position.

FIG. 47 is a side view of the directional lock arrangement of FIG. 46 in an extended position.

FIG. 48 is a side view of the directional lock arrangement of FIG. 46 in an operational position.

DETAILED DESCRIPTION OF THE PREFERRED EMBODIMENTS

Figure 1:
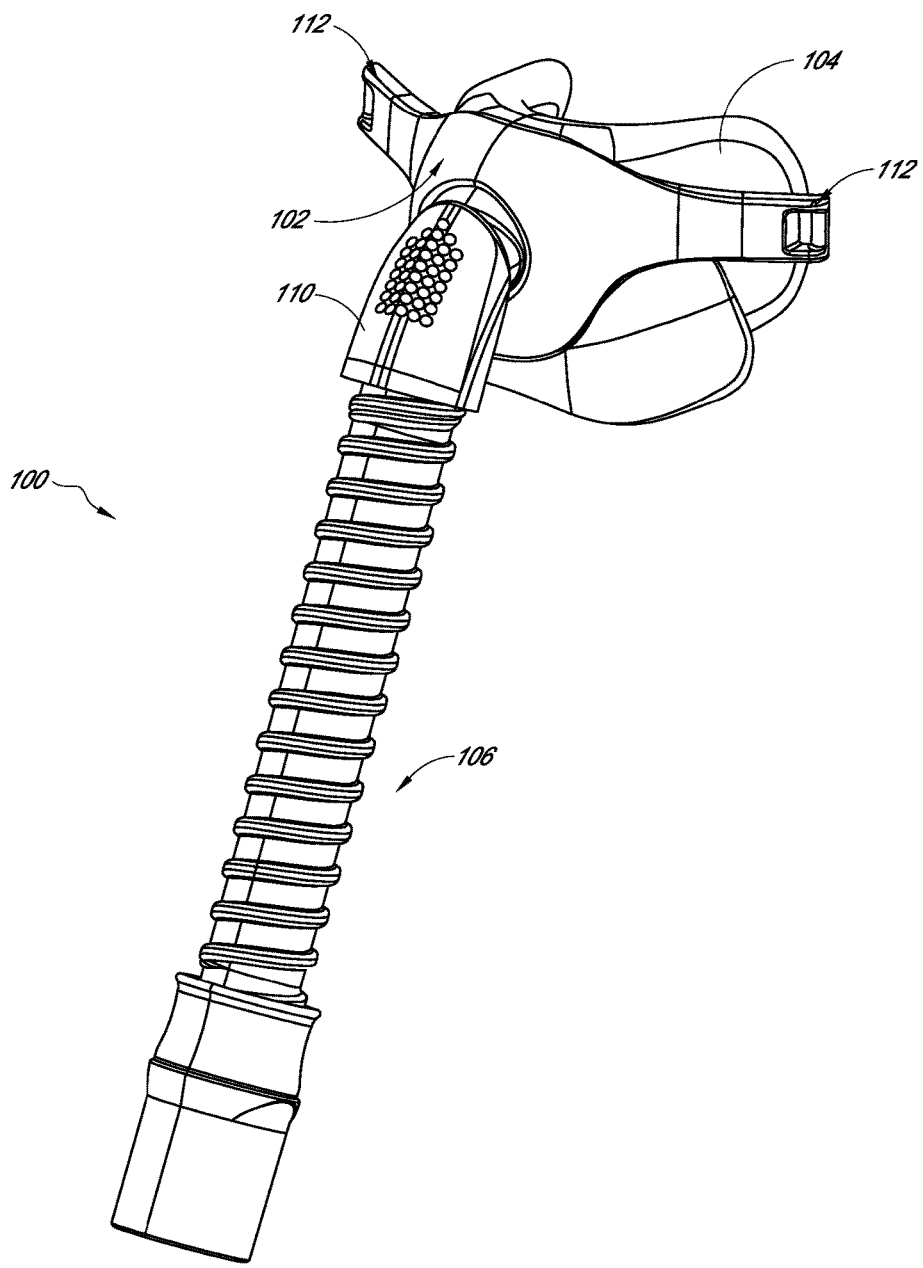
FIG. 1 is a perspective view of a user interface useable with headgear that is arranged and configured in accordance with certain features, aspects and advantages of the present invention.

With reference initially to FIG. 1, an interface assembly 100 is illustrated. The interface assembly 100 can have any suitable configuration. The illustrated interface assembly 100 is a nasal mask but, in some configurations, certain features, aspects and advantages of the present invention can be used with any type of interface, including but not limited to full face masks, nasal masks, nasal pillows, nasal-oral masks, oral masks and cannulas.

The illustrated interface assembly 100 generally comprises a frame 102 that supports a seal 104. The frame 102 and/or the seal 104 can be connected to a supply conduit 106. In some configurations, the supply conduit 106 can be connected to the frame with an elbow 110. The supply conduit 106 can be used to supply breathing gases to a user through the seal 104. The seal 104 or a combination of the seal 104 and the frame 102 can define a chamber that receives the breathing gases from the supply conduit 106.

The interface assembly 100 comprises mounting points 112. The mounting points 112 can be formed on at least one of the frame 102, the seal 104, the conduit 106 and the elbow 110. Any suitable mounting points 112 can be used to facilitate connection between the interface assembly 100 and one or more headgear assembly, which will be described below. In some configurations, the mounting points 112 facilitate easy connection and disconnection of the headgear assembly and the interface assembly 100. In some configurations, the headgear assembly and the interface assembly 100 can be joined together such that the headgear assembly is not generally removable from one or more component of the interface assembly 100. In some configurations, the headgear assembly and the interface assembly 100 can be integrally formed.

Figure 76:
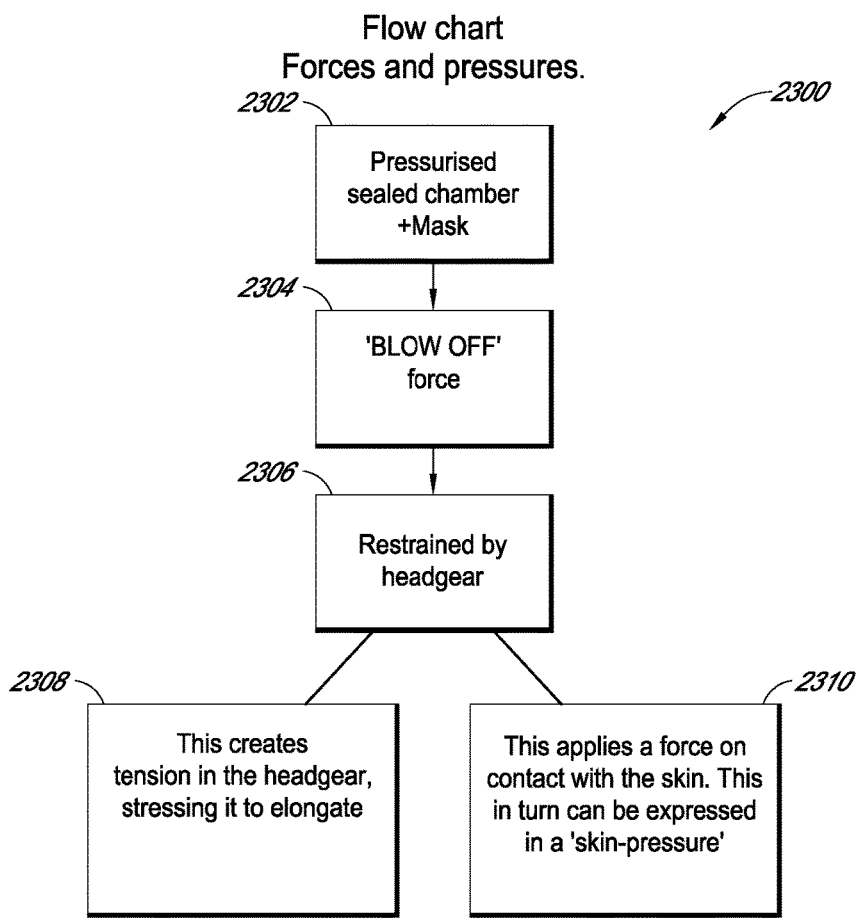
FIG. 76 is a graphical illustration of forces involved in certain types of respiratory therapy involving a sealed patient interface.

With reference to FIG. 76, a graphical illustration 2300 is provided to facilitate a description of forces involved in certain types of positive pressure respiratory therapy using a sealed patient interface. With respect to patient interfaces that seal on the face of the user, the interface (e.g., mask) in cooperation with the user's face creates a sealed chamber, as indicated in block 2302. Pressurized breathing gases are delivered to the sealed chamber, which generates a force tending to move the mask away from the user's face. This force is generally equal to the (projected) seal area multiplied by the positive pressure and is often referred to as the "blow-off" force, as indicated in block 2304. A function of the headgear is to restrain the mask in response to the blow-off force to keep the mask in equilibrium sealed against the face of the user, as indicated in block 2306. As indicated in block 2308, the blow-off force stresses the headgear in an attempt to elongate it, which places the headgear under tension. In addition, as indicated in block 2310, the headgear applies a force to the user's head over an area with which the headgear is in contact. The force applied to the contact area can be referred to as the "skin pressure" of the headgear. As the air pressure within the chamber defined by the seal 104 or the combination of the seal 104 and the frame 106 increases, the force applied by the headgear attempts to restrain the interface assembly 100 from lifting from the face. As such, the force applied by the headgear generally will increase to oppose the increasing force resulting from the increasing pressure within the mask. The blow-off forces will vary for different types and sizes of interfaces at any given pressure. Nevertheless, at lower pressures, or no pressure in the case of cannulas, less force is required to oppose the blow-off forces.

Accordingly, and as will be explained, the headgear assemblies described herein preferably can be designed to achieve a "balanced fit." In some configurations, the headgear assemblies generally comprise a stretch component (also referred to as elastic), a non-stretch component (also referred to as inelastic or non-elastic), a mechanism that restricts extension of the headgear, and a coupling that can join the headgear assembly to the mounting points 112, for example but without limitation. In at least some configurations, the balanced fit can be achieved by creating a substantially non-stretch path to resolve the stresses in the headgear when in use or in response to normal operational forces (e.g., blow-off and/or hose pulls forces, plus a reserve, if desirable). At higher forces than seen in use, the headgear can exhibit stretch-like behavior for donning. In some configurations, the headgear assembly may not include a stretch component. For example, the headgear could be manually extended and retracted. Various embodiments of the headgear will be described below.

The stretch components, when present, can have any suitable configuration. The stretch components can be any component that has a tensile modulus of less than about 30 MPa. The tensile modulus is the mathematical description of the tendency to be deformed elastically (i.e., non-permanently) along an axis when forces are applied along that axis; tensile modulus is the ratio of stress to corresponding strain when a material behaves elastically. In some configurations, the stretch component can be a coated, spun yarn material and the stretch component can include materials such as, but not limited to, rubber and spandex or elastane (e.g., LYCRA). In some configurations, the stretch component can be a strap or a combination of straps. In some configurations, the stretch component can be formed of a stretchable or elastic material. In some configurations, the stretch component enables the headgear to be expanded or lengthened and the stretch component also provides a retraction force that serves to contract or shorten the headgear. The contraction, or shortening, can occur as a result of the elastic properties of the stretch component. The contraction, or shortening, allows the headgear to more closely match the user's head circumference (plus the size of the mask). Generally, the headgear length is defined by a relaxed length and the headgear seeks to return to that length and it is this returning toward the relaxed length after elongation that is meant by contraction unless otherwise apparent.

The non-stretch components can serve as a stretch limiter. The non-stretch components can have any suitable configuration. In some configurations, the non-stretch components have a higher modulus of elasticity compared to the stretch components. The stretch components can be any component that has a tensile modulus of more than about 30 MPa. In some configurations, the non-stretch components restrict elongation of the headgear due to forces that are lower than a specified yield force. In some configurations, the yield point of the non-stretch material is higher than any anticipated loading to be applied to the headgear. In some configurations, the non-stretch components resist elongation of the headgear once the headgear has been fitted to the head. In some configurations, the non-stretch components resist elongation of the headgear once the headgear has been fitted to the head and the CPAP pressure has been applied to the mask. Thus, in some configurations, the non-stretch components (in some cases, in combination with the mechanisms discussed below) can thwart or resist elongation of the stretch components at least when CPAP pressure is applied. In the case of a cannula, the non-stretch components can resist the movement of the cannula under the influence of external forces, such as hose pull.

The mechanism can be any suitable mechanism that can limit expansion or elongation of the headgear when a force lower than a specified yield force is applied to the headgear. In some configurations, the mechanism operates without an effort by the user (e.g., the mechanism is automatic). That is, in at least some configurations, the mechanism can automatically move or switch to a mode in which extension or expansion is limited below the specified yield force. However, effort may be required for the user to don the mask, such as effort above the yield force to extend the headgear. In some configurations, the mechanism can apply a motion resistance force that can limit the extension or expansion of the headgear when a force lower than the specified yield force is applied to the headgear. In some such configurations, the motion resistance force can be a friction force. The specified yield force, that is, the force at which the headgear mechanism's motion resistance forces are overcome and elongation of the headgear becomes possible, may be determined by (1) the maximum blow-off force that is possible for the specific mask in use when a range of about 4-20 cmH2O pressure is anticipated and (2) a reserve to allow for any pulling of the CPAP hose and differences in user fit preferences. The reserve, generally defined as the difference between the lengthening or extension force and the maximum balanced fit force, can provide a buffer above the balance fit force, in which additional forces can be applied to the headgear without substantial elongation of the headgear occurring. The reserve force component can compensate for any additional force, such as hose pull, that may act to pull the headgear from the user's head. In some configurations, the motion resistance force can be applied to restrict extension of the headgear while releasing to allow retraction or contraction of the headgear. In some configurations, the mechanism can use one-way friction to lock or otherwise secure the headgear length. For example, the length can be secured using a frictional force that can only be overcome by a force that exceeds the blow-off force with minimal extension. Such mechanisms can be referred to herein as a directional locking arrangement or directional lock. The term "lock" as used herein is intended to cover mechanisms that secure the headgear length in response to certain forces, such as blow-off forces and/or hose pull forces. A "lock" does not necessarily secure the headgear length in response to all forces. Preferably, in some configurations, the retention force of the lock ("lock force") can be overcome, such as by manually-applied forces during the application portion of the fitment process.

As described above, the headgear can be stretched or extended to allow the mask to be fitted around the head of the user. The mechanism, while allowing the stretching or elongation of the headgear, also provides a means for locking the length of the headgear so that, when the CPAP pressure is applied, the seal is generally held in place and the headgear does not elongate substantially. In some configurations, a small amount of elongation may occur while the mechanism engages.

In some configurations, one-way friction headgear can incorporate a mechanism that is designed to give the user all the benefits of non-stretch headgear with the same ease of use experience as existing stretch headgear with little to no manual adjustment.

Stretching of the elastic headgear is typically not helpful in maintaining a seal. A mask that seals on the face will always result in a blow-off force and in turn a reaction force in the headgear. This force will stretch the headgear, affecting the fit of the seal. A stretching headgear must therefore be over-tightened to anticipate and compensate for this change, resulting in an unbalanced fit at lower pressures if a balanced fit is obtained at higher pressures without adjustments being made to the headgear.

The one-way friction mechanism can stop the non-stretch strap component of the headgear from changing its length when the seal is established. Once the CPAP machine is turned on and the seal is established, each user's variables, such as fit preference, face shape, etc. will create blow-off forces that attempt to push the mask away from the user's face. This blow-off force may be countered by a one-way friction mechanism that reduces or eliminates the likelihood of the non-stretch strap changing its length, resulting in a balanced fit over a range of pressures.

A mask that is sealed against the face is essentially a pressure vessel. The mask needs to be held against the face to maintain the airtightness and create a seal. The absolute minimum force required equals the (projected) seal area multiplied by the positive pressure. This force is the blow-off force as the direction points away from the face. To balance this force is the primary function of the headgear. A balanced fit is achieved when the reaction forces in the headgear substantially match the blow-off force. In a cannula embodiment, generally there is no seal between the patient and the cannula and thus there is no blow-off force. A balanced fit therefore can be achieved when the headgear assembly circumference matches the user's head circumference and provide some resistance to elongation or extension. For a cannula system, the self-fit headgear, as described herein, allows for a quick and easy fit without over tightening and excessive forces, which can occur with manually adjusted and elasticated headgears, respectively.

The projected seal area (even at the same given pressure) varies from person to person and depends on facial features and personal fit preferences. Consider the difference between a smooth-faced person and a more 'weathered' face. It is likely easier to make a seal on a smooth face, resulting in a smaller seal area and a lower corresponding blow-off force. Similarly, on the same person, at the same pressure, a seal can be made and maintained with a different fit, such as either a loose or tight fit. This is especially true with a mask having an inflatable seal. A loose fit will result in a smaller area and corresponding lower blow-off force.

With a balanced fit, the forces between the headgear and the user's head will be equal to the amount of force required to achieve the seal. CPAP features that vary the pressure throughout the night to give comfort to the user can complicate the situation when using standard headgear designs. The variations in pressure throughout the course of the night alter the amount of blow off force throughout the night. With headgear incorporating a balanced fit mechanism, the reaction forces drop in sync with the reducing CPAP pressure.

Hose pull is an additional force that is caused by the CPAP or cannula hose dragging when the user changes sleeping position. The hose dragging forces temporarily increase the force on the headgear. If the force exceeds the mechanism's resistance to elongation the fit will change which may result in leakage and/or discomfort.

As a user changes sleeping position while wearing the headgear described below, the headgear fit may be required to change. At this point, the natural interaction of pushing or wiggling the seal toward the face will result in the strap automatically retracting any excess length to maintain the new fit. In some situations, the mask or the seal may be pulled away from the face to cause the headgear to increase in length.

To remove the interface while wearing the headgear described below, the seal can be pulled forward with a force greater than the mechanism's maximum holding force. This causes the headgear to lengthen and which enables the seal to be pulled away from the face and over the user's head. Once removed, the lack of forces on the headgear will cause the headgear to automatically retract to its relaxed size.

In some configurations, the headgear applies a three phase force extension fit profile, an overview of which is shown in FIGS. 2A-2C. In the application phase 200, the headgear is stretched to go over the head of a user. The graph illustrates a resistance during elongation. The load curve 202 illustrates a steep rise in load for the initial extension of the headgear that then transitions to a generally constant, flat extension curve as the headgear is further stretched to accommodate larger head circumferences. In the adjustment phase 204, the headgear retracts and returns from a stretched condition until a desired fit is achieved. The load curve 206 shows an initial decrease in load as the headgear retracts to fit onto the user's head and also illustrates a low load force as the headgear further retracts to fit the user's head circumference. In the third phase, the balanced fit phase 208, the headgear adjusts to hold its position on the user's head as CPAP pressure is applied. The load curve 210 illustrates that a rise in load force of the headgear balances with the blow-off force due to the CPAP pressure and also resists additional forces, such as hose pull. In the case of a cannula embodiment, a balanced fit can be achieved at the end of phase two, and phase three typically will only be initiated if and when an external force, such as hose pull, is experienced. Further detail of the components of the balanced fit will be discussed below.

With reference now to FIGS. 3A-3B, additional detail of the application phase 200 and the related load curve 202 is shown. As discussed above, the load curve 202 illustrates a steep rise 220 because the headgear has initial resistance to stretch as it is stretched to accommodate the user's head. The initial resistance can relate to overcoming the resistance that will resist elongation. Once the load has reached a yield force of the mechanism of the headgear, the load curve transitions to a substantially flat, generally constant extension curve 222 as the headgear stretches further with little increase in load force for greater amounts of headgear extension.

Figure 4B:
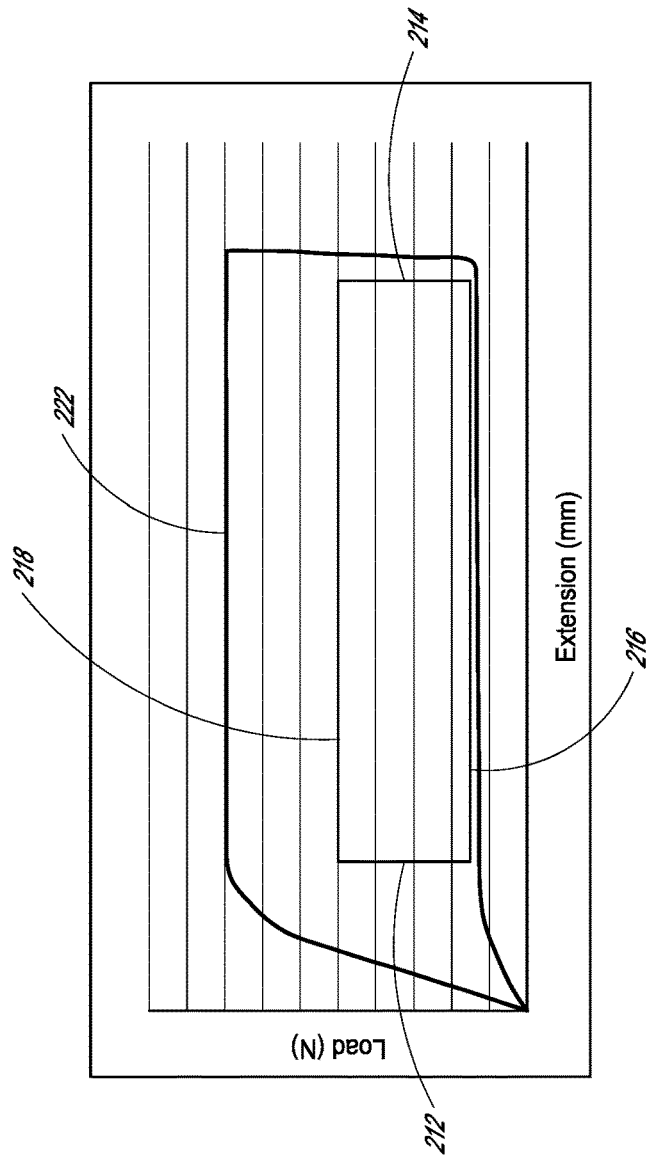
FIG. 4B illustrates a force profile associated with the second phase.
Figure 4A:
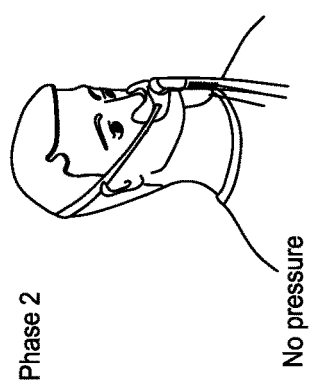
FIG. 4A is a schematic drawing of a second phase of headgear fit and adjustment.

FIGS. 4A-4B illustrate the second phase, or adjustment phase 204, in greater detail. In this phase, the headgear has been sufficiently stretched or elongated to fit over the user's head and the headgear has been released into position. Once a desired positioning has been achieved, the headgear returns from the stretched condition (e.g., over-elongated position) and the load force sharply declines 224, as shown in the load curve 206. After this reduction in force due to retraction of the headgear to fit the user's head, the load curve remains low 226 as the headgear remains fitted to the user's head. As illustrated, the headgear that typifies many features, aspects and advantages of the present invention features a first high load required to cause elongation and a second lower load at which the headgear contracts. In other words, the headgear contracts at a lower load than required to cause elongation and a hysteresis is the provided effect. In some configurations, the headgear has a delay in length change while the force changes dramatically when changing from an elongation mode to a contraction mode. In some configurations, the change in length of the interface circumference (including the headgear assembly) lags behind changes in load (i.e., force) when the interface length changes from elongation to contraction. Moreover, in some configurations, during elongation, as the force increases, the length increases more than the decrease in length during the decrease in force (e.g., the slope is lower at 220 than at 224).

In FIGS. 5A-5C, a balanced fit is achieved in the balanced fit phase 208, in which the force of the headgear balances the blow-off force of the CPAP pressure. As mentioned above, the headgear adjusts to hold its length as CPAP pressure is applied. The load curve 210 illustrates the rise in the load force that balances the blow-off force. As shown in the detailed balanced fit section 230 of the load curve 210, the balanced fit produces a higher load than the retraction force 226 of the headgear. The balanced fit component is the increasing force in the strap of the headgear that provides an equal and opposite force to the blow-off force. However, this force is also lower than the lengthening or extension curve 222. In some configurations, the slope of the balanced fit section 230 is related to, influenced by, or can be substantially the same as the rise 220 and/or the decline in the load force 224 during retraction of the headgear. In some configurations, the slope of the balanced fit section 230 is steeper than the slope in the decline in the load force 224. In some configurations, the slope of the balanced fit section 230 is greater than the slope in the initial rise 220 during lengthening of the headgear.

A reserve force component 232, defined as the difference between the lengthening or extension force 222 and the instantaneous or current balanced fit force 234, is a buffer above the balance fit force, in which additional forces can be applied to the headgear without substantial elongation of the headgear occurring. The reserve force component can compensate for any additional force, such as hose pull, that may act to pull the headgear from the user's head. As external forces, such as hose pull, rise so do the reaction forces in the headgear. Only if the external forces surpass the yield point will the headgear elongate, which can result in leaks. The reserve component preferably is large enough to accommodate a realistic external force that could be applied to the mask by the hose being pulled on during normal use. This reserve component or buffer also allows for the user's preference in engagement of the seal of the mask with the user's face, such as a tighter or looser fit. When used with a cannula system, the whole of phase three can be allocated to reserve force. Because there is no blow-off force, a balanced fit can be achieved at the end of phase two and, thus, phase three typically only needs to account for any external forces, such as hose pull, and user preference in terms of tightness of fit. As a result, the yield force for a cannula set-up can be substantially lower than for a CPAP set-up. In general, the force within the headgear when a balanced-fit is achieved can also be lower for a cannula set-up than a CPAP set-up.

The graphs of FIGS. 3-5 also include a perimeter that surrounds and defines an area. The illustrated perimeter is generally rectangular in shape and represents an operating envelope of an interface assembly as it relates to head circumference of the user (extension) and force applied by the CPAP system (load), which could, but does not necessarily, include external forces, such as hose pull. A length of the area along the x-axis or a distance between a left end 212 and a right end 214 of the perimeter represents the desired or usable range of user head size. That is, the left end 212 is located at a lower head size (circumference or extension) and the right end 214 is located at an upper head size. The lower and upper head sizes can be minimum and maximum head sizes for a particular interface assembly, which can be a universal fit or intended for a certain subset of head sizes (e.g., small, medium, large) or users (e.g., infant, adult).

A length of the area along the y-axis or a distance between a lower end 216 and an upper end 218 of the perimeter represents the desired or usable range of force or load that is applied the interface assembly in use. The lower end 216 of the perimeter is located at a lower force (e.g., force resulting from a low CPAP value) and the upper end 218 of the perimeter is located at an upper force (e.g., force resulting from a high CPAP value). As with head sizes, the lower and upper forces can be for CPAP systems or protocols in general or can be for a specific subset of CPAP systems or protocols. As described above, the force range can be based on CPAP forces alone, or can include external forces, such as hose pull forces, for example. Preferably, the instantaneous or current balanced fit force 234 falls within the operating envelope.

For a stretch or elastic system to offer sufficient performance across the operating envelope, the system must provide a greater resistance force than the interface assembly can generate via one or both of CPAP pressure forces and external forces. Thus, the force-extension curve of the stretch or elastic system should be positioned above the operating envelope and, if necessary, spaced above the operating envelope by a distance sufficient to address external forces and/or provide a reserve to address unusual or unexpected forces. Accordingly, stretch or elastic systems apply a force to the user that is at a greater level than necessary to address the actual forces applied to the interface assembly (e.g., CPAP and external forces). This greater-than-necessary force tends to result in reduced comfort for the user.

Different force profile configurations are possible for the headgear assembly, with the force profile configurations preferably including a balanced fit region. The force profiles described herein are applicable to both CPAP and cannula systems; however, the point at which a balanced fit is achieved will usually differ. The force levels associated with maintaining the fit of the interface generally will also be significantly lower in cannula systems. In addition, some or all of the headgear embodiments will work, or could be modified to work, for a cannula system wherein a balanced fit is achieved when the headgear circumference matches the head circumference and, preferably, some amount of resistance to extension of the headgear is provided. Increasing CPAP pressure and/or blow-off forces generally will correlate to an external force being applied to a cannula system. FIG. 6 illustrates one force profile 240 in which resistance of the headgear strap results on demand. This configuration requires the least effort to extend and fit the headgear. In this configuration, the user only has to overcome the elasticity of the headgear, as illustrated by curve 242, which typically requires a force of less than about 1.5N. The balanced fit component of this configuration, illustrated by the curve 244, provide an equal and opposite force to the blow-off force and also compensate for any additional external forces that may act to pull the headgear from the user's head. The curve 246 adds a buffer in addition to the balanced fit portion 244.

FIGS. 7A-B illustrate one embodiment of headgear that has the resistance on demand profile shown in FIG. 6. The illustrated configuration comprises a layered stretch assembly 304. In the layered stretch embodiment 304 shown in FIG. 7A, two straps 306 and 308 can be layered, one on top of the other, each with alternating stretch 310, 316, 320 and non-stretch 312, 314, 318 sections. As shown, the two straps 306 and 308 may be folded over one another, as indicated by the arrow 324 such that the non-stretch section of one strap overlaps with at least the stretch section of the other strap. As shown, the non-stretch segment 314 of the strap 306 overlaps the stretch segment 316 of the strap 308. The non-stretch segment 314 is preferably longer than the stretch segment 316 such that at least a portion of the non-stretch segment 314 overlaps with at least a portion of the non-stretch segment 312 to create a continuous non-stretch path. Similar overlap of the non-stretch segment 312 with the non-stretch segment 318 is also shown. In addition, the straps 306 and 308 can have a form of "grip," such as rubber webbing or other tacky substance, on the non-stretch sections. When positioned on top of each other as indicated by the overlapping grip section 322, the grip sections overlap and catch, reducing or eliminating the likelihood of further elongation of the headgear straps until the motion resistance force between the straps is exceeded. Once the headgear is placed on the user's head, the radial force between the stretch and non-stretch layers causes the grip sections to engage and form a complete non-stretch section, limiting further elongation of the headgear straps. FIG. 7B shows two photographs of the layered strap embodiment shown in FIG. 7A.

Another embodiment of a layered stretch strap configuration is shown in FIGS. 8A and 8B. The layered grip strap configuration 400 is composed of two straps, one having a grip pattern in one or more locations, and the other strap having a series of alternating stretch segments or sections 414 and non-stretch segments or sections 412, 416, as in the configuration shown in FIG. 7A. Although one stretch and two non-stretch segments are illustrated, other numbers of stretch and non-stretch segments could be provided. A first or inner strap 406 is shown with two grip pattern segments 410 located on either end of the strap 406; however, different numbers of grip pattern segments 410 can be provided, including a grip pattern along substantially an entire length of the strap 406. The grip segments 410 overlap with the non-stretch segments 412, 416 of a second or outer strap 408 to provide an interactive gripping section that selectively couples at least a portion of the straps 406, 408. However, this arrangement could also be reversed between the inner strap 406 and the outer strap 408. In some configurations, the inner strap 406 is a non-stretch member, which allows the headgear to form a complete non-stretch section when the straps 406, 408 are coupled, limiting further elongation of the headgear, as discussed above. However, in other configurations, the inner strap 406 can be constructed from an elastic or stretchable material. In such configurations, the headgear includes a stretch section even when the straps 406, 408 are coupled, a length of which can be defined by the elastic portion 414 of the outer strap 408. Preferably, the stretch section is provided at the back of the user's head and non-stretch sections are located on the sides of the user's head. Positioning the stretch section at the back of the user's head can result in less stretch movement for a given force than a stretch section provided on the side of the user's head. When the headgear is loaded, such as a result of blow-off forces or external forces, the section of at the back of the user's head is pulled against the user's head thereby increasing friction between the headgear and the user's head. In some configurations, the friction can be sufficient to substantially prevent stretch movement of the stretch section of the headgear. Features to enhance friction between the headgear and the user's head can be employed, such as silicone or other types of grip elements, for example. The stretchable inner strap 406 can facilitate stretching of the headgear prior to donning. In some configurations, such as when a substantial entirety of the inner strap 406 is stretchable, the material of the section(s) 414 of the outer strap 408 has a substantially lower elongation modulus compared to the material of the inner strap 406 to address the length of the stretch section(s) 414 being substantially less than the length of the inner strap 406. The inner strap 406 may be a thin strap with the gripping pattern applied to one or both sides of the strap 406. The strap 408 can have a similar gripping pattern applied to the non-stretch segments 412 and 416. In some configurations, the gripping pattern is applied on the portion of the strap facing away from the user. In the illustrated configuration, the second strap 408 may have a slot in which the inner strap 406 fits in order to retain alignment of the straps and for ease of use of the headgear assembly. For example, the second strap 408 may comprise a passage through which the first strap extends. The passage can be formed along a majority of a length of the second strap or the passage can be defined by multiple loops (e.g., similar to belt loops used on clothing).

Figure 9:
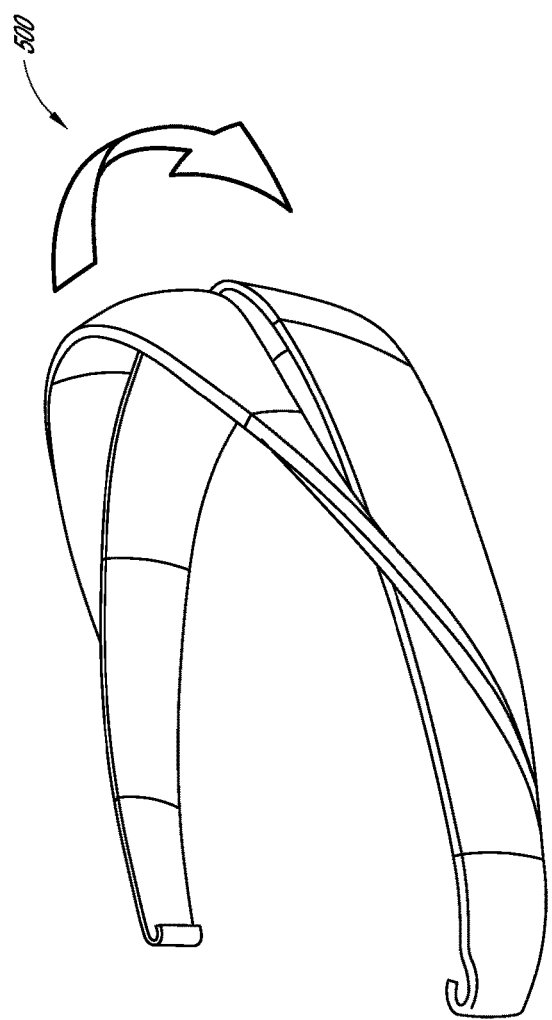
FIG. 9 is a schematic illustration of a third embodiment of headgear having a resistance on demand mechanism.

FIG. 9 illustrates a third embodiment of a layered strap configuration. In this configuration, the layered strap 500 comprises alternating stretch and non-stretch segments, as in the embodiments discussed above. In the configuration illustrated in FIG. 9, a segment of the strap folds over. When folded over, gripping portions of the non-stretch segments can be aligned, which reduces or eliminates the likelihood of further elongation of the headgear. In some configurations, the strap segment is folded over once the headgear has been stretched to fit over the user's head and after the user has achieved a desired tension in the interface assembly. In some configurations, the strap segment is folded over prior to initiation of pressure-based treatments.

Figure 10:
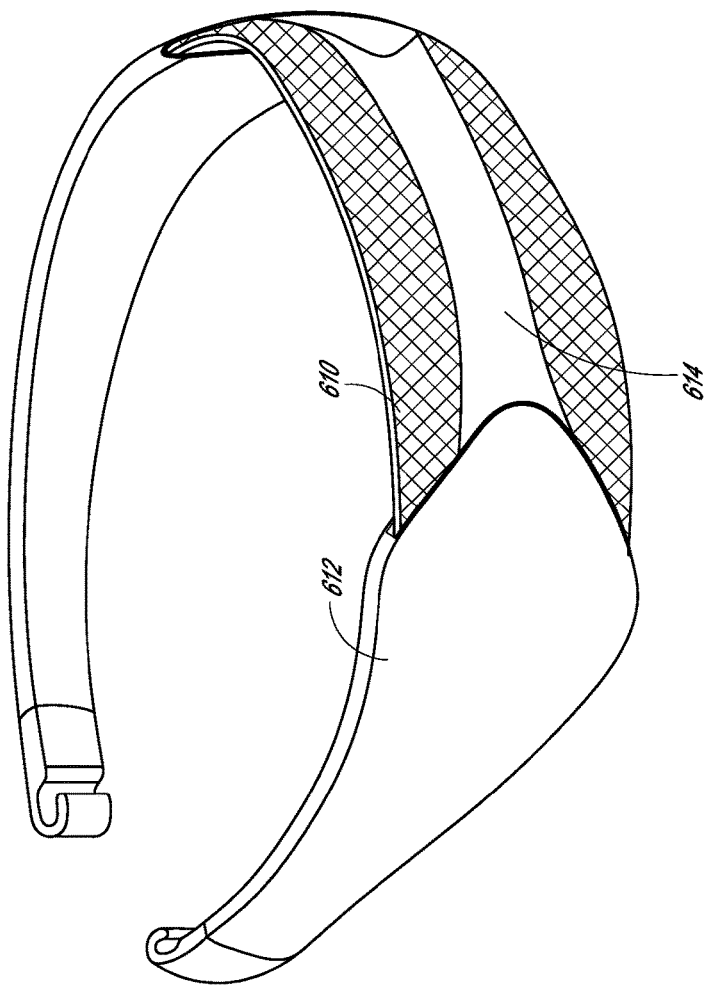
FIG. 10 is a schematic illustration of a fourth embodiment of headgear having a resistance on demand mechanism.

An additional layered strap configuration is shown in FIG. 10. In this configuration, the layered strap 600 has a stretch segment 614 layered over a non-stretch segment 610. The stretch segment 614 connects two non-stretch segments 612 (one shown) that overlap with the non-stretch segment 610 as shown. The non-stretch segments 612 may take the form of a wrapped segment or a loop or pocket through which or into which the central or rear non-stretch segment 610 can be inserted. As discussed above, each non-stretch segment may have gripping portions that, when aligned, reduce or eliminate the likelihood of further elongation of the headgear.

When a force is applied to attempt to elongate headgear having a resistance on demand force profile, such as the non-stretch path headgear shown in FIGS. 7A-B and 8-10, there are minimal forces applied between the two strap layers except in the location where the headgear is being held. Accordingly, the grip sections do not interact with each other and the stretch components are able to elongate without substantial resistance. When the headgear is released from an elongated position, the stretch components relax until the headgear substantially matches the user's head circumference. At this point, the non-stretch components and the grip sections on the two strap layers should be overlapping. The radial force applied by the user's head on the headgear can cause the grips to interact with each other and lock the length of the headgear, limiting further extension or retraction without the application of substantial force. The interaction of the grips and the overlapping stretch/non-stretch sections creates a continuous non-stretch path through the headgear. This path limits further elongation of the headgear when the CPAP pressure is applied. The headgear applies an equal and opposite force to the CPAP pressure applied on the user's face, thus creating a balanced fit. In order to adjust the fit of the mask, the interaction of the gripping sections can be released or diminished.

Figure 11A:
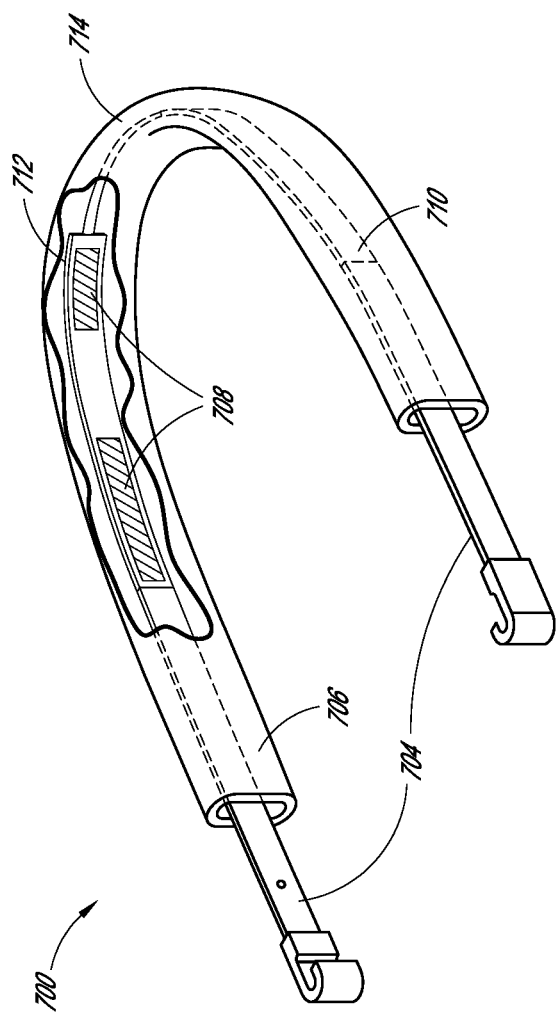
FIG. 11A is a schematic illustration of a fifth embodiment of headgear having a resistance on demand mechanism.

Another resistance on demand configuration may be seen in FIGS. 11A-D. With reference to FIG. 11A, in this configuration, a tunnel strap configuration 700 has two relatively non-stretch strap segments 704. In some configurations, the non-stretch strap segments can be formed of thermoformed compressed material such as Breath-o-Prene. Each strap segment 704 can be connected to a flexible shuttle 712. Each flexible shuttle 712 can be connected to the segments 704 and to a low force elastic member 714. The flexible shuttles 712 and elastic member 714 can be generally surrounded by a curved head-shaped tunnel 706 with a smooth inner surface made of a soft, non-stretch (at least in circumference/length) material. A number of non-slip pads 708 (two shown) may be located on the surface of the shuttles 712 closest to the user. The non-slip pads may be made from silicone or another non-slip or tacky material. One end of each of the shuttles 712 can be aligned with the ends of the elastic member 714 so that the elastic sits on top of the entire length of each shuttle 712. The layered elastic 714 and shuttle 712 configuration can be attached end on end to the relatively non-stretch strap segments 704. The strap assembly can be housed inside the tunnel although, in other configurations, the tunnel could have one open side.

The flexible shuttles 712 provide the gripping force that establishes the balanced fit of the headgear. As shown in FIG. 11B, the shuttle 712 changes shape depending on the elongation or retraction of the strap and the amount of force applied. When the strap 704 is pulled, the shuttle 712 conforms to the shape of the tunnel 706 and grips, reducing or eliminating the likelihood of further elongation of the headgear. When the strap 704 is released, or is retracting, the shuttle 712 peels away from the surface of the tunnel 706 and breaks the grip, allowing the strap to retract. FIGS. 11C and D provide further illustration of one embodiment of the tunnel concept 700 shown in FIGS. 11A and B. FIG. 11C shows the tunnel strap configuration by itself, while FIG. 11D shows another embodiment of the tunnel strap configuration attached to a mask. In FIG. 11D, a second strap is shown. The second strap (or set of straps) can be positioned below or above the tunnel 706 and/or the strap 704. In some configurations, the second strap can be connected to the strap 704. The second strap can be grabbed by the user and, as such, can be a handle during donning or doffing of the headgear. In some configurations, the second strap helps to orient the headgear during donning. In some configurations, the second strap may be positioned generally below the maximum occipital point.

An additional resistance on demand configurations is shown in FIGS. 12A-12D. In this configuration, another tunnel strap configuration 800 has a tunnel 802 that is configured to expose two shuttles 804 to allow some manual interaction and fit adjustment. By exposing the shuttles 804, the user could have additional control over the initial fit of the headgear. Tabs 806 (one shown) also can be configured to provide a convenient way for the user to adjust the fit of the headgear. In some configurations, pulling the tabs can shorten the strap, for example. In some configurations, the tabs 806 can be disposed near the ends of the tunnel 802

When a force is applied to elongate headgear having a tunnel mechanism and exhibiting a resistance on demand force profile, such as the headgear shown in FIGS. 11A-D and FIGS. 12A-12D, the elastic member elongates freely until a radial force is applied to the mechanism. Until the radial force is applied, the axial force applied only needs to be great enough to overcome the strength of the elastic strap. When the headgear is released from an elongated position, the elastic strap retracts until the headgear matches the user's head circumference and a radial (e.g., transverse to the strap) force then is applied. At this point, the user's head will be applying the radial force to the headgear. The radial force, combined with the curvature of the tunnel, will cause the non-slip pads on the back of the shuttle to come into contact with the internal wall of the tunnel, forming a grip and locking the length of the headgear, limiting further elongation or retraction. Since the shuttle is preferably a flat piece of plastic, its natural reaction is to sit at a tangent to the curve of the user's head. This results in the front end of the headgear, where the elastic is permanently attached, having a predisposition to sit away from the internal wall of the tunnel, releasing the non-slip pads when there is minimal radial tension applied to the headgear. The friction between the non-slip pads and the tunnel is typically not enough to prevent the elastic member from retracting in the tunnel.

When a tension force is applied to the headgear by the application of CPAP pressure, the front of the shuttle is pulled into contact with the internal wall of the tunnel. The shuttle is pulled into contact with the internal wall of the tunnel. In this configuration, the non-slip pad interacts with the tunnel, increasing the force required to elongate the headgear as the tensile forces applied to the headgear increase. This effectively locks the length of the headgear, limiting further elongation and retraction unless a force greater than the specified applied force is applied.

FIGS. 13A-13C illustrate yet another embodiment of a resistance on demand configuration. In this configuration, an air activated lock strap 900 provides a balanced fit headgear. One or more air activated lock assemblies 902 can be provided with one on each side of the mask 914. The air activated lock assembly can be connected to, or positioned within or along, an elastic strap or the like. In some configurations, the elastic strap can be connected to the mask, the seal of the mask and/or the frame of the mask. In some configurations, the elastic strap can be connected to the air activated lock. Each air activated lock assembly can have an air activated lock 904 encased by a lock casing 906. A supply air tube 908 runs from the mask 914 to each air activated lock assembly 902. An enlarged view 910 of one of the air activated lock assemblies 902 illustrates that the core strap 912 runs through the middle of each air activated lock assembly 902. As discussed above, the holding force of the headgear is only required in the presence of CPAP pressure. In this embodiment, the air pressure to maintain the air activated locks is provided from the air pressure from the mask. When the air activated lock assembly 902 is activated to provide holding force for the headgear, such as after a fit has been achieved, air is supplied to each air activated lock 904 from the mask 914. This air pressure causes the air activated lock 904 to expand and grip the core strap 912, reducing or eliminating the likelihood of further elongation of the headgear strap. Because the air lock assembly 902 is in fluid communication with a chamber of the mask, as the pressure increases in the mask, the pressure increases in the air lock assembly 902. As such, when the forces increase trying to lift the mask from the face, the forces that oppose elongation of the strap also increase. This resistance on demand embodiment generally is not applicable to a cannula set-up. This is because the air locks require the presence of air pressure in order to be activated and, generally, an unsealed cannula system is not capable of providing this. An external air pressure source, that is manually activated, can be provided to the air locks to provide the holding force required to prevent elongation of the headgear due to external forces.

FIG. 14 illustrates a second force profile incorporating a balanced fit. In this figure, a high resistance to start movement profile 250 is shown. Headgear configured with this force profile can have a locking mechanism that gives way at a predetermined force. The load force will remain low as the headgear is elongated to fit over the user's head and retracts for fit until force is again applied to elongate the headgear strap. As illustrated, the load-elongation curve 252 can have an initial upward slope at low extension that illustrates the high resistance to an initial elongation of the headgear. After a predetermined force has been reached, a much lower amount of force is required to further elongate the headgear. As in the resistance on demand force profile discussed above, the high resistance to start elongation movement force profile also includes a balanced fit having two components. First, the balanced fit component 254 provides a high resistance to further elongation over a small range of extension to counteract the blow-off forces of the CPAP pressure. Additional resistance to extension is provided by the reserve component 256 that counteracts any external forces, such as hose pull, that may act to elongate or loosen the headgear. In the illustrated configuration, the slope of the initial elongation portion of the curve is substantially the same as the slope of the balanced fit component 254 of the curve. In some configurations, because the slopes of the initial elongation portion and the balanced fit portion of the curve result from attempting to overcome the same mechanism in FIG. 14, the slopes will be the same or substantially the same.

One embodiment of a configuration that incorporates a high resistance to start elongation profile is shown in FIGS. 15A-B. FIG. 15A illustrates a cross-section of a roller ball lock mechanism 1000. In this configuration, the locking chamber 1002 includes a roller ball 1004 and a switch 1006. The switch 1006 may be a wedge-shaped member having a top surface 1012 that lies adjacent to an upper inner surface of the locking chamber 1002 when the switch is engaged with a core strap 1010. When the switch 1006 is engaged with the core strap 1010, as shown in FIG. 15A, friction between the roller ball 1004 and the core strap 1010 substantially prevents further elongation of the core strap 1010. At a predetermined force, the roller ball 1004 and the switch 1006 change position with the switch 1006 pivoting around the pivot point 1008 to release the core strap 1010 and allow the core strap 1010 to move freely in either direction, allowing the headgear to elongate or retract freely. When the direction of movement of the core strap 1010 is reversed, such as when the headgear returns to a smaller circumference, the roller ball 1004 travels to the free side of the locking chamber 1002 (to the left in FIG. 15A) and the switch 1006 resets. If the core strap 1010 is then pulled, the mechanism 1000 again acts as a roller ball lock as described above to resist further elongation of the headgear.

The locking and release positions of another roller ball lock mechanism 1020 are shown in FIG. 15B. In this configuration, the locking chamber includes a roller ball 1024 and a switch 1026. The switch 1026 may be a wedge-shaped member having a top surface 1036 that lies adjacent to an upper inner surface 1038 of the locking chamber 1022. The switch 1026 may also include a portion 1040 that is shaped to contain the roller ball 1024 within the locking chamber 1022. In some configurations, the portion 1040 also can be configured to engage with the core strap 1030 to reduce or eliminate the likelihood of further elongation of the headgear when the roller ball lock mechanism 1020 is in a locked position. In some configurations, the mechanism 1020 may include a magnet 1032 and a magnetic member 1034. The magnet 1032 may be located within a housing of the roller ball lock mechanism 1020 while the magnetic member 1034 may be located on one end of the switch 1026, proximal to the surface 1036.

When the switch 1026 is engaged with the core strap 1030, as shown in the lower illustration of FIG. 15C, friction between the roller ball 1004 of the switch 1026 and the core strap 1030 substantially resists further elongation of the core strap 1030. As in the configuration discussed with reference to FIG. 15A, at a predetermined force acting to elongate the headgear that overcomes the friction between the roller ball 1004 of the switch 1026 and the core strap 1030, the switch 1026 changes position by pivoting around the pivot point 1028 to release the core strap 1030 and allow the core strap 1030 to move freely. With the switch in this position, the headgear is substantially free to elongate or retract. When the direction of movement of the core strap 1030 is reversed, such as when the headgear returns to a smaller circumference, the roller ball 1024 travels to the free side of the locking chamber 1022 (to the left in FIG. 15B) and the switch 1026 resets. If the core strap 1030 is then pulled, the mechanism 1020 again acts as a roller ball lock as described above to resist further elongation of the headgear. The magnet 1032 and the magnetic member 1034 may act to hold and reset the switch 1026.

A second embodiment of a high resistance to start movement configuration is shown in FIGS. 16A and 16B. In this embodiment, self-regulating washer friction holds the core strap to reduce or eliminate the likelihood of further elongation until the friction is overcome and the core strap is released to elongate or retract with a low load force. FIGS. 16A and 16B include a self-regulating washer mechanism 1100 that provides a balanced fit as that concept is discussed above. The self-regulating washer mechanism 1100 includes an S-shaped friction member 1104 having a bendable curve 1110 and a self-regulating washer 1106 adjacent to the bendable curve 1110 portion of the S-shaped member 1104. The friction member 1104 and the curve 1110 can be positioned within a housing 1111 and a stretch component 1113 can be secured to the housing 1111, for example but without limitation. A core strap 1108 of the headgear passes through an orifice in the S-shaped member 1104 and also through the washer 1106. The core strap 1108 can pass through or alongside at least a portion of the stretch component 1113.

When the washer 1106 and S-shaped member 1104 are at an angle at to a longitudinal axis of the core strap 1108, designated by 1112 in FIG. 16, the core strap 1108 resists elongation due to frictional forces between the washer 1106 and the core strap 1108 and the S-shaped member 1104 and the core strap 1108. These frictional forces may be overcome with additional load force applied to the core strap 1108. When sufficient force is applied to the S-shaped member, the orifices of the S-shaped member 1104 and the washer 1106 become better aligned due to flexure of the S-shaped member. With flexure, the self-regulating washer mechanism 1100 takes the shape as shown in the lower panel of FIG. 16. In this configuration, the bendable curve 1110 and the washer 1106 are at an angle β to the longitudinal axis, designated by 1114 in FIG. 16. The angle 1114 is closer to ninety degrees than the angle 1112, allowing the core strap 1108 to more easily pass through the openings in the S-shaped member 1104 and the washer 1106. In this configuration, the frictional forces exerted on the core strap 1108 are less, allowing the core strap 1108 to elongate and retract with less required load force. When the direction of pull on the core strap 1108 is reversed, the bendable member 1110 of the S-shaped frictional member 1104 and the washer 1106 return to an orientation similar to that in the top panel of FIGS. 16A and 16B. As discussed above, this configuration limits elongation of the core strap 1108 due to frictional forces on the core strap 1108 until a sufficiently high load is applied, which load is greater than that typically encountered during normal treatment use of a CPAP device.

Figure 17:
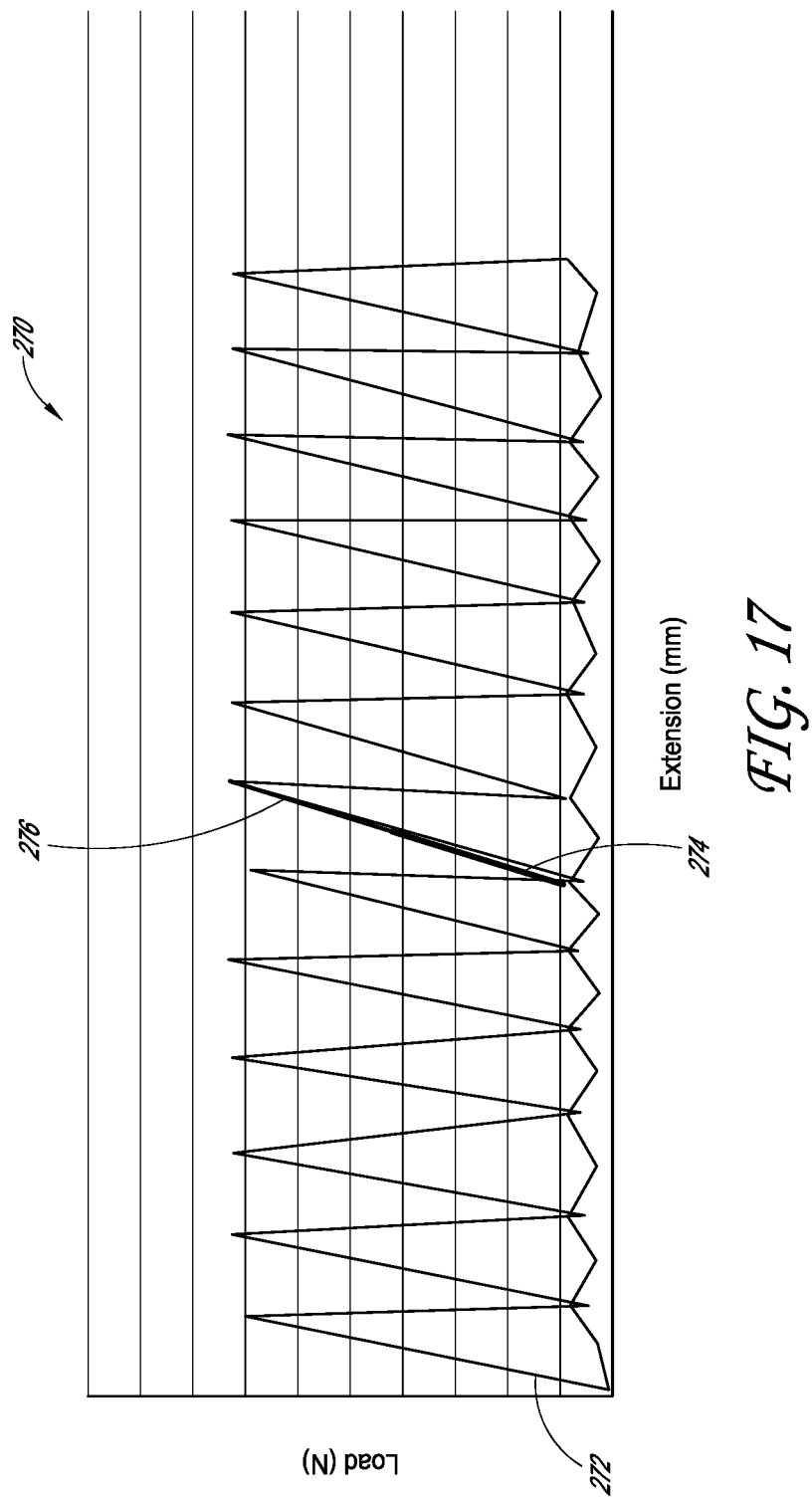
FIG. 17 is a graphic illustration of a force profile associated with headgear having a repeated high resistance to elongation mechanism.

FIG. 17 illustrates a third force profile incorporating a balanced fit feature. In this figure, a repeated high resistance to elongation load profile 270 is shown. Headgear configured with this force profile has a locking mechanism that gives way at a predetermined force before resetting. This sequence of release and reset repeats throughout the extension of the headgear. As shown in FIG. 17, the load curve 272 is composed of a series of repeating high load force peaks as the headgear is extended. The load curve 272 requires less force to retract, as shown by the lower portion of the curve 272. As with the force profiles discussed above, a balanced fit component 274 and a reserve component 276 respectively compensate for the blow-off forces and prevent further elongation of the headgear due to external forces such as hose pull. Moreover, as illustrated, the balanced fit component 274 can have a load-extension slope that approximates the load-extension slope of the increasing load portion of the load curve 272.

Figure 18B:
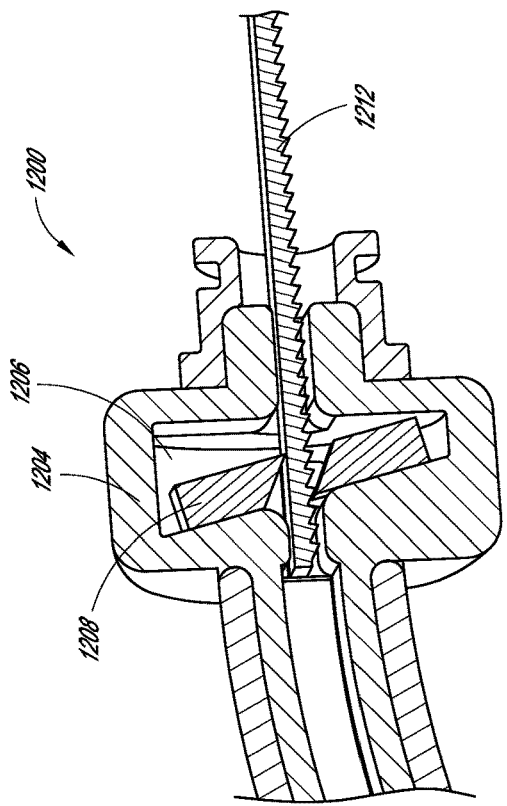
FIG. 18B is a schematic illustration of the embodiment of headgear having a repeated high resistance to elongation mechanism shown in FIG. 18A with the mechanism shown allowing retraction.
Figure 18A:
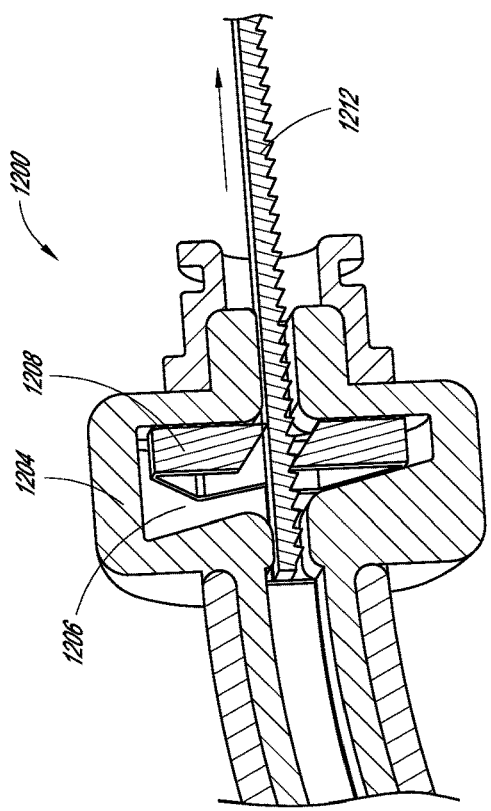
FIG. 18A is a schematic illustration of one embodiment of headgear having a repeated high resistance to elongation mechanism shown with the mechanism resisting elongation.

A ratchet mechanism 1200 that provides a repeated high resistance to elongation is shown in FIGS. 18A-B. The illustrated ratchet mechanism 1200 includes a housing 1204 having an interior cavity 1206 housing a spring-loaded clip 1208. The clip 1208 is configured to interact with the serrated edge of a non-stretch core strap 1212 that runs through the housing 1204. When the core strap 1212 is pulled or extended, the clip 1208 engages with the serrated edge of the core strap 1212 to resist further elongation. The grip of the clip 1208 on the strap 1212 is overcome when the clip 1208 flexes away, releasing its grip on a single tooth. The spring loaded clip 1208 is then ready to engage with the next tooth of the serrated core strap 1212. Again, upon application of sufficient load force, the clip 1208 releases the next serration of the core strap 1212 and catches on the following serration. In this way, a repeated high resistance to elongation force profile such as the one shown in FIG. 17 is achieved. The illustrated clip 1208 is perpendicular to the core strap 1212 during extension of the serrated core strap 1212 and can be angled during retraction of the core strap 1212.

The core strap 1212 can be housed inside a stretch sheath (not shown) and can extend beyond both ends of the sheath into a plastic tube where the loose ends are housed. The stretch sheath provides the retraction force to return the headgear to the size of the user's head. The Young's modulus of the stretch sheath preferably is tuned so that the sheath applies a force to the user's head that is less than or equal to the minimum possible blow-off force such that the sheath provides the initial balancing force. For higher blow-off forces, the non-stretch components may provide the additional balancing forces.

The core strap 1212 preferably has stoppers on the ends to reduce or eliminate the likelihood of the ends of the strap 1212 being pulled out of the housing tube. The core strap 1212 forms a closed loop with the housing. The tubular housing can clip into the mask frame. Clip housings (not shown) can connect the stretch sheath and housing together.

When an extension force is applied to the headgear, the core strap 1212 pulls the clip 1208 flush against the square internal wall of the housing 1204. This causes the clip 1208 to further engage with the teeth on the core strap 1212. The engagement is overcome when the clip 1208 flexes away, releasing its grip on a single tooth, ready to engage with the next tooth. The force required to overcome each tooth on the core strap and elongate the headgear is greater than or equal to the specified applied force.

When the headgear is released from an elongated position, the clip 1208 rotates in its housing 1204, becoming flush with the angled wall of the housing 1204. This allows the clip 1208 to disengage the teeth of the core strap 1212, which in turn allows the headgear to retract freely.

Initially, the CPAP pressure is balanced by the low force applied by the elastic component to the user's head. As the force applied by the CPAP pressure increases, the non-stretch core strap 1212 will provide additional resistance to elongation, pushing the spring clip 1208 against the perpendicular housing wall and engaging the teeth, thus providing the remainder of the balancing force. As the force applied by the CPAP pressure preferably does not exceed the specified yield force to overcome the teeth on the core strap 1212, the length of the headgear will remain substantially constant unless modified by the user.

Retraction of the core strap 1212 is shown in FIG. 18B. In this figure, the core strap 1212 is retracted through the housing 1204, causing the clip 1208 to rotate within the housing 1204 thus allowing the clip 1208 to disengage from the teeth of the core strap 1212. The strap 1212 can retract with very little resistance in this configuration.

Figure 19B:
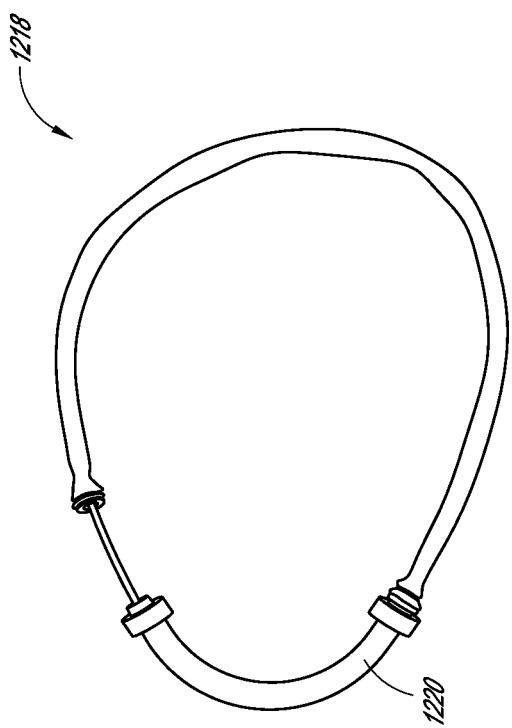
FIG. 19B is a second illustration of the embodiment of FIG. 18A.
Figure 19A:
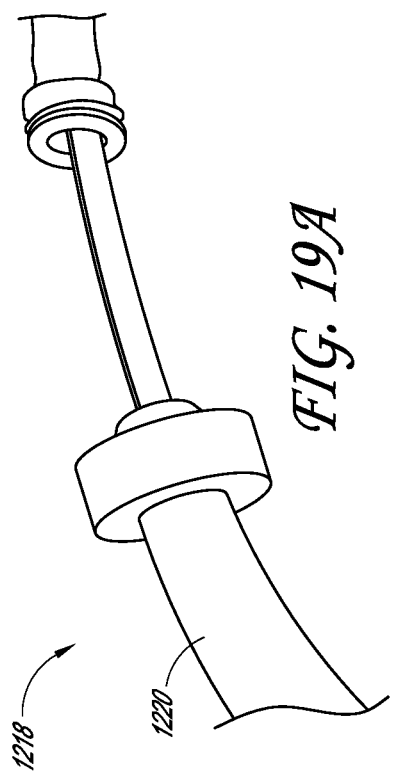
FIG. 19A is an illustration of the embodiment of FIG. 18A.

FIGS. 19A and B illustrate the ratchet mechanism integrated into one embodiment of a strap design 1218. An elastic sleeve 1220 surrounds the ratchet mechanism to automatically retract the headgear.

Figure 20:
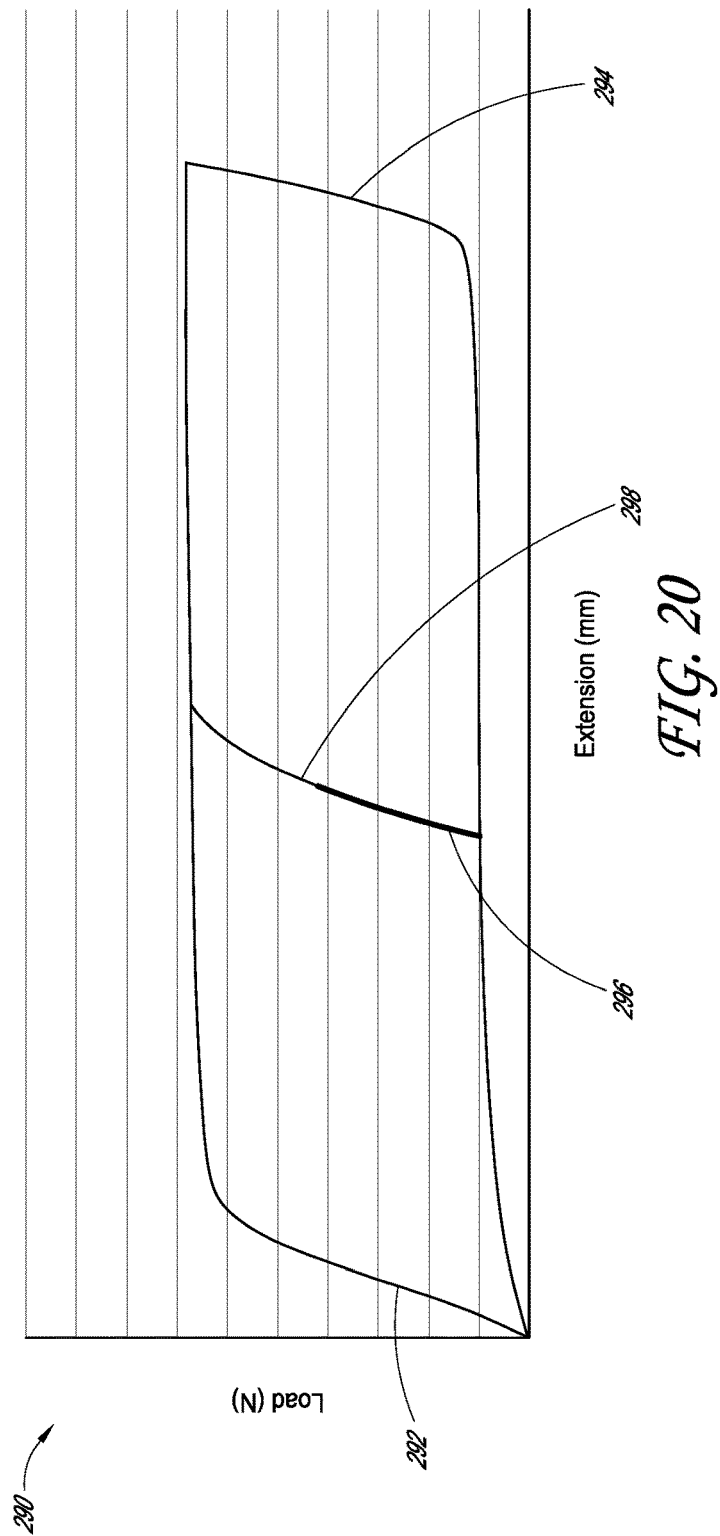
FIG. 20 is a graphic illustration of a force profile associated with headgear having a large hysteresis mechanism.

A fourth force profile incorporating a balanced fit is shown in FIG. 20. In this figure, a large hysteresis load profile 290 is shown. Headgear configured with this force profile has a high load force resistance to elongation or extension. With reference to FIG. 20, the high build-up of force is shown in the extension section 292 of the load curve. During this extension phase of the headgear, the extension force may be between about 7 and 8 N as determined by the sum of the blow-off force and an estimated 3 N hose pull force. When the headgear retracts, as shown in the retraction section 294 of the load curve, the returning force is preferably no greater than about 2.5 N. This returning force is the force exerted on a user's face primarily by the elastic component of the headgear.

A balanced fit of the headgear may comprise two components, as discussed above: a balanced fit component and a reserve component. The balanced fit component 296 of the load curve shown in FIG. 20 compensates for the blow-off force applied by the CPAP pressure. The reserve component 298 of the load curve may cover a range of load forces extending up to the load force during the large hysteresis section of the extension curve 292. In some embodiments, the extension during the balanced fit phase is no greater than about 10 mm. As shown, in some configurations, the balanced fit component 296 follows a slope similar to or the same as the initial elongation slope. In some configurations, the balanced fit component 296 has a lower slope than the slope of the retraction section 294. Other configurations are possible.

FIGS. 21A and B illustrate a cross section of one embodiment of a headgear mechanism that incorporates the large hysteresis load profile discussed above. In this embodiment, a washer concept headgear mechanism 1300 includes a housing 1304 having an internal cavity 1306. The internal cavity 1306 is configured to have a free movement surface 1310 that is substantially vertical and orthogonal to a longitudinal axis defined by a core strap 1316. The internal cavity 1306 is also configured to have a locking surface 1312 that is angled with respect to the longitudinal axis defined by the core strap 1316. A washer 1308 is located within the internal cavity 1306. An orifice through both the housing 1304 and the washer 1308 allow a non-stretch core strap 1316 to be threaded through the orifices. The housing 1304 forms the ends of a tube that houses the ends of the non-stretch core strap 1316. In some configurations, the tube is generally elastic. This tube can make the headgear into a closed loop and can clip into the mask frame (not shown).

With reference to FIG. 21A, free movement of the core strap 1316 is illustrated. When the washer 1308 is aligned with the free movement surface 1310 of the housing 1304, there is little to no friction between the washer 1308 and housing 1304 and the core strap 1316. Therefore, in this configuration, the core strap 1316 has a substantially straight path through the washer 1308 and the housing 1304 and is substantially free to move in the free movement direction indicated by arrow 1318.

With reference now to FIG. 21B, high friction resistance to movement of the core strap 1316 is illustrated. When the core strap 1316 is pulled in the opposite direction of the free movement direction, indicated by arrow 1320, the washer 1308 is forced to tip over and rest adjacent to the angled locking surface 1312 of the housing 1304. This orientation of the washer 1308 within the housing 1304 creates an angled path for the core strap 1316. This angled path increases the friction between the washer 1308 and the core strap 1316. The increased friction limits movement of the core strap 1316, which resists elongation of the headgear.

FIGS. 22A-22D illustrate one embodiment of a washer concept headgear mechanism incorporated within a headgear assembly. As shown in FIGS. 22A-22D, each headgear assembly can include two washer mechanisms on a non-stretch core strap. The middle section of the core strap can be housed inside a stretch sheath. The core string preferably has stoppers on the ends to reduce or eliminate the likelihood of the core string being pulled out of the housing tube. The stretch sheath is desirably connected to the housing tube at both ends. FIG. 22A also illustrates a free movement configuration at 1330. FIG. 22B at 1332 illustrates a high friction movement configuration.

Figure 23A:
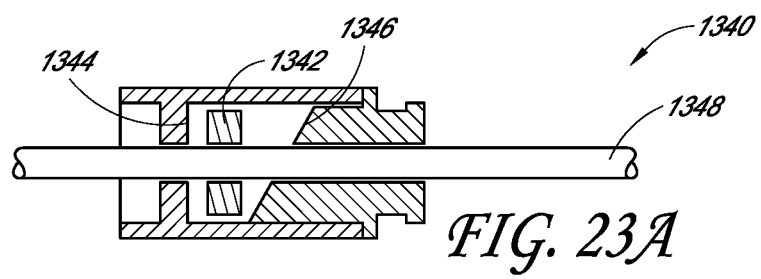
FIGS. 23A, 23B and 23C are respective schematic illustrations of a second, third, and fourth embodiment of headgear each having a large hysteresis mechanism.
Figure 23B:
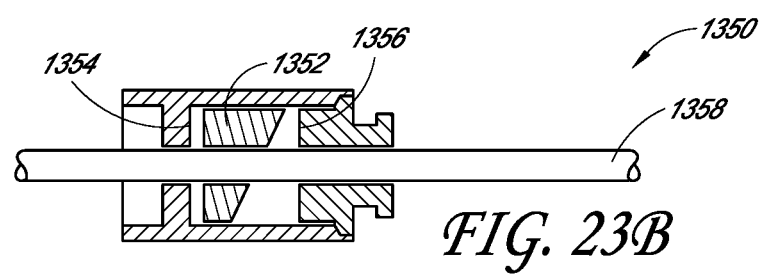
Figure 23C:
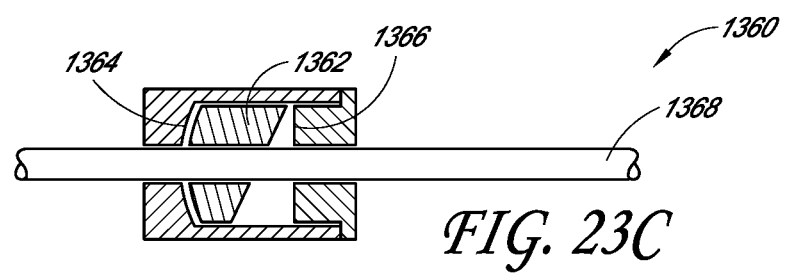

Three additional embodiments of a washer concept that provides high friction resistance to movement of a core strap are shown in FIGS. 23A-23C. As illustrated in each concept 1340, 1350, and 1360, the washer shape may change from a flat washer 1342 to an angled washer 1352 or angled washer 1362 depending on the construction of the housing. In each case, alignment of the washer 1342, 1352, or 1362 along the free movement surface 1344, 1354, or 1364 of the housing will allow the core strap 1348, 1358, or 1368 to move substantially freely through the washer and the housing. However, when the washer 1342, 1352, or 1362 rotates within the housing to align with the locking surface 1346, 1356, or 1366 of the housing, the core strap is bent, creating an angled, high friction path of movement that limits further elongation of the headgear.

A further embodiment of a washer concept mechanism is illustrated in FIGS. 24A-24E. In this embodiment, the mechanism 1370 includes a washer 1372 disposed within a housing 1374. A rotatable member 1376 is also disposed within the housing 1374. As discussed above with respect to the other washer embodiments, movement of the washer 1372 from one end of the housing to the other influences whether a free movement or high friction movement condition exists. The rotatable member 1376 within the washer mechanism 1370 provides an additional benefit such that the mechanism 1370 is less influenced by a change in pulling angle of the core strap 1378.

In any of the above discussed embodiments, the housing may be manufactured in one or more pieces. The housing and the washer may be manufactured of the same or different materials. In some configurations, the housing and/or the washer can be formed of a generally rigid material. In some configurations, the housing and/or the washer can be formed of a rigid plastic. In some configurations, the housing and/or the washer can be formed of a polycarbonate, a polypropylene, an acetyl or a nylon material. In some configurations, the housing and/or the washer may be formed of a metal.

When headgear having any of the washer mechanisms discussed above with reference to FIGS. 21A-B, 22, 23, and 24 are extended, the small amount of friction between the washer and the core strap causes the washer to be pulled towards the angled end wall of the housing. This results in the washer sitting on an angle inside the housing, creating a crooked path for the core strap to pass through. This crooked path creates a tension force in the core strap and increases the resistance to movement between the core strap and the washer mechanism. The resistance is such that a force greater than the specified yield force is required to elongate the headgear.

When there are no tension forces on the headgear including a washer mechanism, the washer returns to its neutral position adjacent to the perpendicular end wall. In this position, the washer imposes minimal frictional forces on the core strap. When the headgear is released, the core strap can be drawn freely through the housing and the washer. The elastic sheath provides the retraction force required to shorten the headgear.

The elastic sheath also allows for elongation of the headgear when a force greater than the specified yield force is applied. The Young's modulus of the elastic sheath is preferably tuned so that the sheath can only apply a force to the user's head that is less than or equal to the minimum possible blow-off force. Thus, for these configurations, the elastic provides the initial balancing force for low CPAP pressures.

Initially, the CPAP pressure will be balanced by the low level of force applied by the elastic component to the user's head. As the force applied by the CPAP pressure increases, the non-stretch core strap, in conjunction with the washer mechanism, will limit further elongation. The headgear's natural reaction to an increase in CPAP pressure is to elongate to accommodate the pressure increase; however, this will result in the washer being pushed toward the angled end of the housing, locking the non-stretch core strap in place due to the increased friction. Once the movement of the core strap is restricted, the core strap will provide the remainder of the balancing force. As the force applied by the CPAP pressure will typically not exceed the specified yield force to overcome the resistance of the washer on the core strap, the length of the headgear will remain substantially constant, unless modified by the user.

Figure 25A:
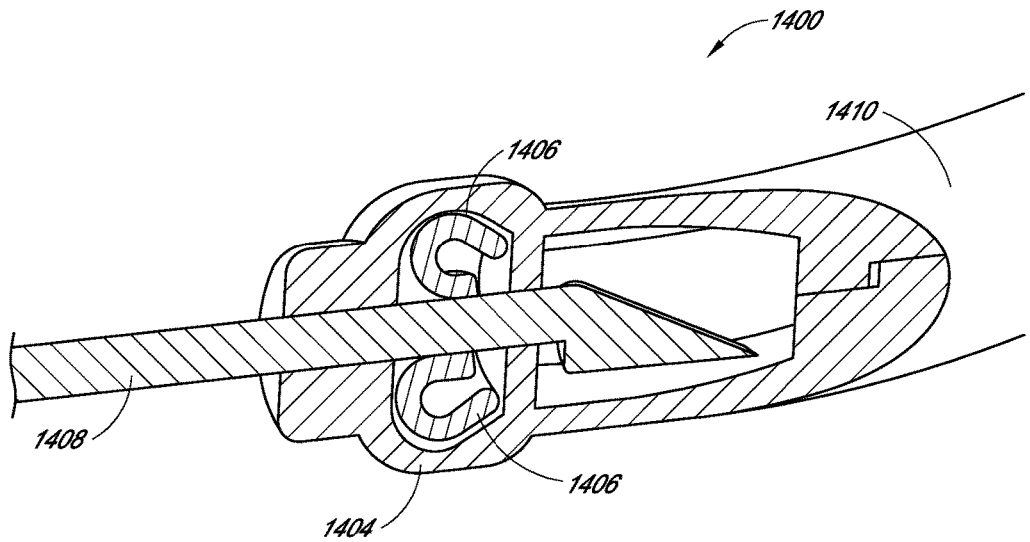
FIG. 25A is a schematic illustration of a sixth embodiment of headgear having a large hysteresis mechanism.
Figure 25B:
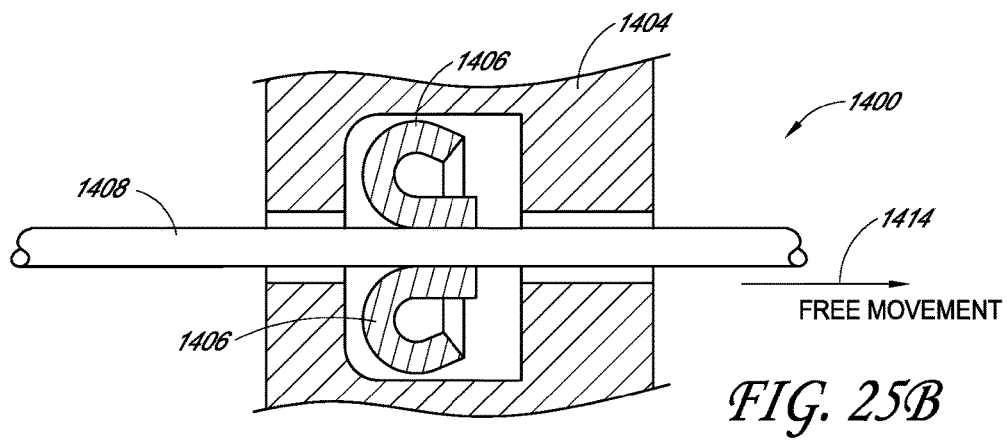
FIG. 25B is another schematic illustration of the embodiment of headgear shown in FIG. 25A shown with the mechanism allowing free movement.
Figure 25C:
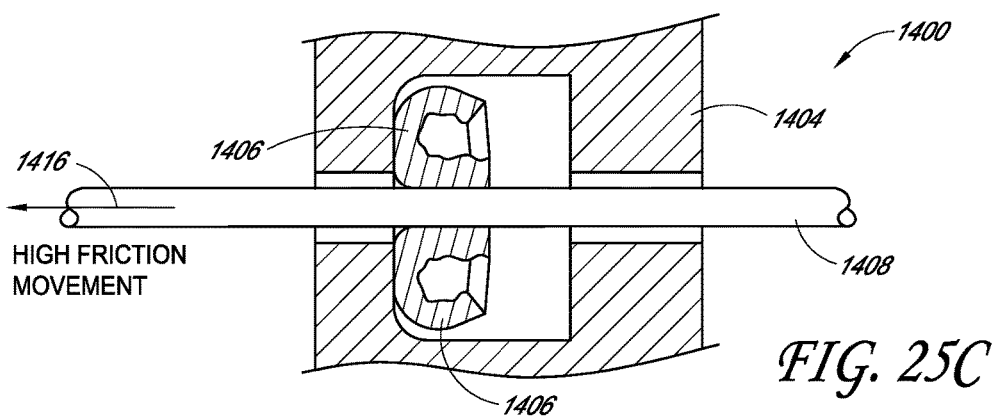
FIG. 25C is a third schematic illustration of the embodiment of headgear shown in FIG. 25A shown with the mechanism providing high friction resistance to movement.

Another embodiment of a large hysteresis mechanism is shown in FIGS. 25A-C. A cross-section of a C-ring mechanism 1400 is shown in FIG. 25A. The mechanism 1400 includes a rigid tubular housing 1404 that may be formed contiguously with a strap member 1410 or may be a separate piece. The housing 1404 includes an orifice through which a non-stretch section of a core strap 1408 may pass. The housing 1404 also contains the loose ends of the core strap (not shown). Within the housing is a resilient washer with a C-shaped cross-section 1406. The washer 1406 is oriented such that the opening of the washer 1406 is oriented toward the mask. The flexible C-shaped washer 1406 may be made of silicon or rubber. With reference to FIG. 25A, the opening defined through the C-shaped member 1406 is oriented in a direction substantially similar to the longitudinal axis of the core strap 1408. At least one leg of each C-shaped member 1406 is adjacent to the core strap 1408. The C-shaped section of the washer 1406 drags over the surface of the non-stretch section of the core strap 1408 that passes through the housing 1404. The housing 1404 and the washer 1406 are configured such that the washer 1406 exerts significant friction when the core strap 1408 is moved in one direction and movement of the core strap 1408 in the other direction is substantially free, as will be discussed in greater detail below.

With reference now to FIGS. 25B and C, free movement and high friction movement of the core strap 1408 are shown. Depending on the direction of movement, the washer 1406 reacts differently. When the core strap 1408 is moving the in free movement direction 1414, the center of the washer 1406 tends to "unroll," as shown in FIG. 25B. When the center of the washer 1406 unrolls, friction on the core strap 1408 is reduced. When the core strap 1408 is moving in the other direction, a high friction movement direction 1416, as shown in FIG. 25C, the center of the washer 1406 in contact with the core strap 1408 is crunched up or compressed. This deformation increases the friction on the core strap 1408, increasing the force required to elongate the headgear. FIGS. 26A-26C illustrate two views of one embodiment of a headgear assembly having a C-ring mechanism as discussed above. The middle section of the core strap 1408 is housed inside a stretch sheath. The stretch sheath can be connected to the housing 1404 at both ends. The stretch sheath provides the retraction force to return the headgear to the size of the user's head. The Young's modulus of the stretch sheath can be tuned so that the sheath can apply a force to the user's head that is less than or equal to the minimum possible blow-off force. This means that the stretch sheath provides the initial balancing force. In cannula systems, the Young's modulus can be tuned to be the lowest possible or practicable required to hold the cannula to a user's head, in order to maximize comfort. For high blow-off forces (or external forces in a cannula system), the non-stretch components will provide the additional balancing forces. The core strap 1408 preferably has stoppers on the ends to reduce or eliminate the likelihood of the ends being pulled out of the housing 1404. By containing the ends of the core strap 1408, the headgear forms a closed loop. The housing 1404 preferably clips into the mask frame to connect the headgear to the mask.

In the embodiments shown in FIGS. 25A-C, when an extension force is applied to the headgear, the core strap 1408 pulls the round section of the washer 1406 against the internal wall of the housing 1404. This causes the washer 1406 to crush and increases the friction on the core strap 1408. The friction provided by the washer 1406 is such that the force required to elongate the headgear is greater than the specified yield force. When the headgear is released from an elongated position, the washer 1406 returns to its natural shape, allowing the core strap 1408 to pass through the housing 1404 and through the washer 1406 with substantially lower resistance. When the open side of the washer 1406 is pulled against the wall of the housing 1404, it does not crumple or deform and the friction on the core strap 1408 remains low.

Initially, the CPAP pressure will be balanced by the low level of force applied by the elastic or stretch component to the user's head. As the force applied by the CPAP pressure increases, the non-stretch core strap 1408 acts to restrict further elongation. The natural reaction of the headgear is to elongate to accommodate the increased CPAP pressure; however, this will result in the round side of the washer 1406 being pushed against the wall of the housing 1404, increasing friction and "locking" the non-stretch core strap 1408 in place. Once the movement of the core strap 1408 is restricted, it will provide the remainder of the balancing force. As the force applied by the CPAP pressure typically does not exceed the specified yield force to overcome the friction of the washer 1406 on the core strap 1408, the length of the headgear will remain substantially constant unless modified by the user.

Another embodiment of a large hysteresis mechanism is illustrated in FIGS. 27A-27D. In FIG. 27A, an alternative washer mechanism 1500 includes a housing 1504 that incorporates a crushable core member 1506. The crushable core member 1506 may be configured in a cone shape such that the cone can crush or deform to increase friction on the core strap 1508. When the core strap 1508 moves in the free movement direction, indicated by arrow 1510, friction on the core strap 1508 is minimal and the crushable core member 1506 does not substantially resist free movement of the core strap 1508, as shown in FIG. 27B. When the core strap 1508 moves in the high friction movement direction, indicated by arrow 1512, the crushable core member 1506 is deformed or "crunches up" to the left, as shown in FIG. 27C.

With continued reference to FIG. 27A, graph 1520 indicates that as the resistance increases due to the deformation of the crushable core member 1506, the resistance to movement of the core strap 1508 steeply increases. The resistance to movement remains high for further elongation of the core strap 1508, corresponding to a large hysteresis force profile such as the one described with reference to FIG. 20.

Yet another embodiment of a large hysteresis mechanism is illustrated in FIGS. 28A and 28B. In FIG. 28A, a roller ball lock mechanism 1600 includes a rigid tubular housing 1604 having an interior chamber 1608. The interior chamber 1608 is ramped to be larger at one end than the other. The interior ramped chamber 1608 houses a roller ball 1606. The roller ball 1606 is encased between the wall of the interior ramped chamber 1608 and a non-stretch core strap 1610. The housing 1604 further includes an orifice such that the core strap 1610 may pass through the housing and further contains the loose ends of the core strap 1610, forming a closed loop. The core strap 1610 preferably has stoppers on the ends to prevent the ends from being pulled out of the housing 1604. The housing 1604 can then clip into the mask frame. In this configuration, when the roller ball 1606 is at one end of the interior cavity 1608, the roller ball 1606 presses against the core strap 1610, increasing friction and the load force required to further extend the core strap 1610. With continued reference to FIG. 28A, when the core strap 1608 is pulled in the direction indicated by arrow 1612, the roller ball 1606 is driven into the smaller end of the interior cavity 1608. Due to the ramped shaped of the interior cavity 1608, when the core strap 1608 is moved in the opposite direction, the roller ball 1606 is driven to the "high ceiling" end of the interior cavity 1608 where there is greater room for the roller ball 1606. Therefore, the roller ball 1606 has minimal interference with the core strap 1608, thereby reducing the friction exerted by the ball. One example of this roller ball lock mechanism incorporated within a headgear assembly is shown in FIG. 28B. The middle section of the core strap 1610 is housed within a stretch sheath 1612. The stretch sheath 1612 can be connected to the housing 1604 at both ends. The stretch sheath 1612 provides the retraction force to return the headgear to the size of the user's head. The Young's modulus of the stretch sheath 1612 is preferably tuned so that the sheath 1612 can only apply a force to the user's head that is less than or equal to the minimum possible blow-off force. This means that the stretch sheath 1612 provides the initial balancing force. In cannula systems, the Young's modulus can be tuned to be the lowest possible or practicable required to hold the cannula to a user's head, in order to maximize comfort. For higher blow-off forces, the non-stretch components will provide the additional balancing forces.

When an extension force is applied to headgear having the roller ball mechanism described above with reference to FIGS. 28A-C, the core strap 1610 pulls the roller ball 1606 towards the narrow end of the ramped chamber of the housing 1604. This subsequently drives the roller ball 1606 into the core strap 1610 and increases the friction on the core strap 1610. The increased friction is such that the force required to elongate the headgear is greater than the specified yield force.

When the headgear is released from an elongated position, the roller ball 1606 is driven back towards the wider end of the ramped chamber of the housing 1604, thus reducing the friction on the core strap 1610 and allowing the core strap 1610 to pass through the chamber with substantially lower resistance.

Initially, CPAP pressure will be balanced by the low level of force applied by the stretch sheath component 1612 to the user's head. As the force applied by the CPAP pressure increases, the non-stretch core strap 1610 will act to resist further elongation. The headgear will naturally want to elongate to accommodate the CPAP pressure; however, this will result in the roller ball 1606 being pushed towards the narrow end of the ramped chamber 1608, "locking" the core strap 1610 in place. Once the movement of the core strap 1610 is resisted, it will provide the remainder of the balancing force. As the force applied by the CPAP pressure typically does not exceed the specified yield force to overcome the friction of the roller ball 1606 on the core strap 1610, the length of the headgear will remain substantially constant unless modified by the user.

A second roller ball lock mechanism 1620 having a large hysteresis force profile is illustrated in FIG. 28C. In this figure, the mechanism 1620 includes a housing 1624 having an interior chamber 1628 that includes a separate wedge or switch member 1632. The wedge member 1632 acts as a hinged release switch that is encased between the roller ball 1626 and the chamber 1628. In this embodiment, the wedge member 1632 is included to improve the quick release of the roller ball 1626 from the core strap 1630. The wedge member 1632 has an angled surface that creates a ramped chamber when engaged and a rectangular chamber when released. The middle section of the core strap 1630 is housed within a stretch sheath similar to the sheath 1612 shown in FIG. 28B. The stretch sheath can be connected to the housing 1624 at both ends. The stretch sheath provides the retraction force to return the headgear to the size of the user's head. The Young's modulus of the stretch sheath is preferably tuned so that the sheath can only apply a force to the user's head that is less than or equal to the minimum possible blow-off force. This means that the stretch sheath provides the initial balancing force. In cannula systems, the Young's modulus can be tuned to be the lowest possible or practicable required to hold the cannula to a user's head, in order to maximize comfort. For higher blow-off forces, the non-stretch components will provide the additional balancing forces.

Upon reversal of direction to a free movement direction, as indicated by the arrow 1634, the wedge 1632 and the roller ball 1626 move together a small distance before the wedge 1632 falls away within the cavity 1628, instantly releasing the grip between the core strap 1630 and the roller ball 1626. The core strap 1630 is then allowed to move freely.

The switch 1632 is naturally in an engaged position, creating a ramped chamber. When an extension force is applied to the headgear, the core strap 1630 pulls the roller ball 1626 towards the end of the chamber 1628 that is made narrow by the switch 1632. As the ball 1626 is driven into the switch 1632, the compression force increases until the roller ball 1626 is directly over the axis of rotation of the switch 1632, at which point the switch 1632 is released. The release of the switch 1632 creates a rectangular chamber

1628 and reduces the resistance between the switch 1632, ball 1626, and core strap 1630, allowing the ball 1626 to move within the chamber 1628 and the headgear to be extended easily with only the force required to overcome the elastic stretch sheath and some frictional forces between the mechanism components.

When the switch 1632 has been released and the ball 1626 has rolled to the extension end of the chamber 1628, the core strap 1630 can move through the mechanism 1620 with minimal resistance in both directions. Resetting the switch 1632 is done after the core strap 1630 reverses its direction of travel and returns the ball 1626 to the other (retraction) end of the chamber 1628. Once the ball 1626 has been rolled back past the switch 1632 rotation axis, the switch 1632 is reset and the chamber 1628 becomes ramped again.

When the headgear is released from an elongated position and allowed to retract, the roller ball 1626 is driven back towards the extension, or more open, side of the chamber 1628. The change in position of the roller ball 1626 re-engages the switch 1632 but also maintains the lower resistance level between the components, allowing the core strap 1630 to pass through the chamber 1628 with little resistance.

Initially, the CPAP pressure will be balanced by the low level of force applied by the elastic sheath component to the user's head. As the force applied by the CPAP pressure increases, the non-stretch core strap 1630 will provide additional resistance to elongation. The headgear's natural reaction will be to elongate to accommodate the CPAP pressure; however, this will result in the roller ball 1626 being pushed towards the angled switch 1632 surface which will cause an increase in friction between the ball 1626, core strap 1630, and the switch 1632. The force applied by the air pressure will preferably not be enough to overcome the friction and cause the switch 1632 to release, thus further elongation of the headgear will be limited. The switch force is preferably about equal to the specified yield force.

Figure 29A:
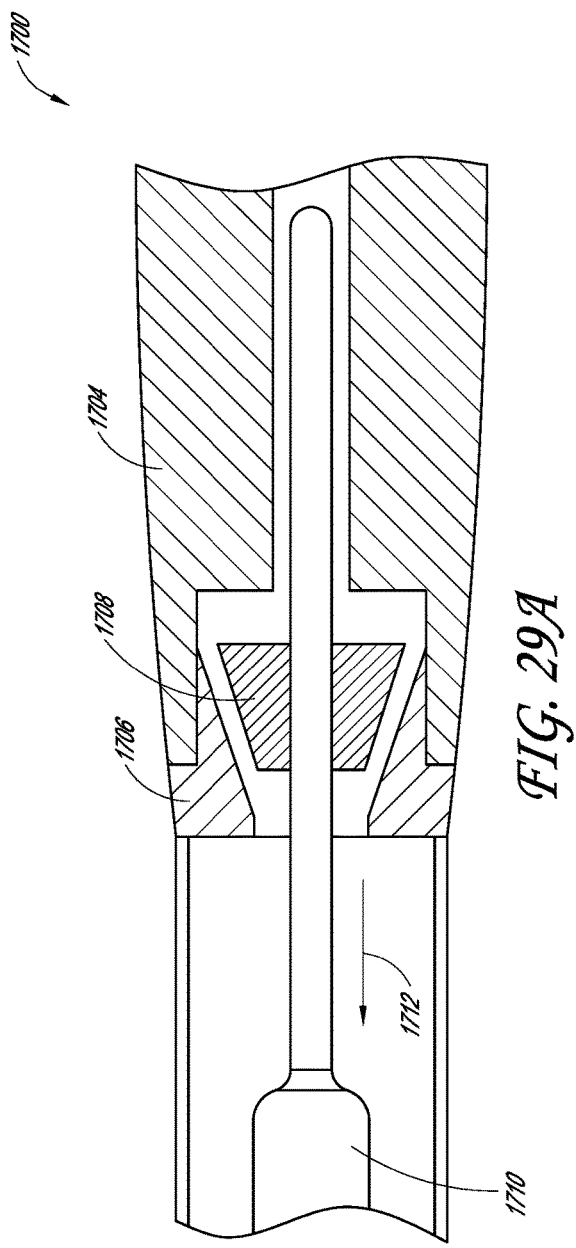
FIG. 29A is a schematic illustration of a tenth embodiment of headgear having a large hysteresis mechanism.
Figure 29C:
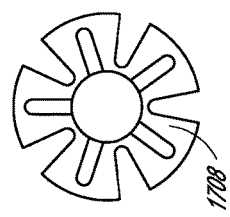
FIG. 29C is an end view of the collet member of FIG. 28B.
Figure 29B:
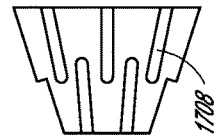
FIG. 29B is a side view of a collet member of the tenth embodiment of headgear.

FIGS. 29A-29C illustrate an alternative embodiment to the roller ball mechanism for large hysteresis. A collet mechanism 1700 includes a two part housing 1704, 1706 that is conical at one end. The housing members 1704, 1706 for the ends of a rigid tubular housing that contains the loose ends of a non-stretch core strap 1710. The housing contains a collet member 1708 that forms a collar around the core strap 1710. The collet member 1708 preferably has the shape of a truncated cone and, as in the illustrated embodiment, may have one or more kerf cuts along its length to allow the collet member 1708 to expand and contract. The collet member 1708 exerts a strong clamping force on the non-stretch core strap 1710 when the collet member 1708 is pulled in the direction indicated by arrow 1712 that is, into the conical chamber formed in the housing. Similar to the roller ball mechanisms discussed above, the core strap 1710 experiences high frictional forces when the collet member 1708 is pulled into the conical chamber of the housing. The core strap 1710 is substantially free to move when pulled in the opposite direction.

The middle section of the core strap 1710 is housed within a stretch sheath that is connected to the housing at both ends, as described above with reference to other embodiments. The non-stretch core strap 1710 preferably has stoppers on the ends to reduce or eliminate the likelihood of the loose ends being pulled out of the housing, forming a closed loop headgear assembly. The housing tube can clip into a mask frame.

When an extension force is applied to the headgear, the core strap 1710 pulls the collet member 1708 into the conical end of the housing. This causes the collet member 1708 to be compressed onto the core strap 1710, increasing the friction between the two components. The friction provided by the compressed collet member 1708 is such that the force required to elongate the headgear is greater than the specified applied force.

When the headgear is released from an elongated position, the collet member 1708 returns to its neutral position which allows the core strap 1710 to pass through it more freely. The elastic sheath provides the retraction force to return the headgear to the size of the user's head. The Young's modulus of the elastic sheath may be tuned so that the sheath can only apply a force to the user's head that is less than or equal to the minimum possible blow-off force. In this configuration, the elastic provides the initial balancing force. For higher blow-off forces, the non-stretch components will provide the additional balancing forces.

Initially, the CPAP pressure will be balanced by the low level of force applied by the elastic component to the user's head. As the force applied by the CPAP pressure increases, the non-stretch core strap 1710 will restrict further elongation. The headgear's natural reaction is to elongate to accommodate the CPAP pressure; however this will result in the collet member 1708 being pushed towards the conical end of the housing and thus the non-stretch core strap 1710 will be locked in place. Once the movement of the core strap 1710 is restricted it will provide the remainder of the balancing force. As the force applied by the CPAP pressure preferably does not exceed the specified yield force to overcome the friction of the collet member 1708 on the core strap 1710, the length of the headgear will remain constant unless modified by the user.

For headgear that provides a large hysteresis force extension profile in combination with the mask, the force required to extend the headgear for fitting is preferably not much higher than the specified yield force to allow easy recognition of the adjustment function by the user. A very high extension force might cause user confusion as this large required force may appear unnatural and the user might fear breaking a component of the headgear.

Figure 30:
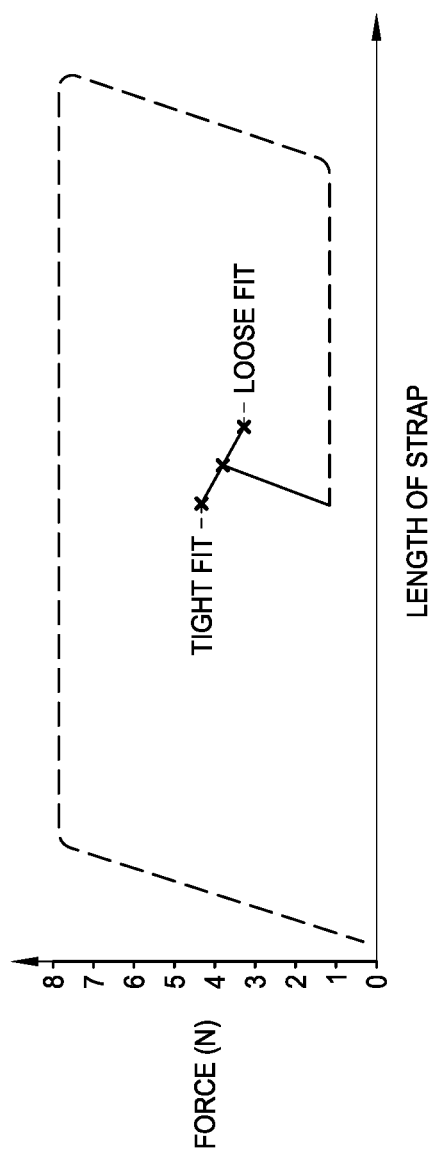
FIG. 30 is a graphic illustration of a force profile for headgear allowing adjustment to a loose or tight fit.

The headgear also preferably allows the fit to be adjusted to the user's preference. FIG. 30 illustrates a force profile for a large hysteresis mechanism headgear that includes a section that allows the user to choose how they want the seal of the mask to fit. This force profile also takes into account differing facial geometries between users. The user will be able to push the mask onto their face to create a larger contact area and tighter fit with the seal, due to further retraction of the strap. This will increase the force applied by the headgear but will not exceed the force required to overcome the friction mechanism, such as those described above, and elongate the headgear. For users who prefer a loose fit, the non-stretch or low-stretch component of the headgear will enable the mask to be held in place with the minimum force required to counter the blow-off force while still maintaining a seal with the user's face, or counter the weight of and hold a cannula in place.

Force profiles at various pressures are shown in FIGS. 31A and B. FIG. 31B illustrates the force profile of the Pilairo elastic strap headgear. It is clearly visible that the force is nearly constant and is hardly influenced by CPAP pressure. This figure also shows a wide spread between test subjects which is a result of the different head sizes of each test user.

In contrast, the graph shown in FIG. 31A is generated using a one-way-friction head strap. In this example, a tunnel concept headgear is used, but our other concepts such as those discussed above would have generated similar results. This figure illustrates the advantage of a balanced fit. At low pressures, the headgear produces considerably lower forces on the user's head as compared to the Pilairo elastic strap headgear. FIG. 31A also shows less spread in measurements of different users. The spread comes from the way the seal is created, as some people need or prefer more engagement than others.

FIG. 31C illustrates the difference between the average of each of the first two graphs shown in FIGS. 31A and B. In this graph, it is easy to see the large force difference at the lower end of CPAP pressure scale. Headgear that includes one of the mechanisms discussed above can improve user comfort. This is especially true in combination with an intelligent supply of CPAP, such as a pressure ramping or varying pressure technology.

Note that FIG. 31C reflects average values; however, the balanced fit mechanism is designed to optimize the effect for each individual user.

Figure 32:
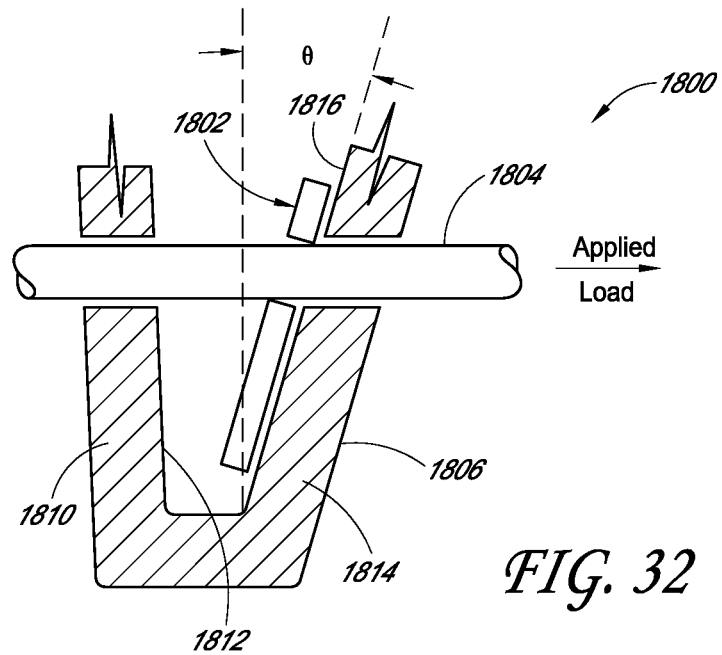
FIG. 32 is a partial sectional view of a directional lock utilizing a movable lock member within a lock chamber of a housing and a core member that is engaged by the lock member.

FIG. 32 illustrates an adjustment mechanism 1800 having variable directional properties, which can be utilized in a self-fit interface assembly. The illustrated adjustment mechanism 1800 provides directional locking functionality and, thus, can be referred to as a directional locking mechanism or, simply, a directional lock. The directional lock 1800 allows relative movement between two components in a first direction at a first level of resistance and provides a second, preferably higher level of resistance in response to relative movement (or attempted relative movement) in a second direction, which inhibits or prevents relative movement in the second direction in response to at least some loading conditions. In some configurations, the directional lock 1800 prevents relative movement in the second direction in response to normal operational forces, such as one or more of CPAP-produced blow-off force and external force (e.g., hose pull force). The directional lock 1800 can also prevent relative movement in the second direction in response to additional forces above the expected or normal blow-off force and/or hose pull force to provide a reserve, as described previously. Thus, the directional lock 1800 can be configured to provide a locking function only in response to normal operational forces (plus a reserve, if desired) and can allow relative movement between the two components in response to forces of a magnitude above the normal operational forces (and reserve, if desired) to permit, for example, extension of the headgear portion of the interface assembly during the application phase of the fitment process. Thus, a headgear arrangement incorporating such a directional lock 1800 can "transform" from stretch behavior to non-stretch behavior or from elastic elongation type behavior to non-elongating type behavior. As used herein, elongation is not necessarily limited to referring to movement in an extension direction, but can refer generally to stretch or elastic behavior in contrast to non-stretch or non-elastic/inelastic behavior. The directional lock 1800 (and other directional locks described herein) can also be referred to as transformational locks that provide transformational locking behavior.

The directional lock 1800 of FIG. 32 is similar in general operational principles to the arrangements of FIGS. 16 and 21 in that a floating or movable lock component or member 1802 (e.g., lock washer or lock plate) is movable between a first, lower resistance or release position and a second, higher resistance or lock position. Features or details not described with respect to the directional lock 1800 of FIG. 32 can be the same as or similar to corresponding features of the arrangements of FIGS. 16 and 21, or can be of another suitable configuration. The illustrated directional lock 1800 includes a core member 1804, such as a core strap or core wire/cord, that passes through an opening of the lock washer 1802. The lock washer 1802 is supported within an enclosure or a housing 1806 for movement between the first position and the second position. Preferably, the housing 1806 includes a first wall 1810 having a first stop surface 1812 that supports the lock washer 1802 in the first position, which preferably is the lower resistance or release position. The housing 1806 preferably also includes a second wall 1814 having a second stop surface 1816 that supports the lock washer 1802 in the second position, which preferably is the higher resistance or lock position. Preferably, the stop surfaces 1812, 1816 are sized, shaped or positioned to support the lock washer 1802 in the desired position. Thus, the stop surfaces 1812, 1816 can be continuous surfaces that contact an entirety or a substantially entirety of the cooperating surface of the lock washer 1802, as illustrated. Alternatively, the stop surfaces 1812, 1816 can be intermittent or discontinuous surfaces, or can contact one or more portions of the lock washer 1802, such as upper and lower end portions of the lock washer 1802, for example.

Preferably, the lock washer 1802 is positioned generally perpendicular to a longitudinal axis of a portion of the core member 1804 positioned within the lock cavity of the housing 1806 in the first, lower resistance or release position such that the opening or hole of the washer 1802 is positioned generally parallel to or aligned with the core member 1804. Preferably, the lock washer 1802 is positioned at an oblique angle relative to the longitudinal axis of a portion of the core member 1804 positioned within the lock cavity of the housing 1806 in the second, higher resistance or lock position such that the opening or hole of the washer 1802 is positioned at an oblique angle to the core member 1804. Thus, in some configurations, the first stop surface 1812 can be generally perpendicular to a portion of the core member 1804 positioned within the lock cavity of the housing 1806 (and/or the openings in the housing 1806 through which the core member 1804 passes) and the second stop surface 1816 can be positioned at an oblique angle $\Theta$ relative to a portion of the core member 1804 positioned within the lock cavity of the housing 1806 (and/or the openings in the housing 1806 through which the core member 1804 passes). As discussed below, the angle of the second stop surface 1816 or the lock washer 1802 when contacting the second stop surface 1816 can be selected to achieve a desired lock or yield force or magnitude of resistance when the lock washer 1802 is in the lock position.

The housing 1806 can be coupled to one component of the interface assembly and the core member 1804 can be coupled to another component of the interface assembly such that relative movement between the housing 1806 and the core member 1804 occurs during extension or retraction of the headgear portion of the interface assembly during the fitment process. Frictional engagement between the core member 1804 and the lock washer 1802 moves the lock washer 1802 between the first and second positions depending on the direction of relative movement between the core member 1804 and the housing 1806 or retains the lock washer 1802 in one of the first and second positions depending on the direction of forces applied to the core member 1804 and/or housing 1806. Accordingly, with such an arrangement, the directional lock 1800 can be utilized to provide variable directional resistance characteristics in a self-fit interface assembly, similar to other embodiments described herein.

Figure 33:
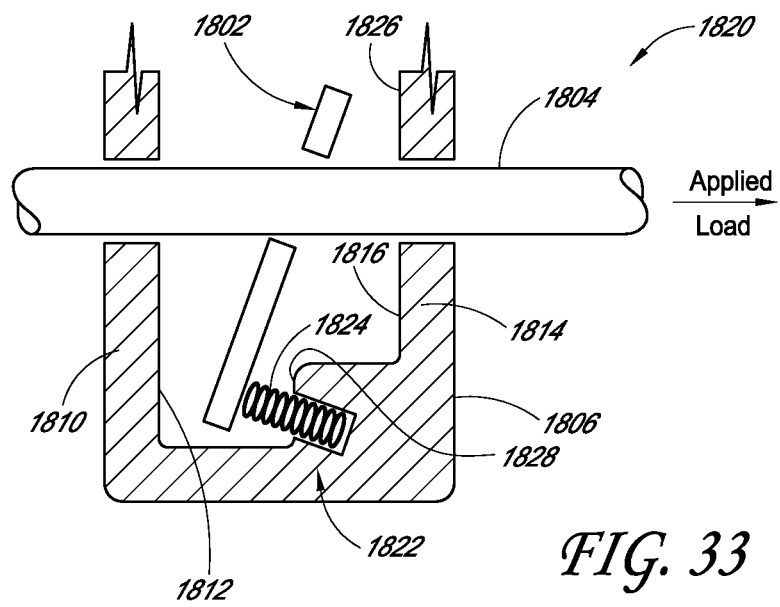
FIG. 33 illustrates a partial sectional view of a directional lock similar to the lock of FIG. 32. The directional lock of FIG. 33 includes a release mechanism that influences a slip force and provides a secondary lock position to the lock.

FIG. 33 illustrates a directional lock 1820 that is similar to the directional lock 1800. Accordingly, the same reference numbers or characters are used to indicate the same or corresponding components or features. The directional lock 1820 incorporates a release mechanism 1822 that releases the core member 1804 or reduces the resistance to movement of the core member 1804 upon a certain force being applied to the core member 1804 to limit the lock force of the directional lock 1820. That is, the release mechanism 1822 permits the lock washer 1802 to move from the lock position to a secondary lock position that is closer to perpendicular to the core member 1804 or closer to the release position, but in response to a force applied in a direction tending to move the lock washer 1802 to the lock position. Thus, the release mechanism 1822 influences to some extent the lock or yield force of the lock function of the directional lock 1802.

In the illustrated arrangement, the release mechanism 1822 comprises a biasing member or arrangement, such as a spring 1824. The spring 1824 supports the lock washer 1802 (along with a portion of the second surface 1816 of the housing 1806) in the lock position to inhibit or prevent relative movement between the core member 1804 and the housing 1806 in response to expected or normal operational forces. Preferably, the characteristics of the spring (e.g., spring rate, preload, etc.) are selected such that the lock washer 1802 can move against a biasing force of the spring 1824 toward or to the secondary lock position in response to a desired force magnitude, which can be greater than the expected or normal operational force (including one or more of blow-off forces, hose pull forces and a reserve). In the illustrated arrangement, the lock washer 1802 contacts the second surface 1816 of the housing 1806 substantially opposite of the spring 1824 in the lock position and pivots about that pivot surface or pivot point 1826 when moving toward the secondary lock position. The distance between the pivot point 1826 and the location of the spring 1824 (or effective location of any other biasing arrangement) can be referred to as the lever length of the lock washer 1802 and can influence the load necessary to move the lock washer 1802 from the lock position toward the secondary lock position. A portion 1828 of the second surface 1816 can define a stop that limits movement of the lock washer 1802 in a direction toward the secondary lock position (and, in some configurations, can define the secondary lock position). In the illustrated arrangement, the stop portion 1828 is located substantially opposite the pivot point 1826 and/or near the spring 1824.

There are a number of properties, characteristics or dimensions (e.g., materials or geometric shapes/proportions) that influence the activation length, lock strength and the durability of the directional lock mechanism 1800. Some of these can include the clearances between relative components (such as, for example, lock washer 1802 to core member 1804 or core member 1804 to housing 1806), the contact area between the lock washer 1802 and the core member 1804, the angle of the lock wall 1814 or lock surface 1816, or the force and lever length associated with the release mechanism 1822. In some configurations, a friction promoter is utilized to encourage initial engagement of the lock washer 1802 and the core member 1804. The friction promoter can be used to improve the initial lock activation. The friction promoter can be any achieved using any suitable technique, including but not limited to the use of a soft material to provide increased friction between the lock washer 1802 and the core member 1804, the use of a slightly angled release surface 1812 on the release wall 1810 of the lock chamber within the housing 1806, or the use of close tolerances between the hole in the lock washer 1802 and the core member 1804. In some configurations, the core member 1804 can have a diameter or cross-sectional dimension of between about 0.1 mm and about 8 mm, or any value or sub-range within that range. In some configurations, the core member 1804 may have a diameter or cross-sectional dimension greater than 8 mm.

Figure 34:
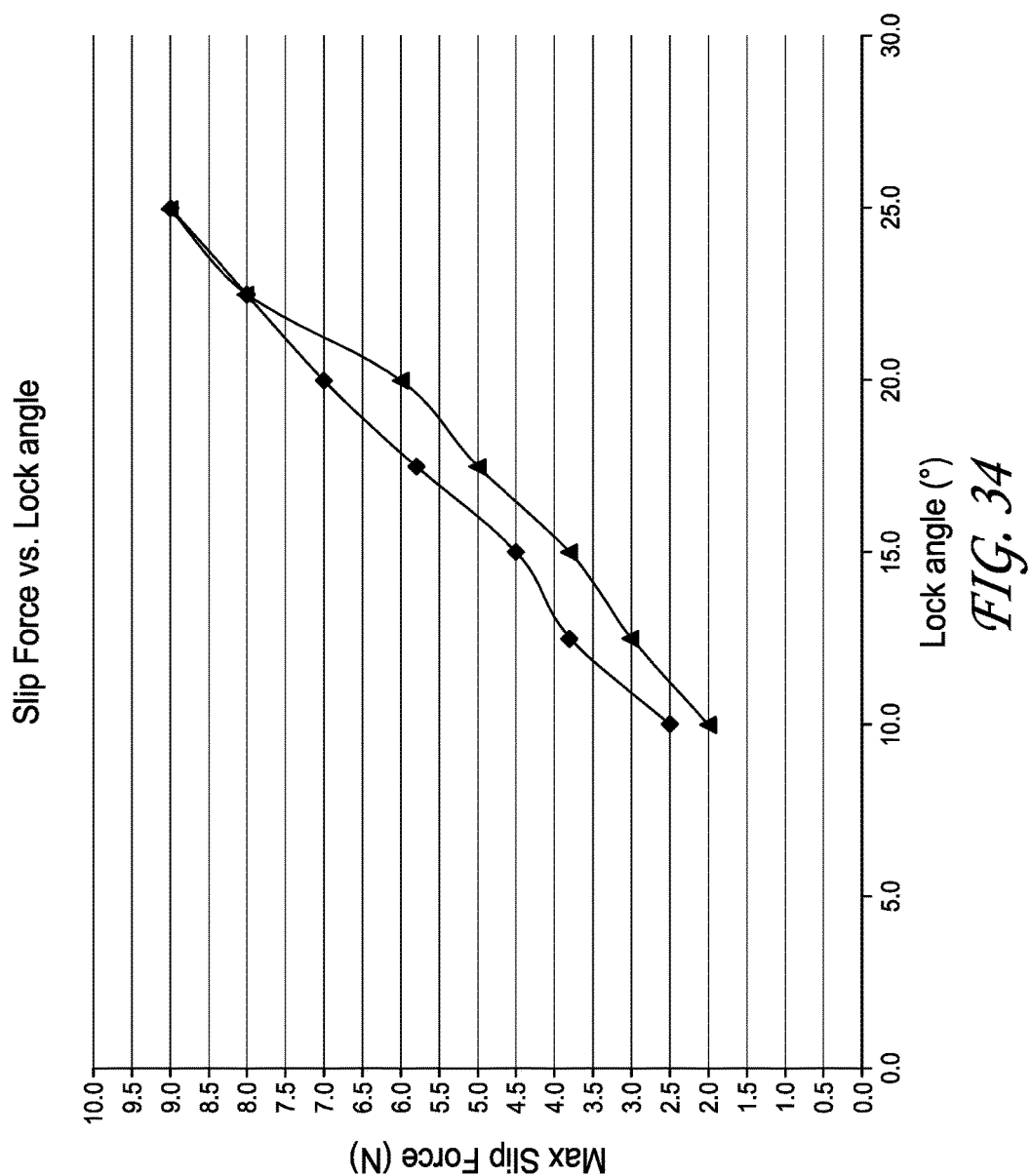
FIG. 34 is a graph that illustrates a relationship between a lock angle of the lock member and the slip force of a directional lock, such as the directional lock of FIGS. 32 and 33.

FIG. 34 illustrates a relationship between slip force and the lock angle of a directional lock (e.g., directional locks 1800 and 1820) that utilizes an angled lock member (e.g., lock plate or lock washer 1802). As illustrated, other factors being equal, the slip force required to achieve relative movement between the core member 1804 and the housing 1806 increases as the angle $\Theta$ of the lock washer 1802 in the lock position increases. In at least some configurations, the relationship is generally linear. By way of example, the graph of FIG. 34 illustrates the change in slip force for lock angles between 10 degrees and 25 degrees. The slip force varies from about 2-2.5 Newtons at 10 degrees to about 9 Newtons at 25 degrees with a generally linear relationship between those end points. The relationship between lock angle and slip force is one factor that can be utilized to achieve desirable lock and/or slip properties of a directional lock. The lock angles illustrated in FIG. 34 are merely exemplary. In some configurations, the lock angle can vary from just beyond zero degrees to about 45 degrees, or more. In some configurations, the lock angle is between about 10 degrees and about 25 degrees, as illustrated in the graph of FIG. 34, or any particular value or sub-range within that range. The slip force, or maximum lock force, for the directional lock 1800 or any other similar mechanism described herein, can be sufficient to inhibit undesired slip movement of the lock (e.g., as a result of blow-off forces or normal or expected external forces), but is not so great that desired slip movement of the lock (e.g., to permit application of the interface assembly) is prevented. As discussed herein, the slip force can be selected to be above the particular operational envelope for headgear application, which can be related to the type of interface to be used and/or the type of therapy, among other factors. In some configurations, the slip force is above the operational envelope by a reserve amount. In some configurations, the slip force can be less than or equal to about 65 Newtons, less than or equal to about 45 Newtons, less than or equal to about 25 Newtons, less than or equal to about 9 or 10 Newtons, or any particular value or sub-ranges within these ranges. In some configurations, the slip force can be at least about 0.5 Newtons. In some configurations, the slip force can be at least about 0.5 Newtons and less than or equal to about 9, 10, 25, 45 or 65 Newtons, or any particular value or sub-ranges within these ranges. In some configurations, the slip force can be about 0.5 Newtons to about 65 Newtons, about 1 Newton to about 45 Newtons, about 2 Newtons to about 25 Newtons, or about 2.5 Newtons to about 9 or 10 Newtons, or any particular value or sub-ranges within these ranges.

Figure 35:
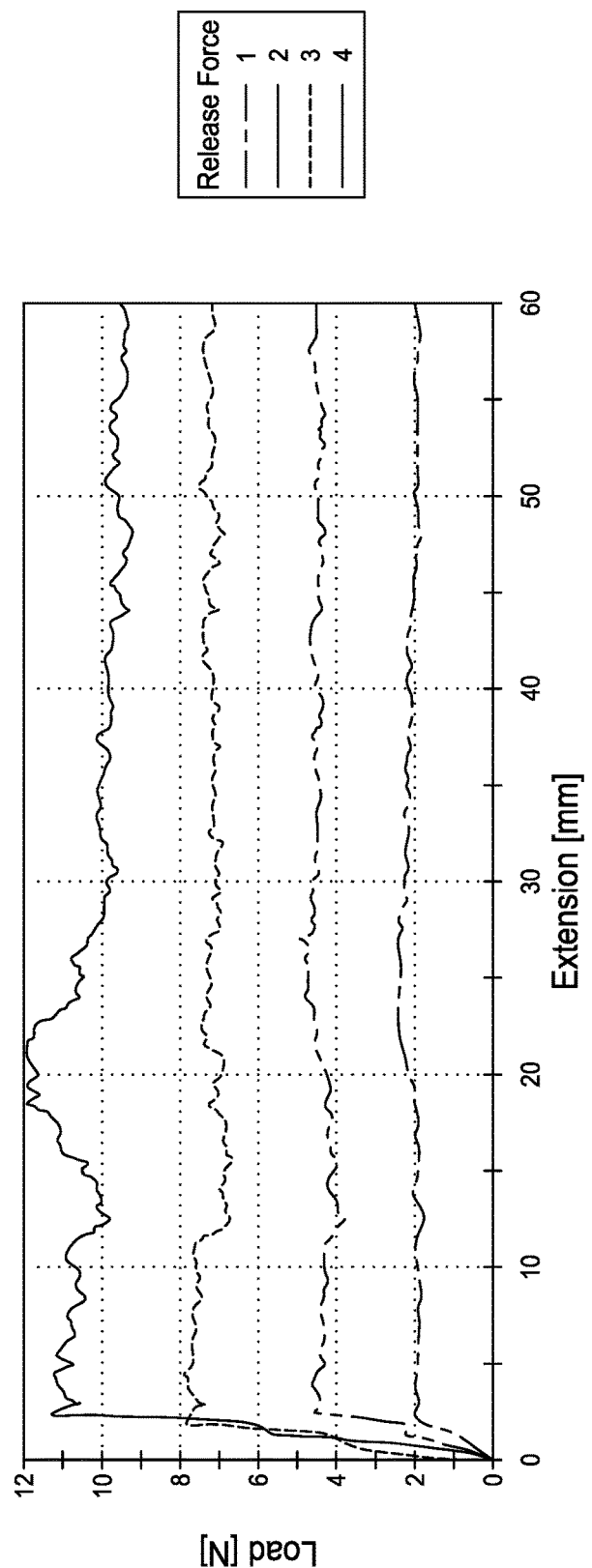
FIG. 35 is a graph that illustrates a variation in slip force that can result from variations in the release element in a directional lock having a secondary lock position, such as the directional lock of FIG. 33.

FIG. 35 illustrates variations in slip force that can be achieved with variations in the biasing arrangement 1824. Other characteristics being equal, the slip force can be varied by varying the characteristics of the biasing arrangement 1824 to increase or decrease the resistance to the lock washer 1802 move from the lock position toward the secondary lock position. For example, if the biasing arrangement comprises a spring 1824, the spring rate and/or preload can be selected to vary the slip force of the directional lock 1800, 1820. FIG. 35 illustrates four different variations in the biasing arrangement 1824 that results in four different slip forces (e.g., about 2 Newtons, about 4 Newtons, about 8 Newtons and about 10-11 Netwons). Such slip forces are only by way of example and can be adjusted to any suitable level. Although a compression coil spring is illustrated in FIG. 33, other suitable types of springs or spring-like elements (among other biasing arrangements) could also be used. In addition, the biasing arrangement 1824 could be adjustable post-manufacturing (e.g., by a caregiver or user) to allow the slip force to be adjusted after manufacturing, such as to accommodate user preference. For example, an adjustment mechanism could be provided that adjusts the preload on the spring 1828.

Figure 36:
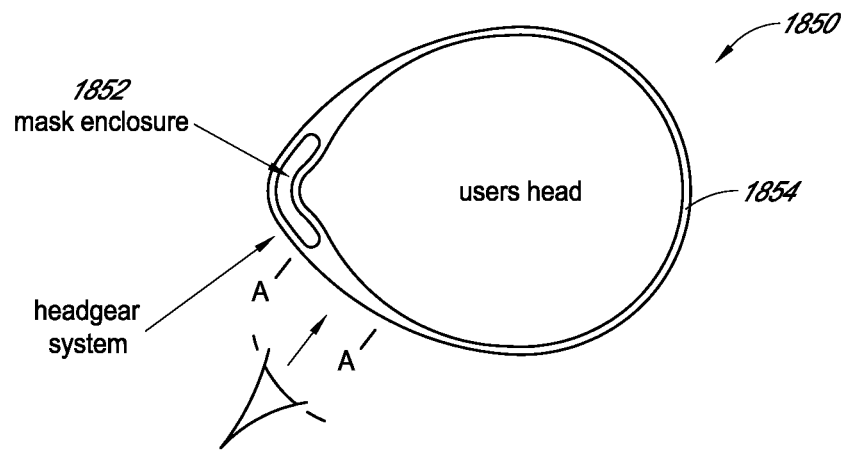
FIG. 36 is a sectional view of an interface assembly having a directional lock arrangement utilizing microstructures.
Figure 37:
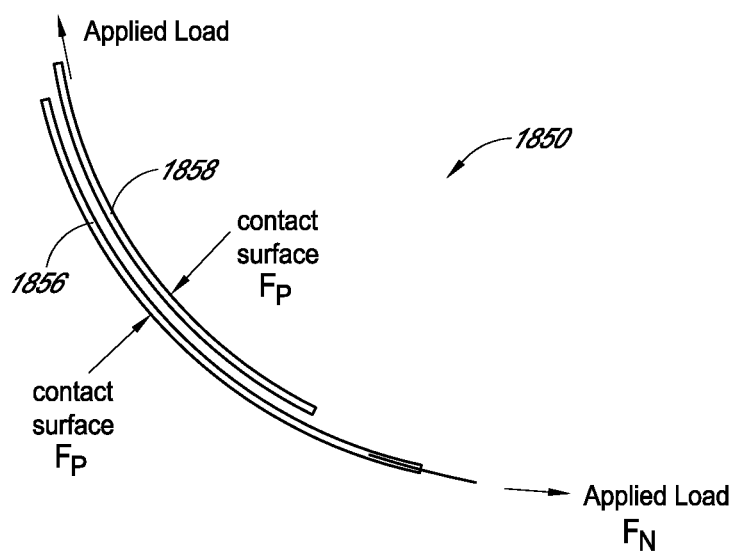
FIG. 37 is an enlarged view of a portion of the interface assembly of FIG. 36 illustrating two portions of the interface assembly that include microstructures.

FIGS. 36 and 37 illustrate a self-fit interface assembly 1850 exhibiting resistance on demand. The illustrated interface assembly 1850 provides directional locking functionality utilizing mechanical adhesion between a first portion of the assembly and a second portion of the assembly. Preferably, the interface assembly 1850 is constructed in a similar manner to interfaces described herein, such as those of FIGS. 7 and 8, in that two portions of the interface assembly 1850 interact to provide a first force in response to extension of the interface assembly 1850 and a second, preferably lower retraction force. However, the interface assembly 1850 of FIGS. 36 and 37 preferably provides such directional locking using microstructures on one or both portions that provide mechanical adhesion, mechanical interlocking, Van der Waal forces or other intermolecular forces.

With reference to FIG. 36, the interface assembly 1850 preferably includes an interface or mask portion 1852 and a headgear portion 1854. The mask portion 1852 preferably contacts the face of a user and creates at least a substantial seal with the user's face. The headgear portion 1854 extends around the user's head and supports the mask portion 1852 on the user's face. With reference to FIG. 37, a portion of the interface assembly 1850 is shown having a first portion 1856 and a second portion 1858 that are movable relative to one another to permit a length of the headgear portion 1854 to be varied. Each of the portions 1856 and 1858 can be defined by one or more of the mask portion 1852 or headgear portion 1854, or any other component of the interface assembly 1850. In some configurations, both portions 1856 and 1858 are defined by portions of the headgear portion 1854.

Preferably, one or both of the portions 1856 and 1858 include microstructures 1860 (FIGS. 38 and 39) that allow the portions 1856, 1858 to selectively engage one another and provide a directional locking force. Preferably, the locking force is sufficient to inhibit or prevent relative movement of the portions 1856, 1858, or maintain a current length of the headgear portion 1854, in response to expected or normal operational forces $F_N$, such as one or more of blow-off forces, hose pull forces, other external forces and a reserve. The locking force can be influenced by a force $F_P$ applied to the portions 1856, 1858 in a direction generally perpendicular to the direction of relative movement therebetween or in a generally radial direction if the interface assembly 1850 is considered as or in the general shape of a circle (such as when fitted on a user). Thus, the locking force can be increased when the user's head applied an outward force to the inner one of the portions 1856, 1858.

As described above in connection with other interface assemblies, the interface assembly 1850 can exhibit a first level of resistance to extension in the absence of a perpendicular or radial force on the portions 1856, 1858 and a second, preferably higher level of resistance to extension in the presence of a perpendicular or radial force on the portions 1856, 1858. Accordingly, the headgear portion 1854 can be stretched at the first level of resistance and then fitted to the user's head. Once fitted, the headgear portion 1854 can provide a second, higher level of resistance to extension, which acts to resist blow-off or other forces tending to extend the headgear portion 1854. Preferably, the force tending to resist retraction of the headgear portion 1854 (and, thus, the force applied to the user's head) is lower than at least the second level of resistance, and may be lower than the first level of resistance to extension, to improve user comfort.

Figure 38:
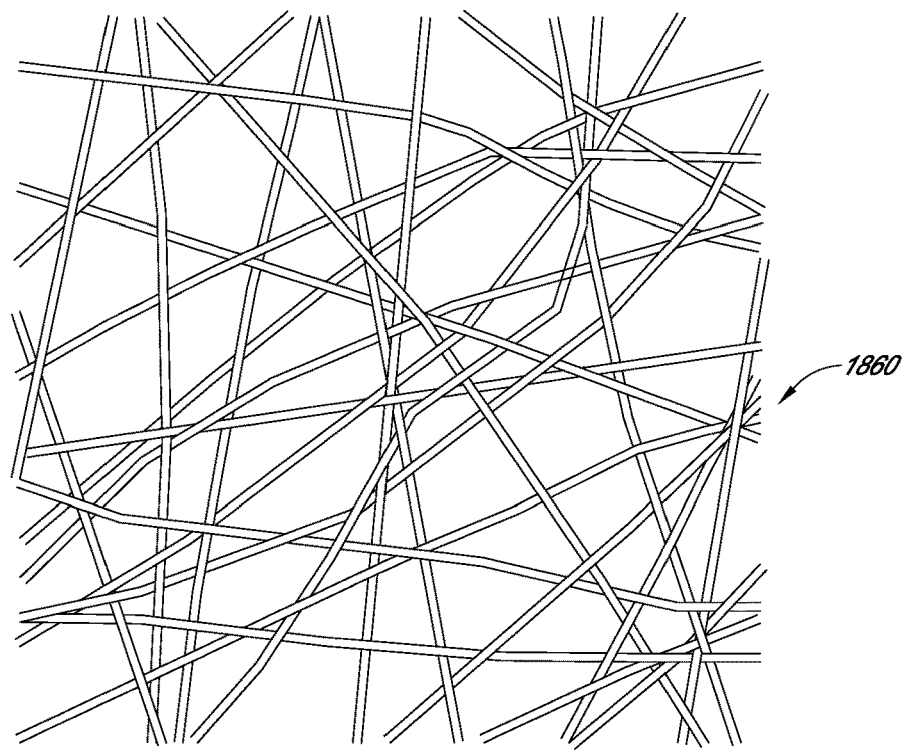
FIG. 38 is a view of microfibers or nanofibers that can be utilized as the microstructures in the interface assembly of FIGS. 36 and 37.

The microstructures 1860 can be of any suitable arrangement to provide a desired level of resistance to relative movement of the portions 1856, 1858 in either or both of extension and retraction. Preferably, in some configurations, the microstructures 1860 are directional or result in different levels or resistance depending on the direction of relative movement. As illustrated in FIG. 38, one suitable microstructure arrangement 1860 can comprise a plurality of fibers, such as microfibers or nanofibers, which can be produced using an electrospinning process and any suitable material, such a polymeric materials. Other suitable methods and/or materials may also be used. The fibers can be oriented in a suitable manner to provide directional properties, if desired.

Figure 39:
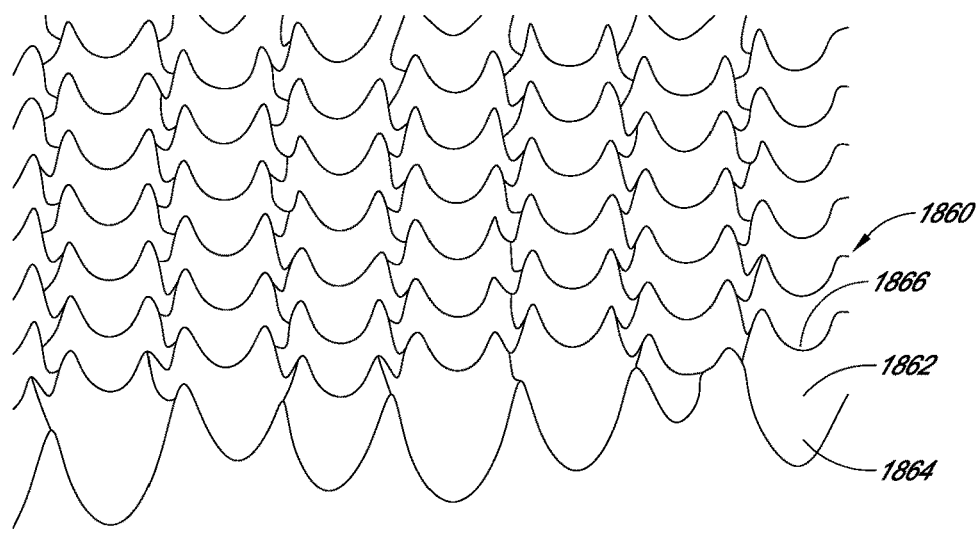
FIG. 39 is a view of a plurality of protrusions that can be utilized as the microstructures in the interface assembly of FIGS. 36 and 37.

As illustrated in FIG. 39, another suitable microstructure can comprise a plurality of geometric shapes, such as a plurality of ridges, teeth or scale-like protrusions 1862, for example. The protrusions 1862 can have a base 1864 and an edge 1866 that is generally opposite the base 1864. Each of the portions 1856, 1858 can employ such protrusions 1862 or one portion 1856, 1858 can employ protrusions 1862 and the other portion 1856, 1858 can employ other types of complementary structures that are suitable to engage the protrusions 1862. Preferably, the protrusions 1862 are oriented to provide the portions 1856, 1858 with directional locking or directional resistance to relative movement. For example, the protrusions 1862 could be oriented at an oblique angle relative to the surface on which the protrusions 1862 are supported and/or relative to the direction of movement. Thus, in response to movement in one direction, the protrusions 1862 could slide over one another with a lower level of resistance and, in response to movement in the other direction, the protrusions 1862 could engage one another to inhibit or prevent relative movement and provide a locking function. The protrusions 1862 can be arranged in any suitable manner (e.g., one or more rows). The protrusions 1862 can be constructed from any suitable material (e.g., polymer) by any suitable process (e.g., micro machining or micro molding techniques).

Figure 42:
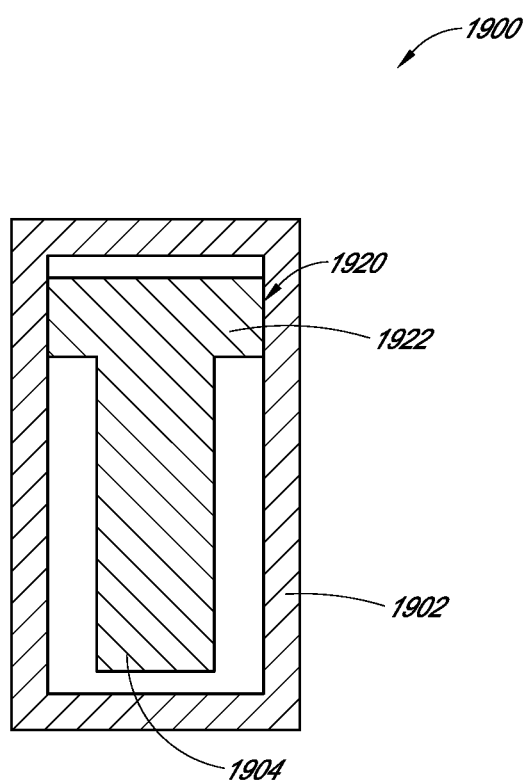
FIG. 42 is a sectional view of the lock plate and strap of the directional lock of FIG. 40 illustrating an activation mechanism that enhances engagement between the lock plate and the strap.

FIGS. 40-42 illustrate another adjustment mechanism 1900 having variable directional properties, which can be utilized in a self-fit interface assembly. The illustrated adjustment mechanism 1900 provides directional locking functionality and, thus, can be referred to as a directional locking mechanism or, simply, a directional lock. The directional lock 1900 of FIGS. 40-42 is similar in general operational principles to the arrangements of FIGS. 16, 21, 32 and 33 in that a lock component or member 1902 (e.g., lock plate) is movable between a first, lower resistance or release position and a second, higher resistance or lock position. Features or details not described with respect to the directional lock 1900 of FIGS. 40-42 can be the same as or similar to corresponding features of the arrangements of FIGS. 16, 21, 32 and 33, or can be of another suitable configuration.

The directional lock 1900 preferably includes a core member in the form of a flat strap 1904, which functions similar to the core member of the prior arrangements. The directional lock 1900 preferably also includes an enclosure or a housing 1906, which can be similar in construction and function to the housing of the prior arrangements. Thus, the lock plate 1902 is supported within the housing 1906 for movement between the first position and the second position. Preferably, the housing 1906 includes a first wall 1910 having a first stop surface 1912 that supports the lock plate 1902 in the first position, which preferably is the lower resistance or release position. The housing 1906 preferably also includes a second wall 1914 having a second stop surface 1916 that supports the lock plate 1902 in the second position, which preferably is the higher resistance or lock position.

Preferably, the lock plate 1902 is positioned generally perpendicular to a longitudinal axis of the strap 1904 positioned within the lock cavity of the housing 1906 in the first, lower resistance or release position such that the opening or hole of the lock plate 1902 is positioned generally parallel to or aligned with the strap 1904. Preferably, the lock plate 1902 is positioned at an oblique angle relative to the longitudinal axis of a portion of the strap 1904 positioned within the lock cavity of the housing 1906 in the second, higher resistance or lock position such that the opening or hole of the lock plate 1902 is positioned at an oblique angle to the strap 1904. Thus, in some configurations, the first stop surface 1912 can be generally perpendicular to the strap 1904 positioned within the lock cavity of the housing 1906 (and/or the openings in the housing 1906 through which the strap 1904 passes) and the second stop surface 1916 can be positioned at an oblique angle Θ relative to the strap 1904 (and/or the openings in the housing 1906 through which the core member 1904 passes). As discussed below, the angle of the second stop surface 1916 or the lock plate 1902 when contacting the second stop surface 1916 can be selected to achieve a desired maximum lock force or magnitude of resistance when the lock washer 1902 is in the lock position. If desired, a release mechanism can be provided similar to the release mechanism 1822 of FIG. 33.

As in the prior arrangements, the strap 1904 can be coupled to or form a first portion of the associated interface assembly and the housing 1906 can be coupled to or form a second portion of the interface assembly such that a length or circumference of the interface assembly can be adjusted by relative movement of the strap 1904 and the housing 1906. Advantageously, the strap 1904 is anisotropic with respect to one or more properties. For example, the strap 1904 is more flexible when flexing or bending in a width direction than when bending in a height direction. Accordingly, the strap 1904 can flex in a direction to conform to the user's head, but resists flex in the height direction to provide support to the interface assembly and inhibit undesired movement of the mask portion. In addition, the directional lock 1900 comprising the strap 1904 is well-suited for use in portions of the interface assembly that contact the user's head, such as sides, rear or top portions of the headgear strap, for example, with possibly greater comfort than interfaces having generally cylindrical core members. However, the directional lock 1900 can also be used in other portions or locations of the interface assembly, such as on one or both side portions of the headgear between the portions than contact the user's head and the mask portion.

The illustrated directional lock 1900 includes an activation mechanism 1920 that facilitates movement of the lock plate 1902 to increase the sensitivity of the directional lock 1900. Such an activation mechanism 1920 can hasten movement of the lock plate 1902 to or from a lock position or a release position to improve the time or distance of relative movement required to transition between a lock position and a release position of the directional lock 1900. In addition or in the alternative, the activation mechanism 1920 can decrease the sensitivity of the directional lock 1900 to variations in component dimensions (e.g., dimensions of interacting portions of the lock plate 1902 or strap 1904) such that the component tolerances can be greater, while maintaining a desirable level of functionality, thereby reducing the cost of the directional lock 1900.

In some configurations, one of the lock plate 1902 and the strap 1904 can include an engagement feature 1922 that facilitates engagement with the other of the lock plate 1902 and the strap 1904. In the illustrated arrangement, the strap 1904 includes an engagement feature 1922 that facilitates frictional engagement with the lock plate 1902. The engagement feature 1922 can comprise a portion of the strap 1904 having particular dimensions, surface features or materials that enhance engagement with the lock plate 1902. For example, with reference to FIG. 42, a width of the engagement feature 1922 can be greater than a width of a remainder of the strap 1904. In addition or in the alternative, the engagement feature 1922 can comprise a different material or surface finish that has improved frictional characteristics relative to a remainder of the strap 1904 to enhance frictional engagement between the lock plate 1902 and the strap 1904. In the illustrated arrangement, the engagement feature 1922 is a silicone material portion that is keyed to the remainder of the strap 1904, which can be constructed of a suitable plastic material. However, other suitable materials can also be used for the engagement feature 1922 or the remainder of the strap 1904. The mechanical interference between the interacting lobes of the engagement feature 1922 and the remainder of the strap 1904 inhibits separation of the different materials. Other suitable arrangements, materials or constructions of the strap 1904 having an engagement feature 1922 can also be used.

Preferably, the engagement feature 1922 acts on a different surface(s) of the lock plate 1902 than a surface(s) that provides a primary locking function. For example, because the engagement feature 1922 has an increased width relative to the remainder of the strap 1904, the engagement feature 1922 acts substantially or primarily on side (height) surfaces of the strap 1904 while the substantial or primary locking function is accomplished by the top and bottom (width) surfaces. At least partial separation of the locking and engagement functionalities permits each to be optimized separately. Thus, the sensitivity of the directional lock 1900 can be varied to achieve a desired level of sensitivity and the lock force can be separately varied to achieve a desired level of locking without causing a substantial negative impact on one another.

Figure 43:
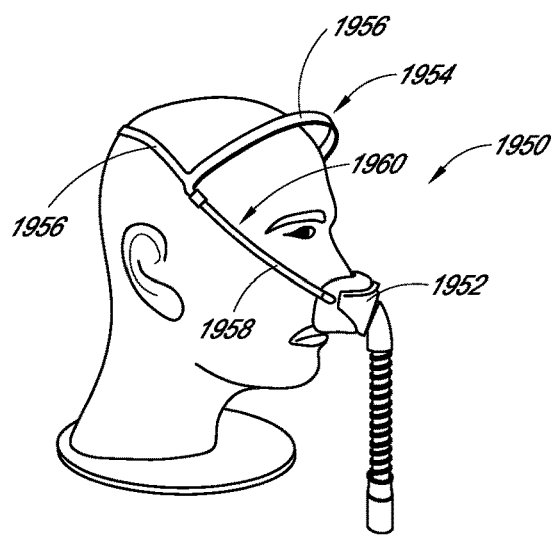
FIG. 43 is a perspective view of an interface assembly incorporating at least one directional lock arrangement being applied to a user.
Figure 44:
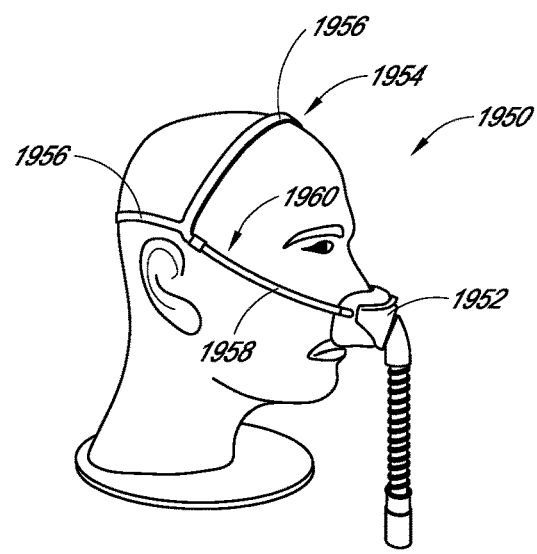
FIG. 44 is a perspective view of the interface assembly of FIG. 43 in a position that is closer to a fully fitted position.
Figure 45:
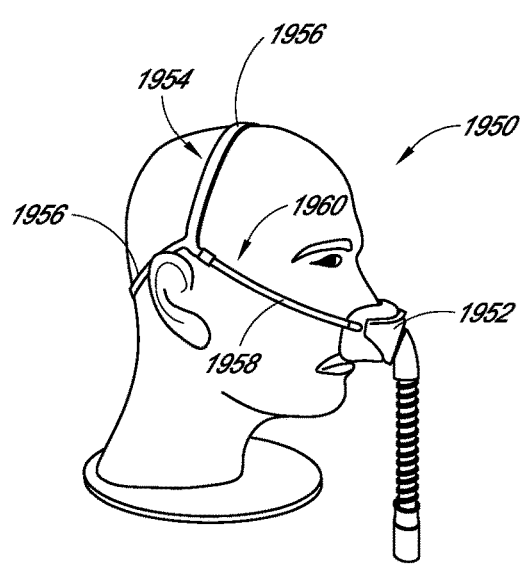
FIG. 45 is a perspective view of the interface assembly of FIG. 43 fitted to the user.

FIGS. 43-45 illustrate an interface assembly 1950 having self-fit functionality similar to other interface assemblies described herein. FIGS. 43-45 illustrate the interface assembly 1950 in various positions within a fitment process. FIG. 43 illustrates the interface assembly 1950 partially fitted to a user. FIG. 45 illustrates the interface assembly 1950 fully fitted to a user and FIG. 44 illustrates the interface assembly 1950 in between the positions of FIGS. 43 and 45.

In general, the interface assembly 1950 comprises an interface portion 1952, such as a mask, and a headgear portion 1954. The headgear portion 1954 can include a rear portion 1956 that contacts the user's head and includes one or more straps. In the illustrated arrangement, the rear portion 1956 includes multiple straps: one that passes around the rear of the head and one that passes over the crown of the head. However, any suitable number of straps can be provided. The headgear portion 1954 also includes a pair of side straps 1958 that extend between and preferably connect the rear portion 1956 and the mask 1952. In the illustrated arrangement, each of the side straps 1958 comprises a portion or all of a directional locking arrangement 1960, which provides or otherwise facilitates the self-fit functionality. Optionally, the mask 1952 can carry or include a portion of the directional locking arrangement 1960. In other arrangements, other portions of the interface assembly 1950 (e.g., the rear portion 1956 of the headgear portion 1954 and/or the mask 1952) can include a portion or an entirety of a directional locking arrangement, in addition or in the alternative to the side straps 1958. Each side strap 1958 can be substantially similar or identical in construction and operation.

As described above in connection to other interface assemblies, preferably the interface assembly 1950 provides self-fit or directional functionality in that it permits the interface assembly 1950 to extend for application, retract to adjust to the particular user's head size and then lock to inhibit or prevent extension in response to expected or normal forces, such as one or more of CPAP blow-off forces, hose pull forces and a reserve. Preferably, the directional lock 1960 has lower resistance to forces tending to retract the interface assembly 1950, headgear portion 1954 or side strap 1958 and a higher resistance to forces tending to extend the interface assembly 1950, headgear portion 1954 or side strap 1958 such that the retention force applied to the user's head by the interface assembly 1950 is less than the locking force that inhibits extension of the interface assembly 1950. In some configurations, the retention force is below the operational envelope for the interface assembly 1950 and the locking force is above the operational envelope, as described herein with reference to FIGS. 2-5.

FIGS. 46-48 illustrate the directional lock arrangement 1960 incorporating the side strap 1958 separate from the interface assembly 1950 of FIGS. 43-45. The directional lock arrangement 1960 generally comprises a lock portion or lock 1962, a core member 1964 and an elastic strap 1966. The elastic strap 1966 and at least a portion of the core member 1964 form at least a portion of the side strap 1958. The lock 1962 can form a portion of the side strap 1958 and, preferably, attaches to the mask 1952 or can be a portion of the mask 1952.

The core member 1964 can be connected at one end to the elastic strap 1966. Preferably, the core member 1964 passes through the lock 1962. A free end of the core member 1964 can be positioned within a conduit or tube 1968, which can reside in, be carried by or be formed by the mask 1952. The elastic sleeve 1966 preferably provides a force tending to push the core member 1964 through the lock 1962 in a direction such that a larger portion of the core member 1964 resides in the tube 1968. Therefore, the elastic sleeve 1966 (or the pair of elastic sleeves 1966 assuming a pair of side straps 1958) preferably provides some or all of a force tending to retract the interface assembly 1950. Preferably, the core member 1964 has sufficient stiffness or column strength to be pushed through the lock 1962 without significant buckling. In some configurations, other retraction mechanisms could be provided to provide a retraction force in addition or in the alternative of the elastic strap(s) 1966. For example, a biasing element could be coupled to a free end of the core member 1964 to pull the core member 1964 through the lock 1962, which could provide all of the retraction force (in which case the strap 1966 could be omitted or could be non-elastic) or could operate in concert with the elastic strap 1966. In some configurations, a biasing element could connect the free ends of both core members 1964 to provide some or all of the retraction force to both of the side straps 1958. In still further configurations, the associated headgear may not provide a retraction force. For example, the headgear may be manually retracted to a desired circumference to fit the user's head.

The lock 1962 operates in accordance with the general principles described above with reference to other directional locking arrangements, such as those of FIGS. 16, 21, 32, 33 and 40-42. Accordingly, details not discussed in connection with FIGS. 46-48 can be assumed to be similar or identical to the same or corresponding features in those arrangements, or can be of any other suitable arrangement.

The lock 1962 preferably includes a housing 1970 and a lock member or lock element 1972. In the illustrated arrangement, the lock element 1972 is formed as unitary structure of single piece with at least a portion of the housing 1970 and, preferably, with portions that define the openings through which the core member 1964 passes through the housing 1970. The housing 1970 may have additional portions that, for example, enclose or protect the lock element 1972 or facilitate attachment to the mask 1952 and/or the elastic strap 1966.

The lock element 1972 functions in manner similar to the lock members (e.g., lock washers and lock plates) described elsewhere herein. That is, preferably the lock element 1972 defines an opening through which the core member 1964 passes. The lock element 1972 is moveable between a release position and a lock position to vary a resistance to movement of the core member 1964 relative to the housing 1970. Preferably, the resistance to movement of the core member 1964 tending to extend the length of the elastic strap 1966 is greater than the resistance to movement of the core member 1964 tending to retract the length of the elastic strap 1966. Accordingly, the retraction force provided by the elastic strap 1966 (or other components of the interface assembly 1950) can be relatively light or of a relatively low magnitude to improve patient comfort and the lock element 1972 can permit the interface assembly 1950 to resist extension without reliance on the force produced by the elastic strap 1966. Thus, the retention force of the elastic strap 1966 can be tuned for patient comfort without needing to handle blow-off or other external forces tending to extend the interface assembly 1950.

Similar to the arrangements described elsewhere herein, preferably, surfaces of the lock element 1972 that define or surround the opening through which the core member 1964 passes engages the core member 1964 in the lock position to provide a level of resistance to movement of the core member 1964 to inhibit or prevent extension of the elastic strap 1966. However, instead of being controlled by surfaces of the housing, the lock element 1972 is coupled to the housing 1970 by a curved portion or a living hinge 1974 and the movement of the lock element 1972 is controlled by the properties of the living hinge 1974. That is, the lock element 1972 and the living hinge 1974 are defined by a curved arm portion that extends from the housing 1970 and has a free end. A relaxed position of the lock element 1972 can define the release position, which may be influenced by the presence of the core member 1964 passing through the lock element 1972. That is, the release position may not be the same as the relaxed position of the lock element 1972 in an unassembled state without the core member 1964. Movement or attempted movement of the core member 1964 in a direction tending to extend the length of the elastic strap 1966 (to the left in the illustrated orientation) deflects the lock element 1972 toward the lock position to inhibit or prevent extension of the elastic strap 1966. The dimensions, material properties or other characteristics of the living hinge 1974 influence the lock force of the lock 1962. In some configurations, the lock force is related to the angle of the lock element 1972, as described elsewhere herein (see, for example, FIG. 34 and the related disclosure).

In some configurations, limited movement of the core member 1964 can occur as the lock element 1972 transitions from the release position to the lock position. Accordingly, the retraction force provided by the elastic strap 1966 (or other biasing element(s)) preferably provides a force sufficient to maintain at least a substantial seal of the mask 1952 or other interface after movement of the core member 1964 as a result of the lock element 1972 moving to the lock position. Preferably, the lock 1962 is configured such that the distance that the core member 1964 is permitted to move is relatively small.

FIGS. 46-48 illustrate the directional lock arrangement 1960 in various positions. FIG. 46 illustrates the directional lock arrangement 1960 in a relaxed or resting position in which the elastic strap 1966 is retracted and has pushed a maximum amount of the core member 1964 into the tube 1968. The lock element 1972 is in the release position.

FIG. 47 illustrates the directional lock arrangement 1960 in an extended position, which could occur during the application phase of the fitment process. The extension of the elastic strap 1966 has pulled a portion of the core member 1964 out of the tube 1968 against resistance offered by the lock 1962 as a result of the lock element 1972 moving to or toward the lock position such that a minimum amount of the core member 1964 is located within the tube 1968. Once the extended position has been reached and relative movement between the housing 1970 and the core member 1964 has ceased, the lock element 1972 may remain in the lock position, may return to the release position or may be positioned somewhere in between depending on a variety of factors, such as the spring force of the living hinge 1974, the relative proportions of the core member 1964 and the opening in the lock element 1972 and the frictional force between the core member 1964 and the lock element 1972.

FIG. 48 illustrates the directional lock arrangement 1960 in an operational position having a length between the relaxed position and the extended position, such as when fitted on the head of a user. Compared to the extended position, the retention force of the elastic strap 1966 has pushed a greater amount of the core member 1964 into the tube 1968 in the operational position against resistance offered by the lock element 1972 in the release position, which preferably is substantially lower than the resistance to extension. The lock element 1972 can be in the lock position, the release position or may be positioned somewhere in between, as described above. However, in response to extension of the directional lock arrangement 1960 or forces tending to extend the directional lock arrangement 1960, the lock element 1972 moves to or remains in (depending on the initial position) the lock position to provide resistance to extension due to expected or normal operational forces. The directional lock arrangement 1960 can be further extended in response to, for example, user-applied force to allow the interface assembly 1950 to be removed.

Figure 49:
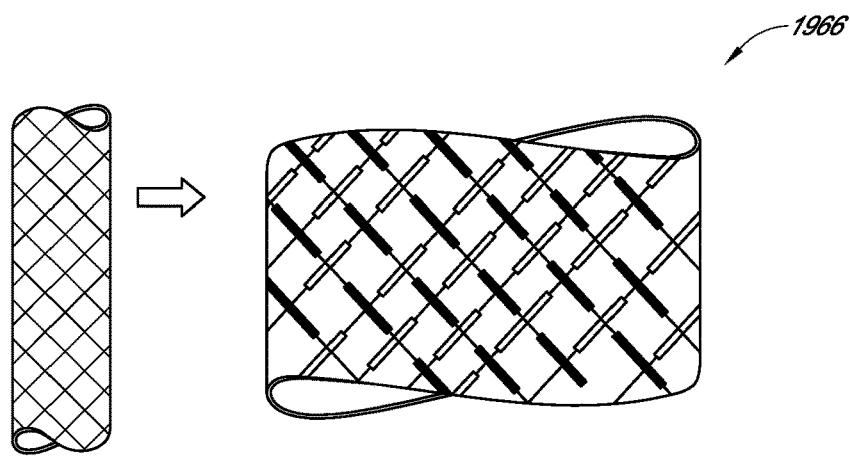
FIG. 49 illustrates a portion of a braid that forms an elastic strap of the directional lock arrangement of FIGS. 46-48.
Figure 50:
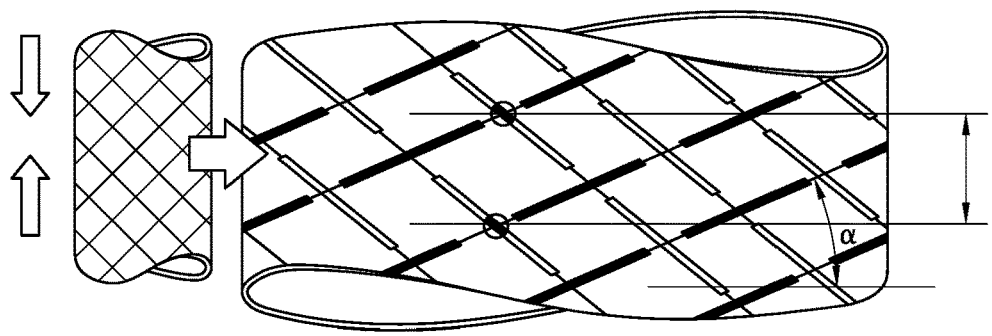
FIG. 50 illustrates the braid of FIG. 49 in a compressed position.
Figure 51:
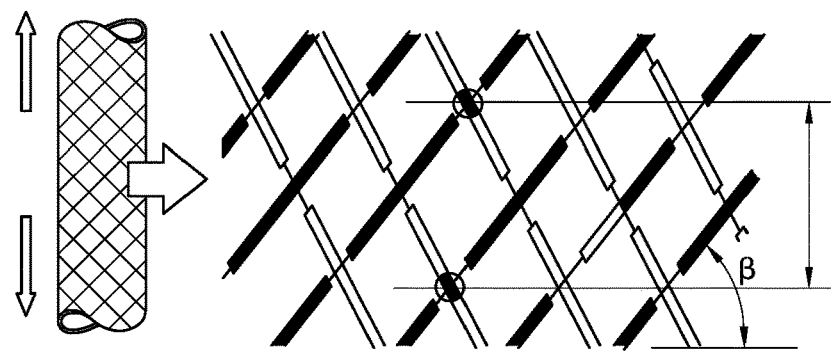
FIG. 51 illustrates the braid of FIG. 49 in an extended position.

FIGS. 49-51 illustrate a portion of the elastic strap 1966 of the directional lock arrangement 1960 of FIGS. 46-48. The illustrated elastic strap 1966 is of a tubular construction and includes an interior passage, which can accommodate the core member 1964. Thus, the core member 1964 can move within the elastic strap 1966 without rubbing against the user or other objects. Preferably, the elastic strap is a braid of multiple individual strands or yarns (fibers) of any suitable material in any suitable type of weave. The individual fibers can be woven such that adjacent fibers or groups of fibers have a particular initial angled orientation relative to one another, as illustrated in FIG. 49. Preferably, the initial angled orientation permits the braid can be compressed and extended relative to the initial angled orientation, as illustrated in FIGS. 50 and 51, respectively. Thus, the initial angled orientation can be described as an intermediate angled orientation. The amount of compression and extension relative to the initial orientation can be the same or can be different from one another.

Preferably, as described above, the strap 1966 includes a biasing arrangement that biases the strap 1966 toward or to the compressed position. Accordingly, the strap 1966 is referred to as an elastic strap 1966. The biasing arrangement can be of any suitable construction, such as incorporating one or more elastic fibers within the braid. Preferably, the maximum extension of the braid is selected to be less than the maximum extension (or other range of movement) of the biasing arrangement to avoid damage to the biasing arrangement upon maximum extension. In some configurations, the braid limits maximum extension of the biasing arrangement from reaching plastic deformation and maintains the range of extension movement within the elastic range of movement of the biasing arrangement, such as elastic elongation of the elastic fibers. The braid can also provide an end stop to movement of the core member 1964 to prevent the core member 1964 from being pulled through the lock 1962. That is, preferably, in full extension of the braid, a portion of the core member 1964 remains within the lock 1962.

Figure 52:
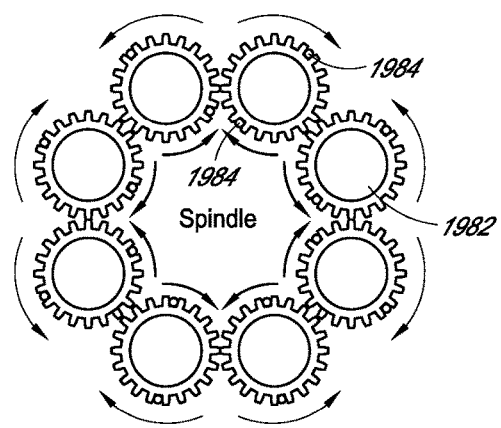
FIG. 52 illustrates a machine and method for creating the braid of FIG. 49.
Figure 53:
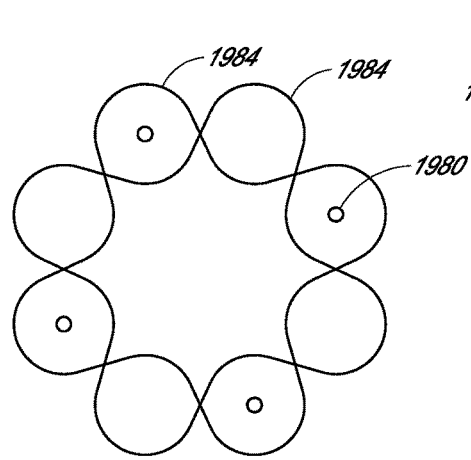
FIG. 53 is a sectional view of a braid incorporating elastic fibers.
Figure 54:
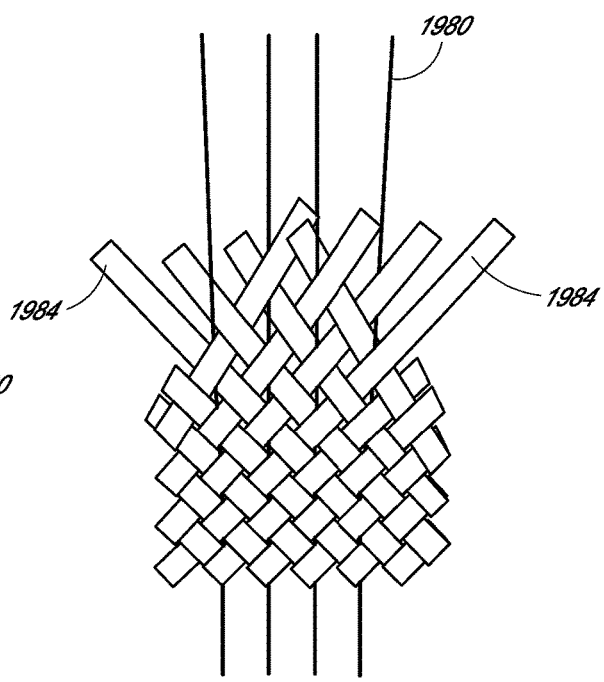
FIG. 54 is a view of the braid of FIG. 53 in a flattened orientation.

With reference to FIGS. 52-54, in some configurations, one or more elastic fibers 1980 can be integrated into the braid during the weaving process. FIG. 52 is a schematic illustration of a machine and process for creating the braided elastic strap 1966. The machine includes multiple spindles 1982 having a plurality of cavities defined between radial projections or teeth. Adjacent spindles 1982 rotation in opposite directions as indicated by the arrows and pass a preferably relatively inelastic fiber or groups of fibers 1984 from one spindle 1982 to the next. Another fiber or group of fibers 1984 move from one spindle 1982 to the next in the opposite direction to weave the two fibers or groups of fibers 1984 together. Elastic fibers 1980 can be passed through the centers of the spindles 1982 such that the elastic fibers 1980 are integrated into the braid, as illustrated in FIG. 53. FIG. 54 illustrates the elastic strap 1966 if the tubular member were cut in a longitudinal direction and laid flat.

Figure 55:
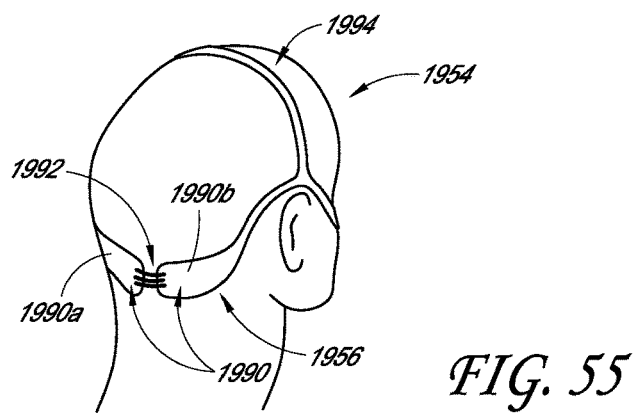
FIG. 55 is a rear perspective view of a rear portion of a headgear assembly having an interrupted strap arrangement fitted on a user.

FIG. 55 illustrates a rear portion 1956 of a headgear assembly 1954 that can be used with the interface assembly 1950, other interface assemblies disclosed herein or any other suitable interface. The rear portion 1956 of the headgear assembly 1954 illustrated in FIG. 55 comprises a lower rear section 1990 in the form of an interrupted or segmented strap that separates a load or provided a non-uniform load acting on the user's head, in contrast to a non-segmented strap that places a load across an entire length of the strap. That is, the lower rear section 1990 has a first portion 1990*a* and a second portion 1990*b*, which preferably are interrupted and/or spaced apart and can be connected by a coupling 1992, such as one or more straps or laces or a weakened portion of the section 1990. The coupling 1992 can be relatively or substantially inelastic to substantially fix a relative position of the first portion 1990*a* and the second portion 1990*b* relative to a longitudinal axis of the section 1990 (the length of the section 1990), but can permit relative movement of the first portion 1990*a* and the second portion 1990*b* in a perpendicular or rotational direction relative to the longitudinal axis. Such an arrangement can be referred to as an articulable connector. Preferably, the first portion 1990*a* and the second portion 1990*b* form occipital pads that engage the user's head on or near the occipital bone. A space between the first portion 1990*a* and the second portion 1990*b* can be located generally at the occipital protuberance in a circumferential direction and the lower real section 1990 can be at or below the occipital protuberance in a height direction. Preferably, the rear portion 1956 also comprises an upper rear section 1994 that extends over the crown of the user's head. Ends of the lower rear section 1990 and the upper rear section 1994 join one another at a location generally above each ear of the user.

Figure 56:
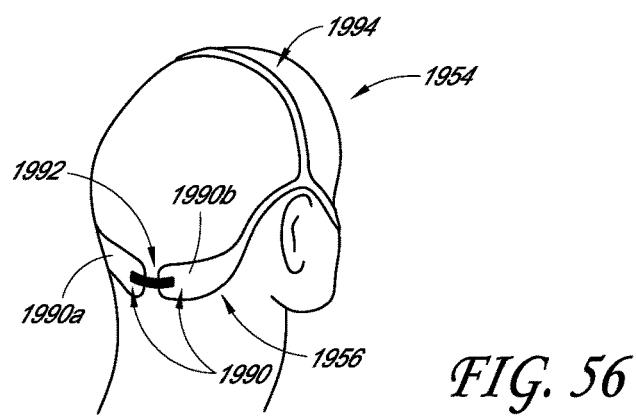
FIG. 56 is a rear perspective view of a rear portion of a headgear assembly having an interrupted strap arrangement fitted on a user, in which portions of the strap are coupled by an articulable coupling.

FIG. 56 illustrates a rear portion 1956 of a headgear assembly that is similar to the rear portion 1956 of FIG. 55. Accordingly, details of the rear portion 1956 of FIG. 56 not discussed can be assumed to be the same as or similar to the corresponding elements of the rear portion 1956 of FIG. 55, or can be of any other suitable arrangement. The coupling 1992 of the rear portion 1956 of FIG. 56 comprises an articulable connector, such as a material strap, which can be elastic or substantially inelastic. Preferably, the coupling 1992 permits relative rotational movement between the first portion 1990*a* and the second portion 1990*b* about a longitudinal axis of the strap to allow the lower rear section 1990 to better conform to the shape of the user's head, in particular, the occipital bone geometry.

Advantageously, the rear portions 1956 of FIGS. 55 and 56 provide comfort for the user while also securing the mask or other patient interface in place on the user's head. The interrupted lower rear section 1990 avoids placing excessive pressure on the occipital protuberance. Such an interrupted arrangement can also or alternatively be provided in the upper rear section 1994. Either of the rear portions 1956 of FIGS. 55 and 56 could also incorporate one or more directional lock assemblies, such as any of those disclosed herein. For example, the coupling 1992 could be configured as a directional lock assembly. A directional lock assembly could also be integrated into either or both of the lower rear section 1990 and the upper rear section 1994. For example, the flat strap arrangement of FIGS. 40-42 could be integrated into either or both of the first portion 1990*a* and the second portion 1990*b*.

Figure 57:
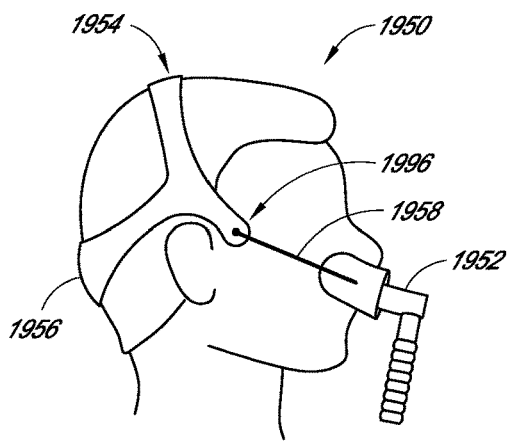
FIG. 57 is a side view of an interface assembly fitted on a user and having a side strap between a rear portion of the headgear assembly and the user interface.
Figure 58:
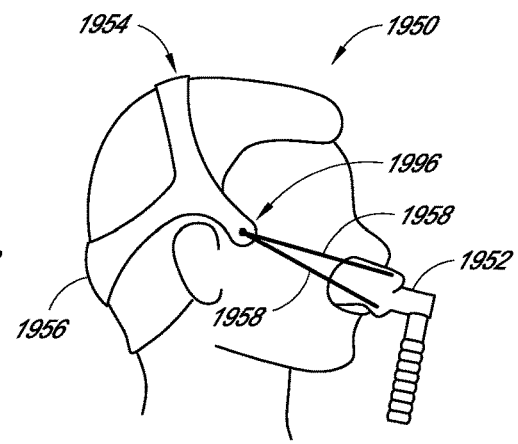
FIG. 58 is a side view of an interface assembly fitted on a user and having a pair of side straps between a rear portion of the headgear assembly and the user interface in a triangulated arrangement.

FIGS. 57 and 58 illustrate two versions of an interface assembly, which can be substantially similar to the interface assembly 1950 and related components described in connection with FIGS. 43-56. Accordingly, details of the rear portion interface assemblies 1950 of FIGS. 57 and 58 not discussed can be assumed to be the same as or similar to the corresponding elements of the interface assembly 1950 and related components described in connection with FIGS. 43-56, or can be of any other suitable arrangement. In each interface assembly 1950, each side strap 1958 (which can incorporate a directional lock or can be a fixed length) is coupled to the rear portion 1956 of the headgear assembly 1954 at a point 1996 located near the user's ear. Preferably, the point 1996 is located forward of the ear and at (e.g., generally in line with) or near the upper location at which the outer ear is joined to the head (the top of the base of the outer ear). The side strap 1958 extends from the point 1996 to the mask 1952 or other interface. In the interface assembly 1950 of FIG. 57, a single side strap 1958 on each side of the interface assembly 1950 extends from the point 1996 to the mask 1952. In the interface assembly 1950 of FIG. 58, a pair of side straps 1958 on each side of the interface assembly 1950 extends from the point 1996 to spaced-apart locations on the mask 1952 to provide a triangulated arrangement, which in at least some cases increases the stability of the mask 1952. Preferably, a rearward projection of the side strap(s) 1958 passes between the upper and lower straps of the rear portion 1956 of the headgear assembly 1954 such that loads are divided between the upper and lower straps. Examples and further details of such an arrangement are disclosed in Applicant's U.S. Patent Publication No. 2013/0074845, the entirety of which is incorporated by reference herein. As discussed above, if desired, one or more directional locks can be incorporated into the interface assemblies 1950 of FIGS. 57 and 58 at any suitable location, such as those described herein.

In any of the headgear embodiments described above, additional straps could be included to provide additional stability, such as but not limited to a crown strap or additional back strap.

Figure 59:
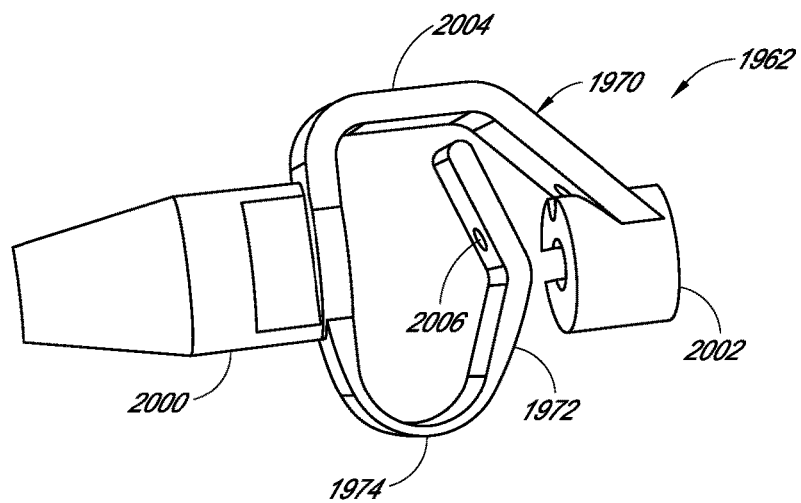
FIG. 59 is a side view of a lock arrangement similar to that of FIGS. 46-48, which can form a portion of a modular directional lock arrangement.

FIG. 59 illustrates a lock arrangement 1962 that is substantially similar to the lock arrangement 1962 of FIGS. 46-48. Accordingly, details of the lock arrangement 1962 of FIG. 59 not discussed can be assumed to be the same as or similar to the corresponding elements of the lock arrangement 1962 of FIGS. 46-48, or can be of any other suitable arrangement. The lock arrangement 1962 of FIG. 59 is a modular design that allows directional locking technology to be easily incorporated into a range of respiratory masks or other user interfaces.

The lock arrangement 1962 includes a housing or body portion 1970, a locking element 1972 and a living hinge 1974 that connects the locking element 1972 to the body portion 1970. The body portion 1970 includes a first end portion 2000 and a second end portion 2002. A generally U-shaped connecting bridge 2004 extends between the first end portion 2000 and the second end portion 2002 and provides space therebetween to accommodate the locking element 1972. Preferably, each end portion 2000, 2002 is generally tubular or cylindrical in shape and defines a longitudinal passage that accommodates a core member. The locking element 1972 also includes a hole 2006 that permits passage of the core member. Preferably, the end portions 2000, 2002, the connecting bridge 2004, the locking element 1972 and the living hinge 1974 are of a one-piece construction.

Figure 60:
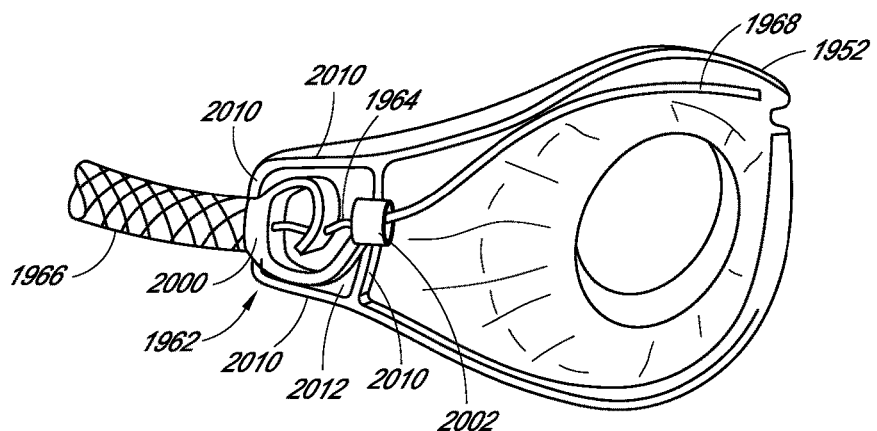
FIG. 60 is a perspective view of the lock arrangement of FIG. 59 assembled to a mask.

FIG. 60 illustrates the lock arrangement 1962 of FIG. 59 incorporated into a patient interface assembly, such as a mask 1952. The illustrated mask 1952 includes walls 2010 defining a pocket 2012, which receives the lock arrangement 1962. The walls 2010 can include recesses or openings that receive the end portions 2000, 2002 of the lock arrangement 1962, such as in a male/female coupling. In the illustrated arrangement, the end portions 2000, 2002 define male portions that can be received in female portions (e.g., recesses or openings) of the mask 1952. Thus, the walls 2010 and or pocket 2012 can hold the lock arrangement 1962 in place and provide further support to the body portion 1970. In other words, the walls 2010 can function as a structural housing or enclosure for the lock arrangement 1962. The first end portion 2000, the mask 1952 or both can be configured to connect to a strap 1966, such as an elastic strap. The second end portion 2002, the mask 1952 or both can be configured to support a tube 1968 that houses a free end portion of a core member 1964. Preferably, the mask 1952 is configured to accommodate the tube 1968, which can include being specifically configured to receive the tube 1968 (or having an integrated tube) or simply being compatible with the presence of the tube 1968 (such as possessing sufficient open or available space to receive the tube 1968).

Interface assemblies disclosed herein can utilize a generally elastic portion and a generally inelastic portion, which cooperate to define at least a portion of a loop or circumference of the interface assembly. The elastic portion allows the size of the interface assembly to vary. The inelastic portion can form a structural portion of the loop or circumference or can simply be utilized for directional locking purposes, or both. Regardless, it is often necessary or desirable to allow for extension or expansion of the interface assembly and then accumulation of the inelastic portion during retraction. For example, in the interface assembly of FIGS. 43-54, the core member 1964 moves with extension of the elastic strap 1966 and the tube 1968 acts as an accumulator to receive an excess portion of the core member 1964, depending on the instantaneous amount of extension.

Figure 61:
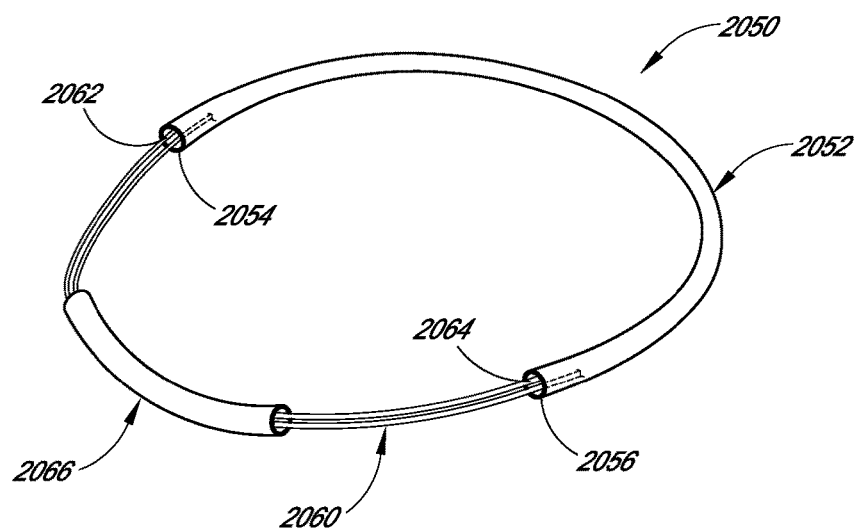
FIG. 61 is a perspective view of a headgear arrangement having an elastic portion and an inelastic portion and defining a complete loop.
Figure 62:
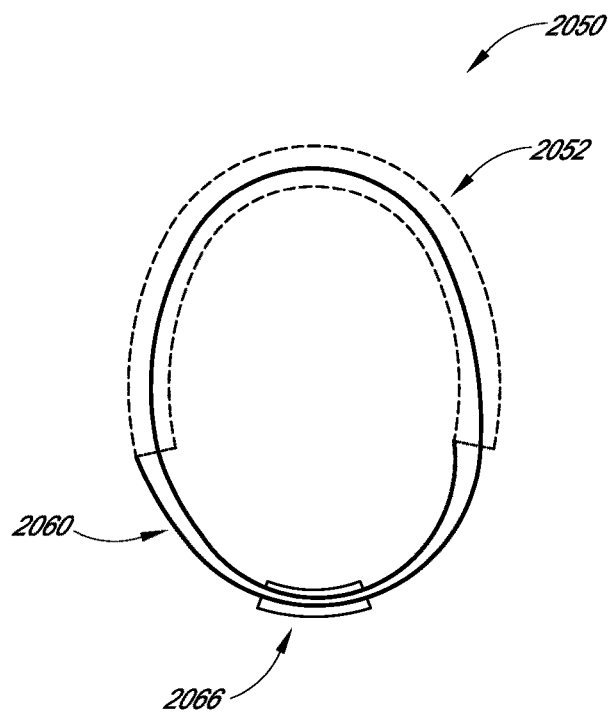
FIG. 62 is a top view of the headgear arrangement of FIG. 61.

Other arrangements are possible to provide for expansion and accumulation of a combined elastic/inelastic interface assemblies or headgear arrangements. FIGS. 61 and 62 illustrate a headgear arrangement 2050 including a tubular elastic element 2052 defining portion of a loop or circumference of the headgear arrangement 2050 and having a first end 2054 and a second end 2056. The illustrated tubular elastic element 2052 forms approximately one-half of the length of the loop; however, in other configurations, the elastic tubular element 2052 could form a lesser or greater proportion of the loop.

The headgear arrangement 2050 also includes a generally inelastic element 2060 that forms at least a portion of the loop and preferably is arranged in parallel with the elastic element 2052. In the illustrated arrangement, the inelastic element 2060 extends along more than the entire length of the loop. That is, preferably, a first end 2062 of the inelastic element 2060 is secured to the first end 2054 of the elastic element 2052 and a second end 2064 of the inelastic element 2060 is secured to the second end 2056 of the elastic element 2052. From the first end 2062, the inelastic element 2060 extends outside of the elastic element 2052, into the second end 2056 of the elastic element 2052, through the interior of the elastic element 2052, out of the first end 2054 of the elastic element and then, as described above, the second end 2064 of the inelastic element 2060 is secured to the second end 2056 of the elastic element 2052. Thus, two overlapping lengths or sections of the inelastic element 2060 are provided outside of the elastic element 2052. The headgear arrangement 2050 preferably includes a connector 2066 that connects the headgear arrangement 2050 to an interface, such as a mask. In the illustrated arrangement, the connector 2066 is a tubular member through which both external sections of the inelastic element 2060 extend. The connector 2066 can connect to the mask in any suitable manner, including being clipped onto or integrated into the mask, for example.

Figure 63:
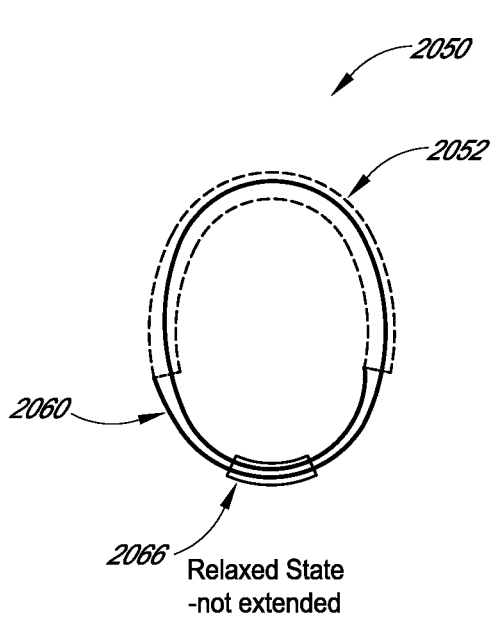
FIG. 63 is a top view of the headgear arrangement of FIG. 61 in a relatively retracted position.
Figure 64:
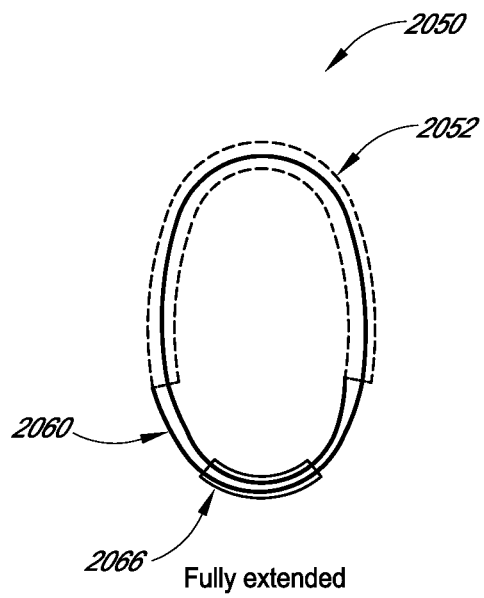
FIG. 64 is a top view of the headgear arrangement of FIG. 61 in a relatively extended position.

To extend in length, more of the inelastic element 2060 is pulled into the interior of the elastic element 2052 (or, viewed another way, the elastic element 2052 stretches to cover a greater portion of the inelastic element 2060). As a result, the length of the overlapping sections of the inelastic element 2060 is reduced such that the effective length of the circumference of the inelastic element 2060 (and the headgear arrangement 2050) is increased. To retract in length, the opposite action occurs so that a lesser portion of the inelastic element 2060 is positioned within the elastic element 2052 and a length of the overlapping sections of the inelastic element 2060 is increased. Relatively retracted and relatively extended positions are illustrated in FIGS. 63 and 64.

Figure 65:
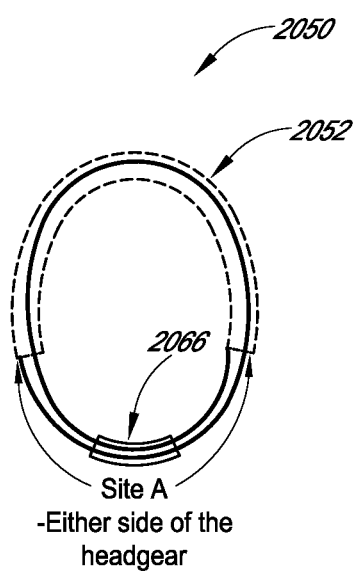
FIG. 65 is a top view of the headgear arrangement of FIG. 61 illustrating a first example placement for directional locks.
Figure 66:
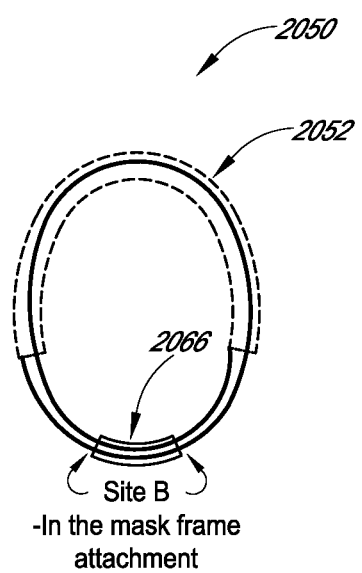
FIG. 66 is a top view of the headgear arrangement of FIG. 61 illustrating a second example placement for directional locks.

If directional locking is desired, one or more directional locks, such as any of those described herein, can be incorporated into the headgear arrangement 2050. FIG. 65 illustrates one example placement for directional locks at one or both ends 2054, 2056 of the elastic element 2052, which can act on relative movement between the ends 2054, 2056 and the inelastic element 2060. FIG. 66 illustrates an alternative or additional placement for directional locks, such as at either end of the connector 2066 and acting on relative movement between the inelastic element 2060 and the connector 2066.

Figure 67:
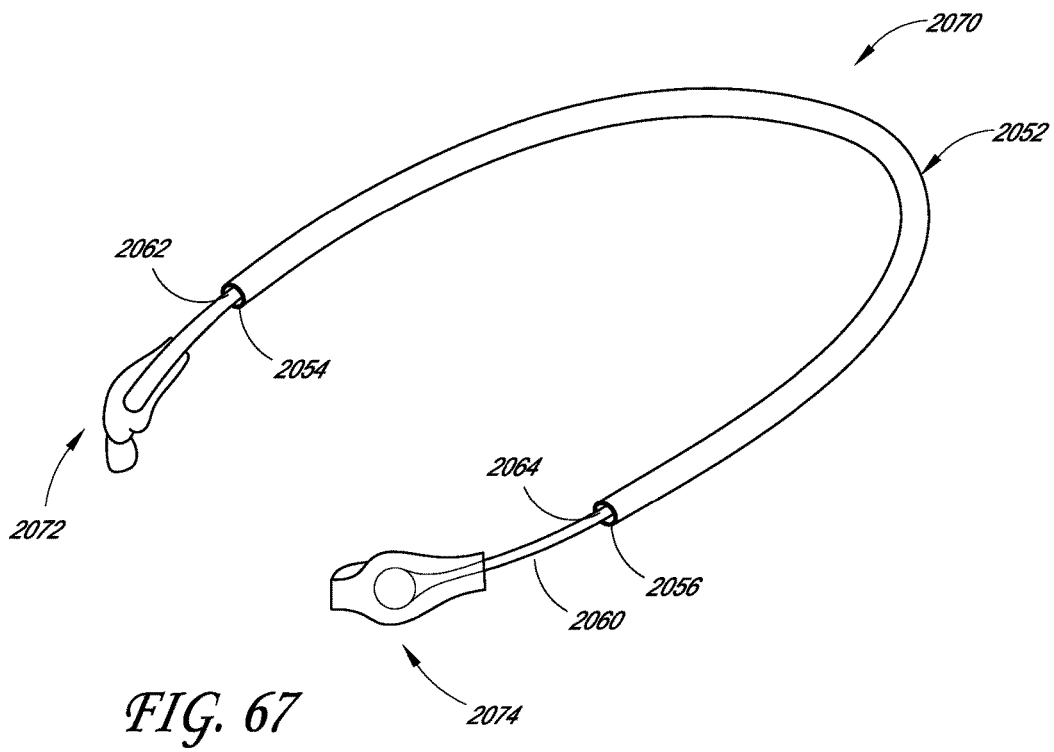
FIG. 67 is a perspective view of a headgear arrangement having an elastic portion and an inelastic portion and defining an interrupted loop.
Figure 68:
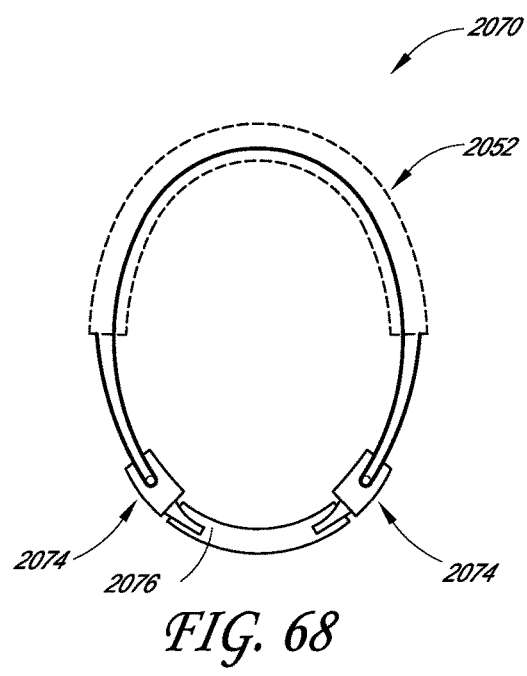
FIG. 68 is a top view of the headgear arrangement of FIG. 67.

FIGS. 67 and 68 illustrate another headgear arrangement 2070 that includes an elastic element 2052 and an inelastic element 2060. However, whereas the headgear arrangement 2050 is an endless loop or uninterrupted circle, the headgear arrangement 2070 is an interrupted design having a first end portion 2072 and a second end portion 2074, which can be coupled to respective sides of a patient interface, such as a mask 2076 (FIG. 68). Thus, the first end portion 2072 and the second end portion 2074 can each define an engagement portion, such as a hook or clip, for example, which permits the end portion 2072 or 2074 to be coupled to the mask 2076 or other interface. However, each of these arrangements can be considered to substantially surround the head of a user because ends of the interrupted design are interconnected by the patient interface.

Figures 69, 70:
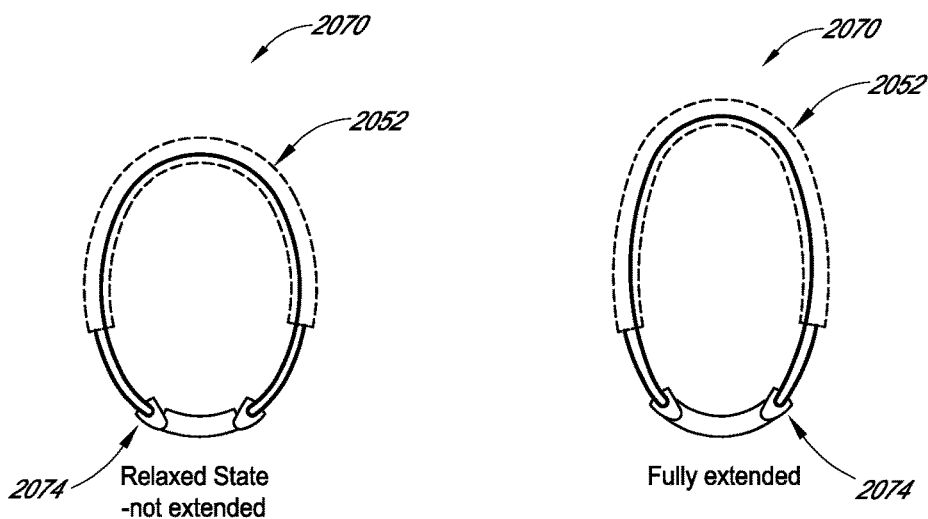
FIG. 69 is a top view of the headgear arrangement of FIG. 67 in a relatively retracted position.
FIG. 70 is a top view of the headgear arrangement of FIG. 67 in a relatively extended position.

In the headgear arrangement 2070 of FIGS. 67 and 68, the external sections of the inelastic element 2060 double back on themselves and are secured to the same side of the elastic element 2052 instead of overlapping one another and being secured to the opposite sides of the elastic element 2052, as in the headgear arrangement 2050 of FIGS. 61 and 62. Each of the end portions 2072, 2074 can include a pulley, which can be fixed or free (rotatable), or another suitable arrangement to reverse a direction of the external section of the inelastic element 2060. The operation of the headgear arrangement 2070 is substantially similar to the headgear arrangement 2050 in that a length of the external sections is increased to reduce the length of the headgear arrangement 2070, as illustrated in FIG. 69, or decreased to increase the length of the headgear arrangement 2070, as illustrated in FIG. 70. In addition, more or less of the inelastic element 2060 is exposed or covered by the elastic element 2052 as a result of a change in overall length of the headgear arrangement 2070.

Figures 71, 72:
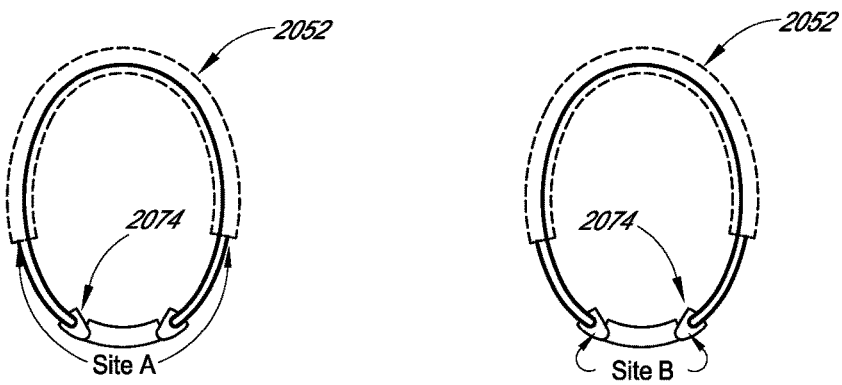
FIG. 71 is a top view of the headgear arrangement of FIG. 67 illustrating a first example placement for directional locks.
FIG. 72 is a top view of the headgear arrangement of FIG. 67 illustrating a second example placement for directional locks.

If directional locking is desired, one or more directional locks, such as any of those described herein, can be incorporated into the headgear arrangement 2070. FIG. 71 illustrates one example placement for directional locks at one or both ends 2054, 2056 of the elastic element 2052, which can act on relative movement between the ends 2054, 2056 and the inelastic element 2060. FIG. 72 illustrates an alternative or additional placement for directional locks, such as on either one or both of the first end portion 2072 and the second end portion 2074. In such an arrangement, the directional lock can act on relative movement between the inelastic element 2060 and the first end portion 2072 or the second end portion 2074.

Figure 73:
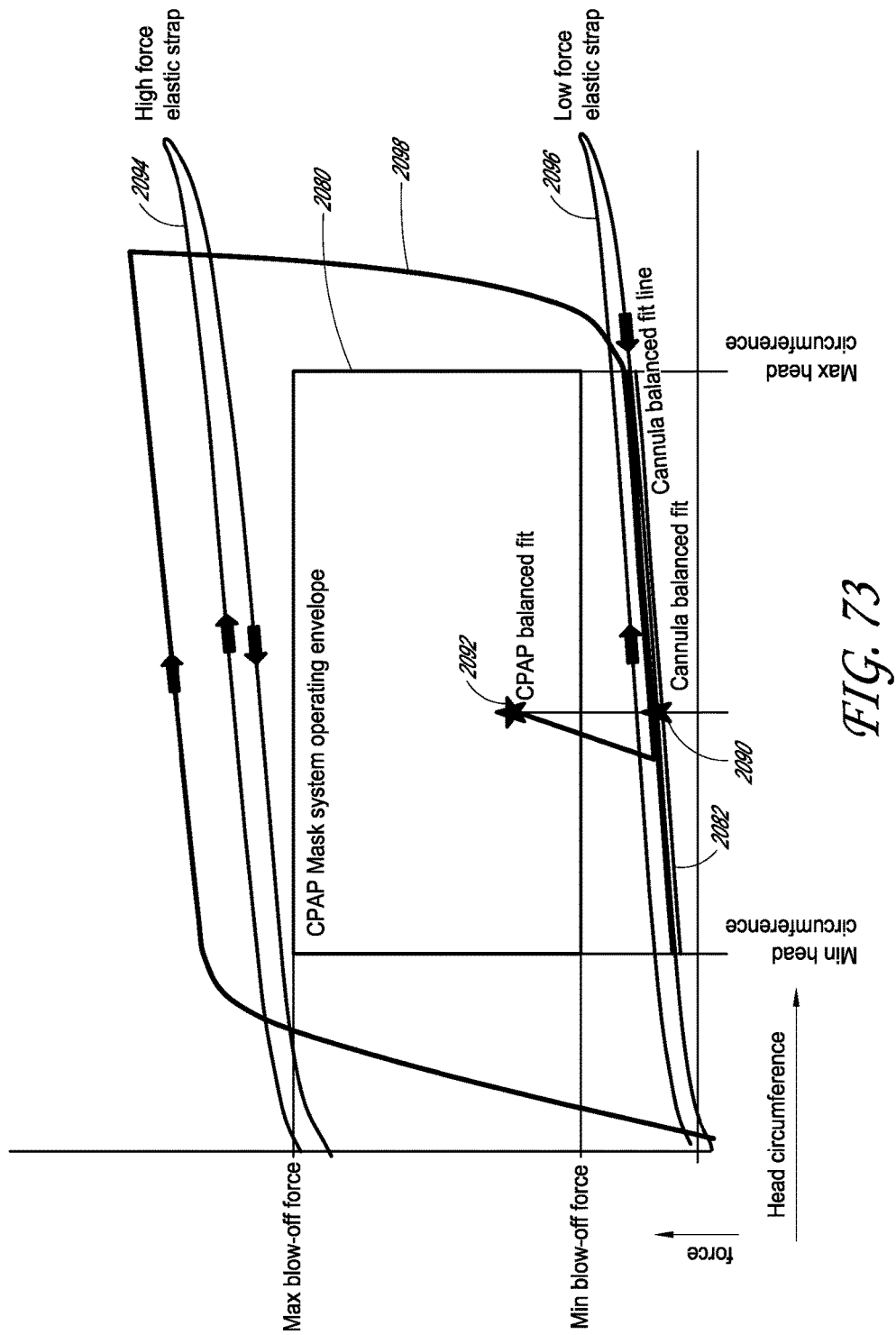
FIG. 73 is a graph that illustrates force profiles for CPAP balanced fit, cannula balanced fit, high force elastic strap and low force elastic strap relative to a CPAP operating envelope.

As discussed herein, embodiments of the present interface assemblies with balanced fit properties can be used with, or can be modified for use with, cannulas or other similar interfaces that do not create a seal with the user's face and, therefore, do not develop blow-off forces. FIG. 73 compares several force profiles and illustrates a balanced fit point of a cannula 2090 versus a balanced fit point of a CPAP mask 2092 within a one-way friction force profile 2098, which is an example force profile that can be provided by the interface assemblies described herein. As illustrated, a balanced fit generally occurs at different forces for CPAP and cannula systems. For a cannula or similar non-sealing system, the balanced-fit point 2090 occurs once the head circumference has been matched because no blow-off forces, or at least no substantial blow-off forces, are developed. In a CPAP system, the balanced-fit point 2092 occurs once head circumference and blow-off forces have been matched. For a CPAP system, the headgear preferably provides for a balanced fit point 2092 that could occur anywhere within the CPAP mask system operating envelope 2080. For a cannula system, the balanced fit point 2090 preferably will occur somewhere along the cannula balanced fit line 2082, which is defined by the lower force line of the one-way friction force profile 2098. The cannula balanced fit line 2082 shows that the force required to hold a cannula in place on a user's face preferably will be lower than the minimum force required to hold a CPAP mask in place and will generally fall within a smaller range because of the lack of blow-off forces.

FIG. 73 also compares the force profiles of a high force elastic strap 2094 and a low force elastic strap 2096 with the high hysteresis one-way friction force profile 2098. Low force elastic straps can be used in conjunction with cannulas to provide a comfortable fit for the user that is capable of overcoming just the weight of the cannula. However, such arrangements generally will not be capable of accommodating any significant external forces such as hose pull. In order to accommodate external forces, or blow-off forces in the case of CPAP treatment, a high force elastic strap generally is required. The force applied by a high force elastic strap headgear generally should be sufficient to accommodate the highest possible force that is expected to be applied to the mask, whilst on the smallest possible head size (shown by the shaded mask system operating envelope 2080). This, however, has the disadvantage of applying a higher than necessary minimum force when there is low blow-off forces and/or no external forces, which can be uncomfortable for users. The one-way friction force profile 2098 shows that it provides the benefits of both the high and low force elastic straps. That is, the one-way friction force profile 2098 provides high resistance to elongation and low forces in the absence of blow-off or external forces.

Figure 74:
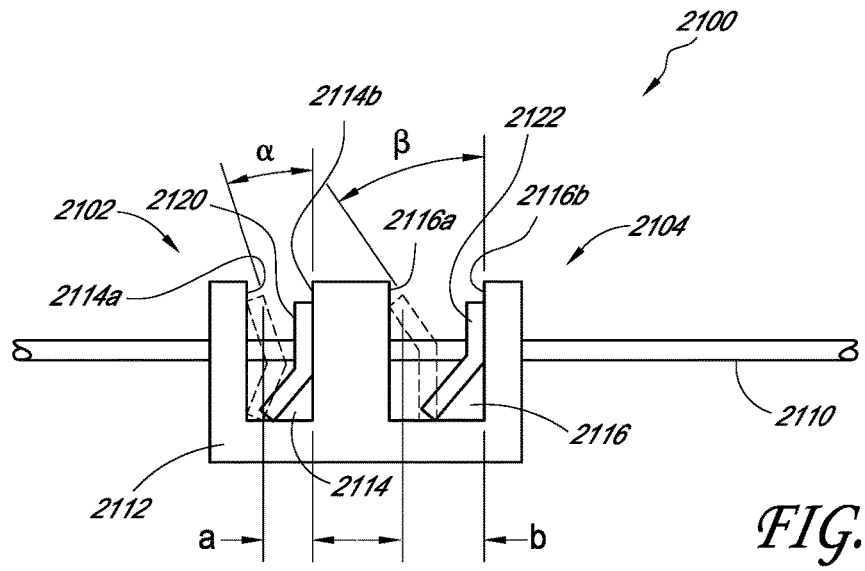
FIG. 74 is a partial sectional view of a multi-stage directional lock.

FIG. 74 illustrates a directional lock 2100 that involves principles of operation similar to other directional locks disclosed herein, such as the directional locks of FIGS. 16, 21, 32, 33, 40-42 and 43-51, for example and without limitation. However, the directional lock 2100 illustrated in FIG. 74 is a dual stage directional lock, which incorporates two different lock stages 2102, 2104. Preferably, the two lock stages 2102, 2104 have locking behaviour or characteristics that are different from one another. For example, the first lock stage 2102 can be a quick activation lock, which moves more quickly between a release position and a lock position than the second lock stage 2104. The second lock stage 2014 can be a high force lock, which provides a higher lock or yield force than the first lock stage 2102. Such an arrangement can allow optimization of both activation and lock force characteristics of the directional lock 2100. Features or details not described with respect to the directional lock 2100 can be the same or similar to corresponding features or details of the arrangements of FIG. 16, 21, 32, 33, 40-42 or 43-51, or can be of another suitable configuration.

The illustrated directional lock 2100 includes a core member 2110 (e.g., a core wire) that passes through a lock body, which can be any suitable enclosure or housing 2112. The housing 2112 defines two lock chambers 2114 and 2116. Each lock chamber 2114, 2116 has a lock member 2120, 2122 (e.g., a lock washer) positioned therein. As described previously, the core member 2110 passes through an opening in the lock members 2120, 2122. Each lock chamber 2114, 2116 has a first stop surface 2114a, 2116a spaced from a second stop surface 2114b, 2116b in a direction of movement of the core member 2110 to limit movement of the respective lock members 2120, 2122. The stop surfaces 2114a, 2116a, 2114b, 2116b can be defined by a wall of the housing 2112 or any other structure suitable to limit movement of the lock members 2120, 2122.

The lock members 2120, 2122 are movable between a lock position, in which resistance to movement of the core member 2110 is increased, and a release position, in which resistance to movement of the core member 2110 is reduced. In some configurations, movement of the core member 2110 moves the lock members 2120, 2122 between the lock position and the release position. In the illustrated arrangement, unlike the previously-described arrangements, the stop surfaces 2114a, 2116a, 2114b, 2116b are flat or planar and the lock members 2120, 2122 are bent to define an effective lock angle that operates in a manner similar to the previously-described arrangements. In particular, an opening of the lock members 2120, 2122 through which the core member 2110 passes can be generally aligned with an axis of the core member 2110 in the release position to reduce friction and, thus, lock force and the opening can be canted or angled in the lock position to increase friction and, thus, lock force. In the illustrated arrangement, the lock position is when the lock members 2120, 2122 are moved to the left and a portion of the lock members 2120, 2122 are flat against the stop surfaces 2114a, 2116a and the release position is when the lock members 2120, 2122 are moved to the right and the edges of the lock members 2120, 2122 are contacting the stop surfaces 2114b, 2116b. However, this arrangement could also be reversed.

In either arrangement, angles $\alpha$ and $\beta$, respectively, are defined by the difference between the release position and the lock position of the lock members 2120, 2122. Preferably, angle $\alpha$ is different than angle $\beta$. In some configurations, angle $\alpha$ is less than angle $\beta$. As described previously, in some configurations, the core member can move relative to the housing while the lock member, in the case of a single lock, moves from the release to the lock position or when the lock member moves from the lock to the release position. In some cases, the movement of the core member is related to the angle of the lock member between the release position and the lock position. As also described previously, in some configurations, the lock force is related to the lock angle, with the lock force increasing with the lock angle. Thus, a trade-off can exist between providing a high lock force and providing small core member movement between a release position and a lock position. The amount of core member movement required to move between the release position and the lock position can be referred to in terms of the lock's activation length (amount of core movement) or activation speed (time required to transition between release and lock positions), which can be influenced by the force tending to move the core member (e.g., retraction force of the headgear).

In the illustrated arrangement, the first lock stage 2102 is a quick activation lock, which moves between a release position and a lock position with less core member 2110 movement or more quickly than the second lock stage 2104. The lock member 2120 or core member 2110 movement between the release position and the lock position is illustrated by the distance "a" in FIG. 74. The relatively small movement distance allows the first lock stage 2102 to move between the release position and the lock position in response to small adjustment movements of the associated interface assembly. In some applications, the focus is on the movement from the release position to the lock position because the lock 2100 will allow movement of the core member 2110 (and extension of the associated headgear) until the lock 2100 moves to the lock position. However, movement in the other direction can also require core member movement and, in some applications, may be a characteristic of interest.

In use, the user may attempt to microadjust the interface assembly by wiggling or pushing on the mask/interface to compress the seal, thereby causing the headgear to retract or the core member 2110 to move in a direction tending to move the lock member 2120 toward the release position (to the right in FIG. 74). The first lock stage 2102 moves quickly to the lock position once the user removes the pushing force from the mask/interface and allows a preferably small amount of expansion of the associated headgear. As a result, the directional lock 2100 is responsive to small movements of the mask/interface and locks the mask/interface very close to the desired adjustment position. As discussed above, the first lock stage 2102 can move quickly to the lock position due to a relatively small lock angle α. However, the first lock stage 2102 may provide a maximum lock force that is lower than a desired lock force, which may also be a result of the relatively small lock angle α.

However, the second lock stage 21044 can be a high force lock, which can provide a desired maximum lock force for the directional lock 2100. The second lock stage 2104 can have a movement of the lock member 2122 or core member 2110 between the release position and the lock position that is illustrated by the distance "b" in FIG. 74. In some configurations, the distance "b" is greater than the distance "a" of the first lock stage 2102. As described above, the lock angle 3 of the second lock stage 2104 can be greater than the lock angle α, which in some configurations can result in the second lock stage 2104 having a higher lock force than the first lock stage 2102. Combining the first lock stage 2102 and the second lock stage 2104 can result in a direction lock 2100 that is responsive to small adjustment movements of the associated headgear/interface, while also providing a lock or yield force that is sufficient to address normal or expected operational forces.

In some configurations, the distance "a" is about 1 millimeter or less to provide for micro-adjustment of the associated headgear/interface. However, in some configurations, the distance "a" can be greater than 1 millimeter. The distance "a" can be selected based on a lock distance that is tolerable for a given application. In other words, the distance "a" can be selected based on the level of micro-adjustment that is necessary or desirable for a given application. As described above, an interface assembly can comprise more than one directional lock, such as one on each side of the interface assembly, for example. Accordingly, the total lock distance can be greater than the lock distance of a single directional lock and, in some cases, can be the sum of the individual lock distances. The distance "b" can be selected to achieve a desired maximum lock force. In some configurations, the distance "b" can be at least about twice as great, at least about five times as great, at least about ten times as great or at least about twenty times as great as the distance "a". The ratios of the angles α and β can be the same as or similar to the ratios of the distances "a" and "b".

Figure 75:
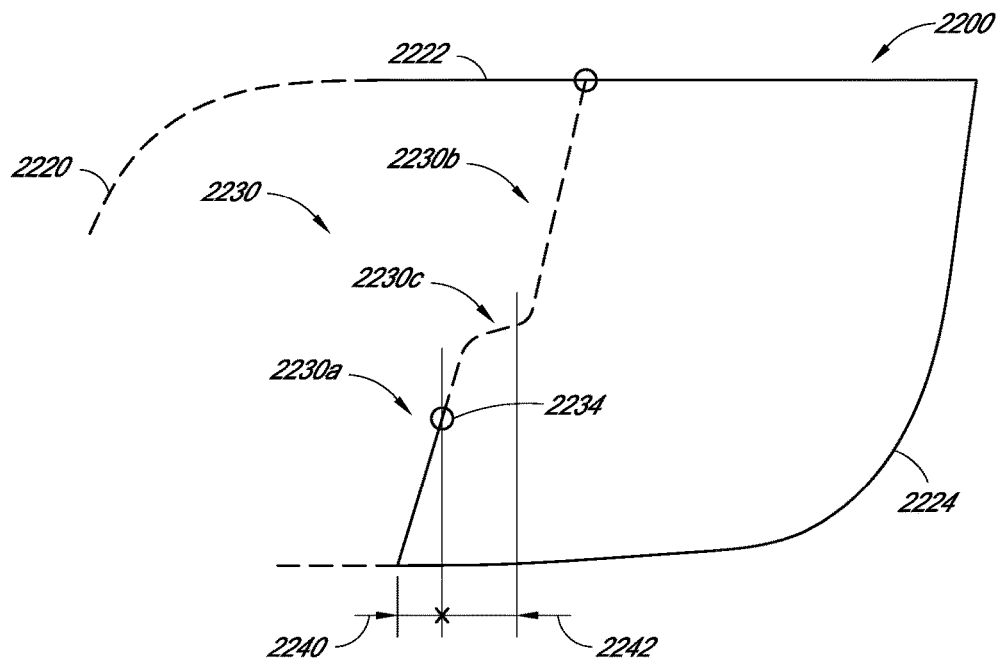
FIG. 75 is a graph illustrating a force profile of a multi-stage directional lock.

FIG. 75 illustrates a force profile 2200 of a headgear or interface assembly comprising at least one dual stage directional lock, such as the directional lock 2100 of FIG. 74. The force profile 2200 can be generally similar to the force profiles discussed in connection with FIGS. 2-5. Thus, the force profile 2200 includes an initial steep rise 2220 illustrating the initial resistance to stretch. The force profile also includes a substantially flat, generally constant extension curve 2222 illustrating further stretch of the headgear and a decline 2224 as the headgear retracts to fit the user's head. However, in contrast to the force profiles of FIGS. 2-5, the force profile 2200 includes a stepped balanced fit section 2230, which illustrates a transition between the first lock stage 2102 and the second lock stage 2104.

In particular, the balanced fit section 2230 can include a first portion 2230a and a second portion 2230b. The first portion 2230a can be related to the characteristics of the first lock stage 2102 and the second portion 2230b can be related to the characteristics of the second lock stage 2104. The second portion 2230b can also be influenced by resistance offered by the first lock stage 2102 in combination with the second lock stage 2104. As illustrated, the second portion 2230b is offset from the first portion 2230a by a transition portion 2230c, which can reflect a transition from the first lock stage 2102 to the second lock stage 2104. That is, the offset can be reflective of a difference between the distance "b" and the distance "a" in FIG. 74.

The balance fit section 2230 includes a solid line portion, which illustrates extension of the headgear up until the balanced fit point 2234. The dashed line portion above the balanced fit point 2234 illustrates additional extension that would occur in the headgear in response to additional forces. In the illustrated arrangement, the balanced fit point 2234 falls within a capability range of the first lock stage 2102. That is, the balanced fit point 2234 is less than the maximum lock force of the first lock stage 2102. However, in some cases, such as high therapy pressures, the balance fit point 2234 may be above the maximum lock force of the first lock stage 2102 and may fall within the second portion 2230b of the balanced fit section 2230. Preferably, the balance fit point 2234 falls below the maximum lock force of the second lock stage 2104. A yield point 2236 can be defined by an intersection of the balanced fit section 2230 and the constant extension curve 2222.

An initial activation length 2240 is defined as the extension distance between a beginning of the balanced fit section 2230 and the balanced fit point 2234. The initial activation length 2240 can be related to the distance "a" of the first lock stage 2102. A secondary activation length 2242 can be defined as the extension distance between the balanced fit point 2234 and the end of the transition portion 2230c/beginning of the second portion 2230b of the balanced fit section 2230. The secondary activation length 2242 can be related to the distance "b" of the second lock stage 2104. The force profile 2200 is merely an example of a force profile that can be provided by a dual stage directional lock, such as the lock 2100. Directional locks having a variety of different force profiles to suit a particular application or desired performance criteria can be achieved based on the teachings of the present disclosure. For example, multiple individual locks of any type disclosed herein can be combined to created dual or multi-stage locks. The individual locks can be of the same type or can vary in type within a single dual or multi-stage lock.

Although certain mechanical directional lock arrangements are specifically illustrated herein, other mechanical and non-mechanical methods and arrangements for achieving a self-fit, large hysteresis or directional lock can also be used. For example, electric, piezoelectric, pneumatic, hydraulic or thermomechanical arrangements can be configured to provide functionality similar to the interface assemblies disclosed herein. In some configurations, such methods or arrangements can selectively grip or release an inelastic core similar to the arrangements disclosed herein.

In one example of an electric arrangement, a solenoid clutch can be employed to provide a directional lock function. For example, an electric coil around a plunger can move the plunger when energized. This movement can be utilized to directly or indirectly pinch or grip the non-stretch member of the self-adjust headgear to hold the non-stretch member. The holding mechanism can release the non-stretch member to allow elongation. The solenoid clutch can be controlled by any suitable arrangement, such as a button. Alternatively, a sensor could determine when the headgear is positioned and/or when a CPAP pressure is activated and the holding mechanism could be activated.

Alternatively, a stepper motor or servo motor could be utilized to actively hold the position of an adjustable member of the headgear, such as a non-stretch member. Retraction and/or extension can be accomplished by the motor. In some configurations, an electromagnetic force generator could be utilized to act on an adjustable member of the headgear having magnetic sections or properties. Retraction could be accomplished by a linear motor. In some configurations, an electro-active polymer can be utilized to create a clutch or pinching mechanism in response to an electrical current that acts on and holds an adjustable member of the headgear. Alternatively, an electro-magnetic force can act on a magnetic liquid to create a clutch or pinching mechanism that can hold an adjustable member of the headgear.

In an example of a piezoelectric arrangement, a piezoelectric clutch or clamp can be utilized to release free movement of the non-stretch headgear. Examples of piezo-mechanisms include piezo-membrane (buzzer), diesel engine valves and inkjet nozzles. Each of these mechanisms use a piezo element to create a movement/displacement. Such a piezo-mechanism could be used directly or to drive a holding clutch to selectively hold an adjustable member of a self-fit headgear. A few piezoelectric components could be configured to create a so-called inchworm motor. An inchworm motor (or similar) arrangement is specifically useful for linear motion. Such movement can be utilized in the adjustment of a self-fit headgear arrangement.

In a pneumatic arrangement, a pneumatic cylinder or pneumatic bellows can operate a clutch or gripping mechanism activated by CPAP pressure or an auxiliary air/gas supply. The clutch or gripping mechanism can directly or indirectly hold an adjustable member of a self-fit headgear. Similarly, in a hydraulic arrangement, a hydraulic cylinder or bladder could be utilized to hold an adjustable member of a self-fit headgear. CPAP pressure could be utilized to pressurize the hydraulic fluid, for example. Alternatively, a piston could be mechanically moved to pressurize the hydraulic fluid.

In a thermomechanical arrangement, a thermo-sensitive substance (e.g., wax) can be utilized to actuate a clutch or holding mechanism for holding an adjustable member of a self-fit headgear. Activation of the clutch or holding mechanism can be driven from contact with or proximity to warmth of the user's skin or another suitable heat source, such as a heated breather tube of the CPAP system. Wax filled cartridges are commonly used to operate thermostatic valves. The wax expands or contracts with changing temperatures, which is subsequently transformed into movement of, for instance, a plunger. In absence of sufficient heat, the clutch can release its grip to allow for fitting of the headgear to the user. Once the headgear is in place and the thermomechanical clutch is exposed to the heat source, the clutch can engage to hold the headgear from expanding.

Another example of a thermo-sensitive substance is a bi-metallic member that deforms under the influence of heat, which displacement can be utilized to activate a holding clutch or lock of the self-fit headgear.

While various embodiments have been described, it should be noted that any of the adjustment mechanisms can be combined with any of the other assemblies. In addition, the adjustment mechanisms can be used without a break-fit assembly and the break-fit assemblies can be used without an adjustment mechanism. Further, any interface (i.e., mask and headgear) can be used with either or both of an adjustment mechanism described herein and/or a break-fit assembly. The break-fit assembly can include those described in U.S. Provisional Patent Application No. 61/681,024, filed on Aug. 8, 2012, for example but without limitation, which is hereby incorporated by reference in its entirety.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A patient interface system comprising:
an interface portion adapted to create a seal with at least a nose of a user;
a coupling that permits the patient interface system to be coupled to a gas delivery system;
a headgear system that allows the interface portion to be positioned and retained on a head of the user with the headgear system providing a transformational locking behavior with an ability to transform from an elastic type elongation behavior to a generally non-elongating type behavior when the patient interface system is in use;
the headgear system comprising a mechanical directional lock, a rear portion, and at least one side strap on each side of the headgear system that couples the rear portion to the interface portion, each side strap comprising a non-elongating element and an elastic element;
wherein the elastic type elongation behavior is provided by the elastic elements, the elastic elements being configured to provide a retraction force;
wherein the transformational locking behavior is provided by the mechanical directional lock, which is configured to apply a friction force on the one or more non-elongating elements in use such that movement in a retraction direction is automatically allowed at a first level of resistance and movement in an elongation direction is either automatically allowed at a second level of resistance higher than the first level of resistance or automatically prevented;
wherein the transformational locking behavior is adapted to automatically fit the headgear system to the user without the need for manual adjustment of the headgear assembly to fit the headgear system to the user.

2. The patient interface system of claim 1, wherein the headgear system provides the non-elongating type behavior in the range of about 0.5N to about 65N.

3. The patient interface system of claim 1, wherein the mechanical directional lock comprises a lock enclosure, a movable lock member and a core member.

4. The patient interface system of claim 3, wherein a cross-sectional dimension of the core member is in the range of about 0.1 mm to about 8 mm.

5. The patient interface system of claim 3, wherein the lock member is capable of moving relative to the core member through a range of angles between about 0° to about 45°.

6. The patient interface system of claim 3, wherein a lock holding force of the lock member is adjustable by the user.

7. The patient interface system of claim 3, wherein the mechanical directional lock incorporates a friction promoting surface to facilitate lock activation.

8. The patient interface system of claim 3, wherein the core member is a cord.

9. The patient interface system of claim 1, wherein, for at least one side strap, the elastic element is constructed as a braid where the elastic element and the non-elastic element are combined in such a manner that the non-elastic element provides a physical end stop to extension before the elastic element is plastically deformed.

10. The patient interface system of claim 1, wherein the mechanical directional lock comprises a housing, a movable lock member within the housing and a core member, wherein the housing guides movement of the core member, and wherein both the housing and the lock member are formed by a single integrated module.

11. The patient interface system of claim 1, wherein the mechanical directional lock comprises a lock module, and the lock module, the non-elastic portion and the elastic portion form a modular adjustment assembly.

12. The patient interface system of claim 11, wherein the interface portion is a mask and the modular adjustment assembly is connected to a frame of the mask.

13. The patient interface system of claim 12, wherein the frame comprises one or more walls defining a space that receives the lock module.

14. The patient interface system of claim 11, wherein the modular adjustment assembly is connected to a portion of the headgear system.

15. The patient interface system of claim 14, wherein the portion of the headgear system is the rear portion and comprises at least one of a lower rear strap and a crown strap.

16. The patient interface system of claim 1, wherein the transformational locking behavior has a first lock stage that provides a first lock force and a second lock stage that provides a second lock force, wherein the second lock force is greater than the first lock force.

17. A patient interface system comprising:
an interface portion adapted to create a seal with at least a nose of a user;
a coupling that permits the patient interface system to be coupled to a gas delivery system;
a headgear system that allows the interface portion to be positioned and retained on a head of the user with the headgear system providing a transformational locking behavior with an ability to transform from an elastic type elongation behavior to a generally non-elongating type behavior when the patient interface system is in use;
wherein the transformational locking behavior has a first lock stage that provides a first lock force and a second lock stage that provides a second lock force, wherein the second lock force is greater than the first lock force;
wherein the first lock stage transforms to the generally non-elongating type behavior with less elongation movement than the second lock stage.

18. A patient interface system comprising:
an interface portion;
a coupling that permits the interface portion to be coupled to a gas delivery system;
a headgear system that allows the interface portion to be positioned and retained on a head of the user with the headgear system providing a transformational locking behavior with an ability to transform from an elastic type elongation behavior to a generally non-elongating type behavior when the patient interface system is in use;
the headgear system comprising a mechanically based directional lock, a rear portion, and at least one side strap on each side of the headgear system that couples the rear portion to the interface portion, each side strap comprising a non-elongating element and an elastic element;
wherein the elastic type elongation behavior is provided by the elastic elements, the elastic elements being configured to provide a retraction force;
wherein the transformational locking behavior is provided by the mechanically based directional lock, the mechanically based directional lock configured to apply a friction force on the one or more non-elongating elements in use such that movement in a retraction direction is allowed at a first level of resistance and movement in an elongation direction is one of 1) allowed at a second level of resistance higher than the first level of resistance, and 2) prevented;
wherein the transformational locking behavior is adapted to automatically fit the headgear system to the user without the need for manual adjustment of the headgear assembly to fit the headgear system to the user; and
wherein the mechanically based directional lock comprises a dual stage directional lock comprising two different lock stages, the two lock stages having different locking behaviors.

19. The patient interface system of claim 18, wherein the two different lock stages are a first lock stage and a second lock state, and the first lock stage is a quick activation lock that moves more quickly between a release position and a lock position than the second lock stage.

20. The patient interface system of claim 19, wherein the second lock stage is a high force lock that provides a higher lock or yield force than the first lock stage.

* * * * *

UNITED STATES PATENT AND TRADEMARK OFFICE
CERTIFICATE OF CORRECTION

PATENT NO.      : 10,456,546 B2
APPLICATION NO. : 14/786942
DATED           : October 29, 2019
INVENTOR(S)     : Mark Arvind McLaren et al.

Page 1 of 1

It is certified that error appears in the above-identified patent and that said Letters Patent is hereby corrected as shown below:

In the Specification

In Column 3 at Line 24, Change "and or" to --and/or--.

In Column 4 at Line 27, After "65N" insert --.--.

In Column 20 at Line 40, After "802" insert --.--.

In Column 23 at Line 28, Change "at" to --α--.

In Column 36 at Line 67, Change "Netwons)." to --Newtons).--.

In Column 46 at Line 53, Change "and or" to --and/or--.

In Column 51 at Line 34, Change "3" to --β--.

In the Claims

In Column 56 at Line 52, In Claim 19, change "state," to --stage,--.

Signed and Sealed this
Fourth Day of February, 2020

Andrei Iancu
*Director of the United States Patent and Trademark Office*